(12) United States Patent
Yu et al.

(10) Patent No.: US 9,249,383 B2
(45) Date of Patent: Feb. 2, 2016

(54) APPARATUS FOR CULTURING ANCHORAGE DEPENDENT CELLS

(75) Inventors: Hanry Yu, Singapore (SG); Lei Xia, Singapore (SG); Hwa Liang Leo, Singapore (SG)

(73) Assignee: AGENCY FOR SCIENCE TECHNOLOGY & RESEARCH, Connexis (SG)

( * ) Notice: Subject to any disclaimer, the term of this patent is extended or adjusted under 35 U.S.C. 154(b) by 622 days.

(21) Appl. No.: 13/123,200

(22) PCT Filed: Oct. 8, 2009

(86) PCT No.: PCT/SG2009/000369
§ 371 (c)(1),
(2), (4) Date: Jul. 1, 2011

(87) PCT Pub. No.: WO2010/042072
PCT Pub. Date: Apr. 15, 2010

(65) Prior Publication Data
US 2012/0129257 A1    May 24, 2012

Related U.S. Application Data

(60) Provisional application No. 61/136,838, filed on Oct. 8, 2008.

(51) Int. Cl.
*C12M 3/00* (2006.01)
*C12M 1/00* (2006.01)
*C12M 1/12* (2006.01)

(52) U.S. Cl.
CPC ............... *C12M 23/44* (2013.01); *C12M 21/08* (2013.01); *C12M 23/34* (2013.01); *C12M 23/46* (2013.01); *C12M 23/58* (2013.01); *C12M 25/06* (2013.01); *C12M 29/10* (2013.01)

(58) Field of Classification Search
CPC ...... C12M 23/34; C12M 23/58; C12M 25/06; C12M 1/14
USPC ............................................ 435/297.1, 299.2
See application file for complete search history.

(56) References Cited

U.S. PATENT DOCUMENTS 4,087,327 A * 5/1978 Feder et al. .................... 435/399
4,228,243 A * 10/1980 Iizuka ........................ 435/294.1
(Continued)

FOREIGN PATENT DOCUMENTS

DE        4200446 A1    6/1993
DE    202006013105 U1   12/2006
(Continued)

OTHER PUBLICATIONS

Xia et al., "Laminar-flow immediate-overlay hepatocyte sandwich perfusion system for drug hepatotoxicity testing", Biomaterials (2009) vol. 30, pp. 5927-5936.
(Continued)

*Primary Examiner* — Jonathan Hurst
(74) *Attorney, Agent, or Firm* — Stout, Uxa & Buyan, LLP; Carlos A. Fisher

(57) ABSTRACT

The invention relates to an apparatus (1) for culturing anchorage-dependent cells. The apparatus (1) comprises a housing (2) with an inlet (4) and an outlet (5), and a plurality of culture plates (6) removably stacked within the housing (2). The housing (2) has a circumferential wall (7), a base (8) and a top wall (9). The base (8) comprises the inlet (4) and the top wall (9) comprises the outlet (5). The circumferential wall (7) of the housing (2) defines a longitudinal axis thereof, as well as an inner cross section perpendicular to the longitudinal axis. Shape and dimensions of the inner cross section are essentially uniform along the longitudinal axis. The culture plates (6) are arranged at least essentially parallel to each other. Each plate (6) is mounted and sealed to the circumferential wall (7) of the housing (2). Plates (6) are arranged at a distance from each other. Each culture plate (6) has a through hole (14), so that inlet (4) and outlet (5) are in fluid communication. Each through hole (14) is positioned at an outer end of the respective culture plate (6), proximate the circumferential wall (7). Through holes (14) of adjacent culture plates (6) are distally positioned in the plane of the inner cross section of the housing (2).

25 Claims, 29 Drawing Sheets

(56) References Cited

U.S. PATENT DOCUMENTS

| | | | |
|---|---|---|---|
| 5,190,878 A * | 3/1993 | Wilhelm | 435/297.2 |
| 5,240,854 A * | 8/1993 | Berry et al. | 435/305.1 |
| 6,562,616 B1 | 5/2003 | Toner et al. | |
| 2007/0178583 A1 | 8/2007 | Berry | |
| 2007/0254356 A1 * | 11/2007 | Wilson et al. | 435/297.5 |
| 2008/0118974 A1 * | 5/2008 | Martin et al. | 435/297.1 |

FOREIGN PATENT DOCUMENTS

| | | |
|---|---|---|
| WO | 9000595 A1 | 1/1990 |
| WO | WO 03/085080 A1 | 10/2003 |
| WO | WO 2006/122088 A1 | 11/2006 |

OTHER PUBLICATIONS

Apel, P., "Track etching technique in membrane technology", Radiation Measurements (2001) vol. 34, pp. 559-566.

Park et al., "Radial Flow Hepatocyte Bioreactor Using Stacked Microfabricated Grooved Substrates", Biotechnol. Bioeng. (2008) vol. 99, No. 2, pp. 455-467.

Curcio et al., "Mass transfer and metobolic reactions in hepatocyte spheroids cultured in rotating wall gas-permeable membrane system", Biomaterials (2007) vol. 28, pp. 5487-5497.

Allen et al., "In Vitro Zonation and Toxicity in a Hepatocyte Bioreactor", Toxicol. Sci.(2005) vol. 84, pp. 110-119.

Park et al., "Bioartificial Liver Systems: Current Status and Future Perspective", J. Biosci. Bioeng. (2005) vol. 99, No. 4, pp. 311-319.

Allen et al., "Improving the next generation of bioartificial liver devices", Seminars in Cell Dev. Biol. (2002) vol. 13, No. 6, pp. 447-454.

Marion et al., "Use of Sandwich-Cultured Hepatocytes to Evaluate Impaired Bile Acid Transport as a Mechanism of Drug-Induced Hepatotoxicity", Mol. Pharm. (2007) vol. 4, No. 6, pp. 911-918.

Tilles et al., "Effects of Oxygenation and Flow on the Viability and Function of Rat Hepatocytes Cocultured in a Microchannel Flat-Plate Bioreactor", Biotechnol. Bioeng. (2001) vol. 73, No. 5, pp. 379-389.

Mareels et al., "Three-dimensional Numerical Modeling and Computational Fluid Dynamics Simulations to Analyze and Improve Oxygen Availability in the AMC Bioartificial Liver", Annals of Biomed. Eng. (2006) vol. 34, No. 11, pp. 1729-1744.

Yanagi et al., "Improvement of Metabolic Performance of Hepatocytes Cultured in Vitro in a Packed-Bed Reactor for Use as a Bioartificial Liver", ASAIO Journal (1998) vol. 44, pp. M436-M440.

Abstract: Smith et al., "Techniques for measurement of oxygen consumption rates of hepatocytes during attachment and post-attachment", Int. J. Artif. Organs, vol. 19, Issue 1, pp. 36-44, Published Jan. 1996.

Smith et al., "Techniques for measurement of oxygen consumption rates of hepatocytes during attachment and post-attachment", Int. J. Artif. Organs, (1996) vol. 19, No. 1, pp. 36-44.

Extended European Search Report, PCT/SG2009000369, mailed Mar. 25, 2014.

* cited by examiner

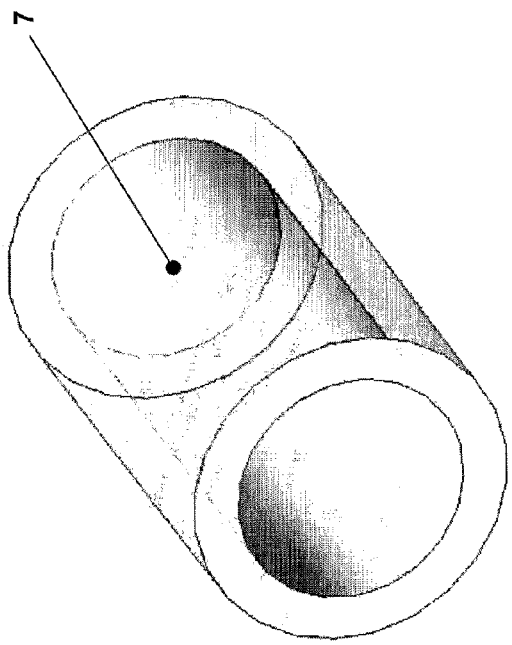
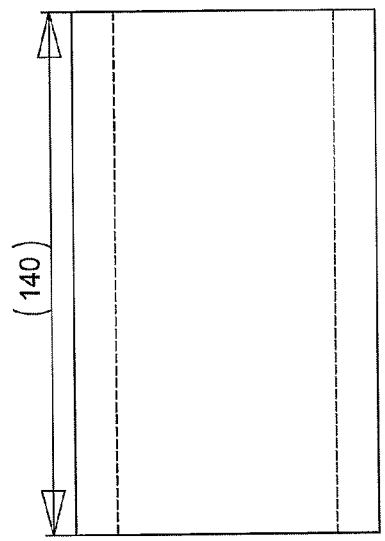
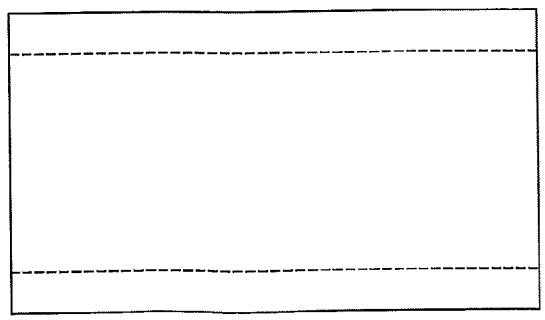
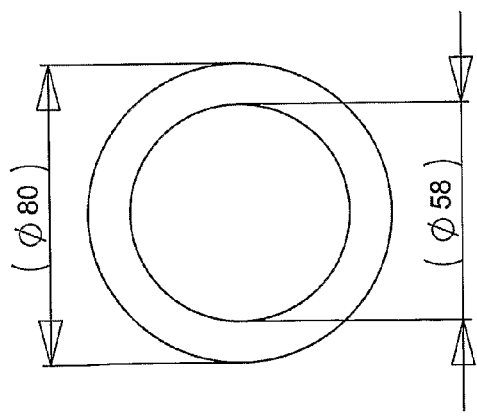
Fig. 4E

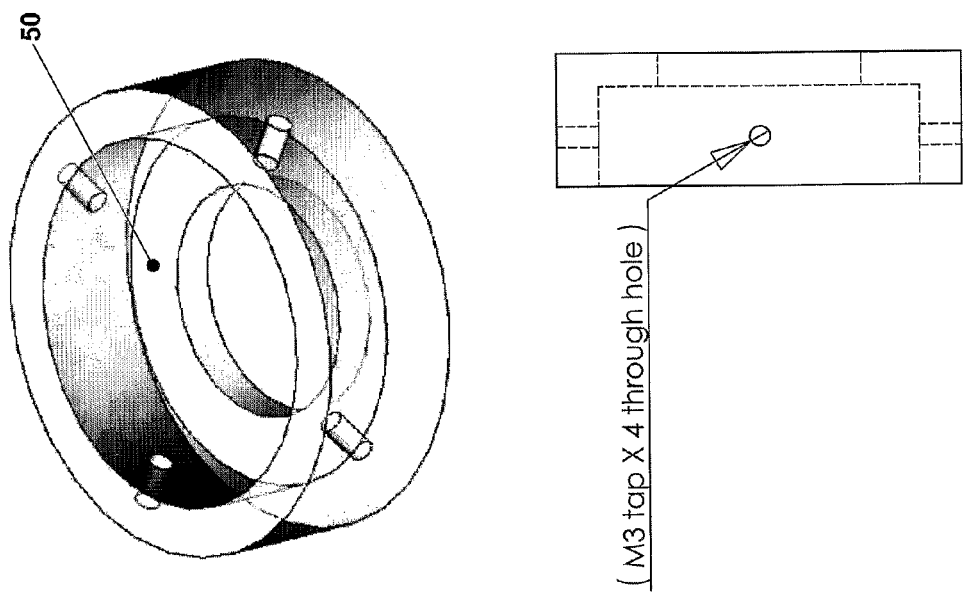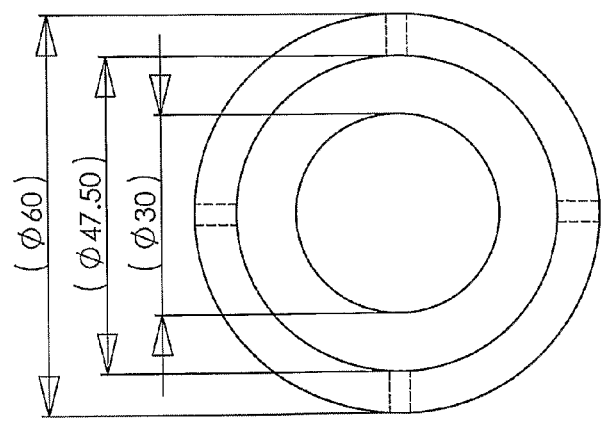
Fig. 4G

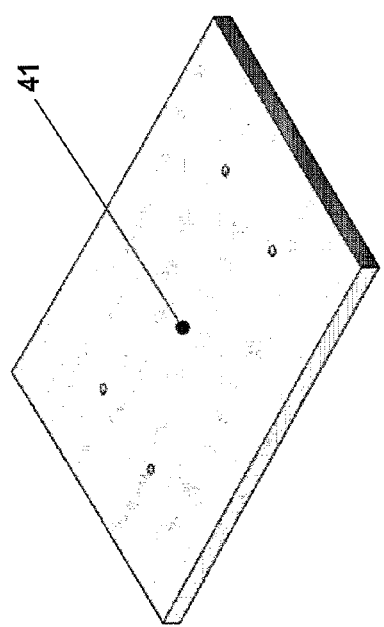
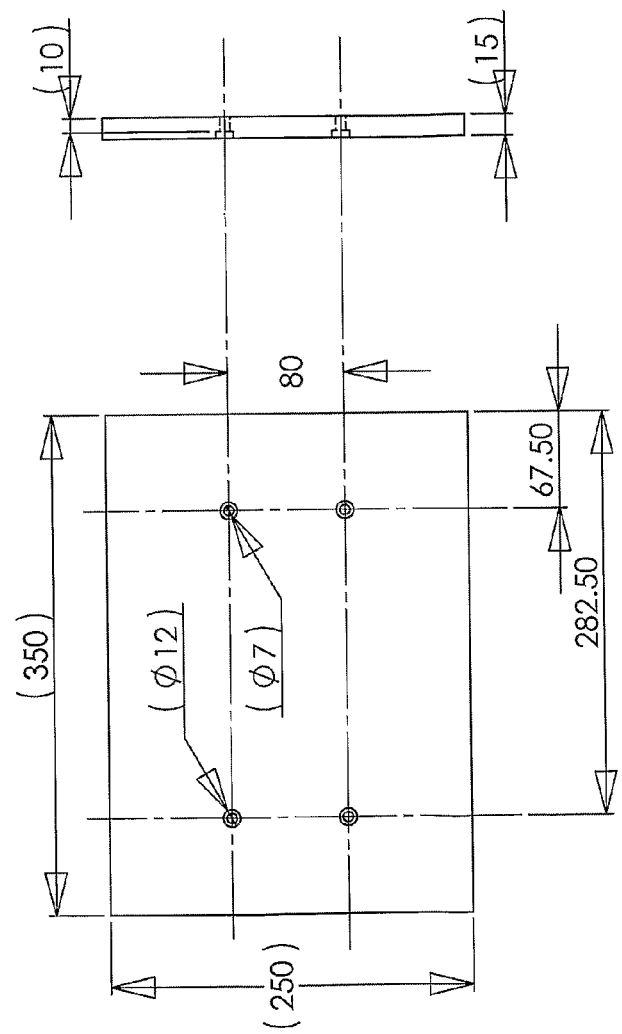
Fig. 4H

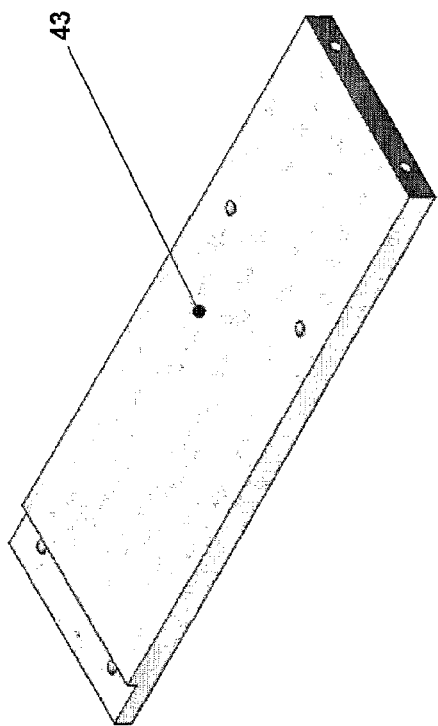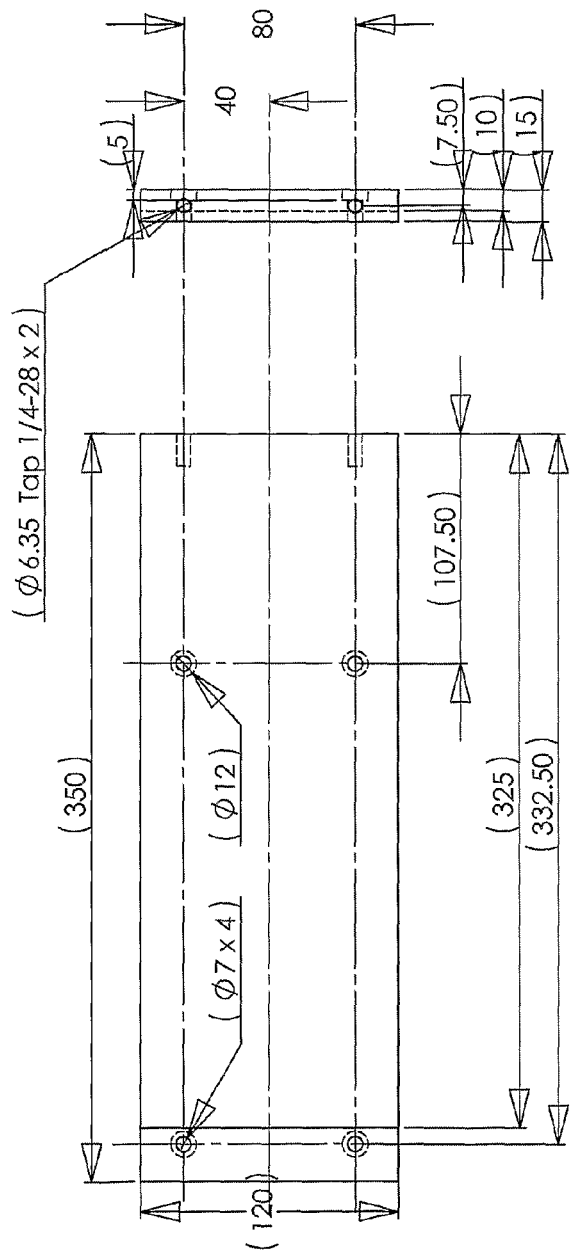
Fig. 4J

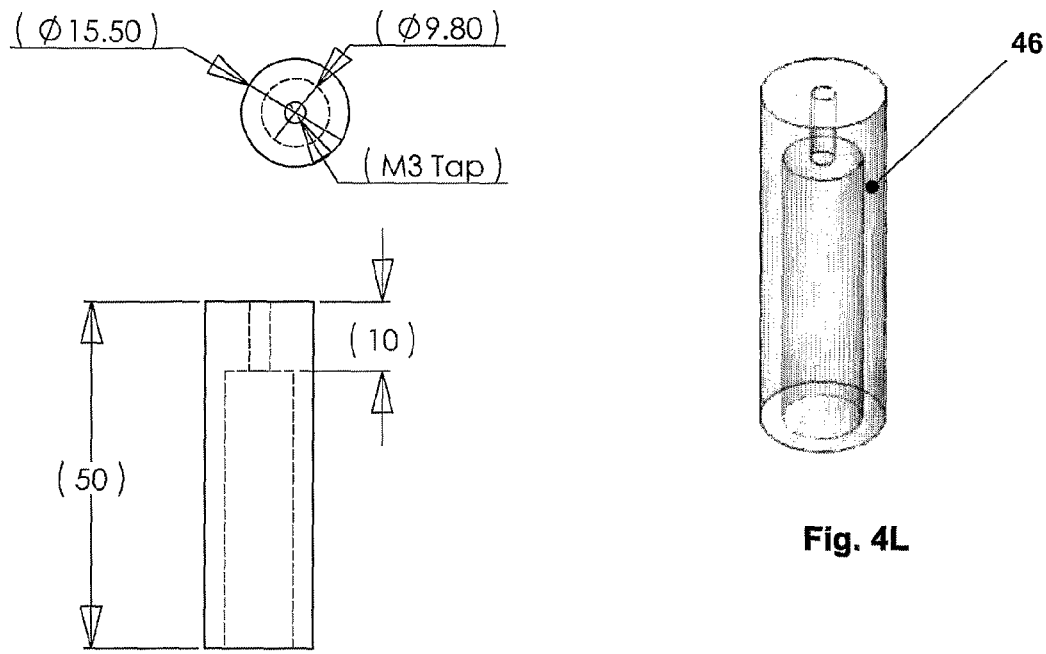
Fig. 4L
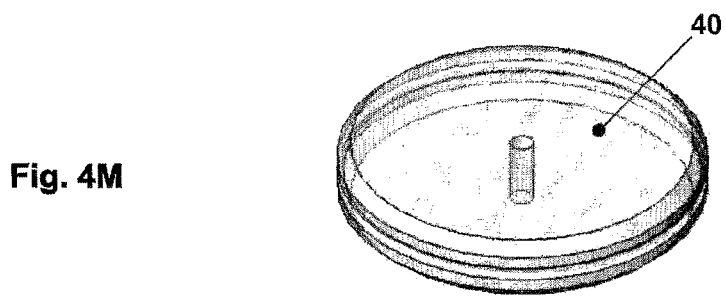
Fig. 4M
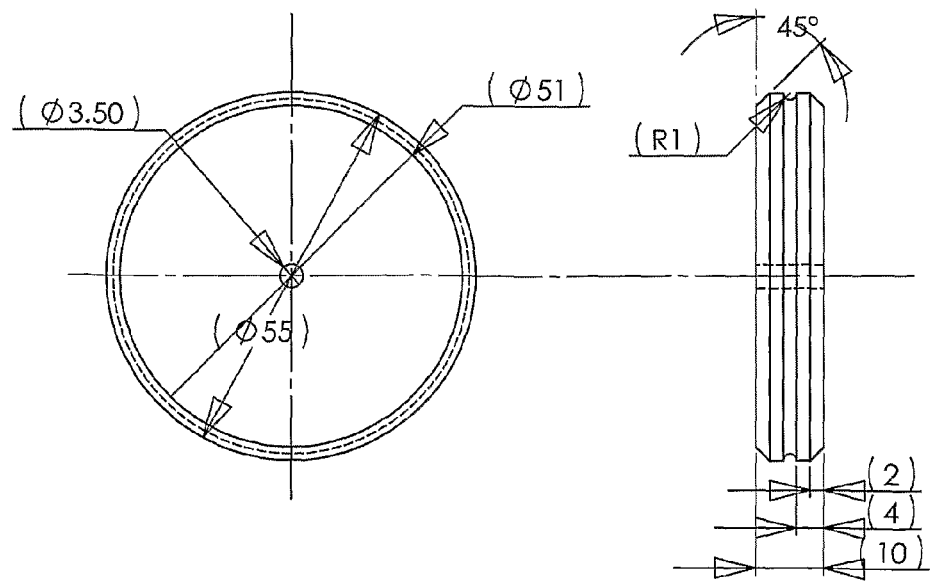

70% O₂
5% CO₂
25% N₂

Air mixture into incubator

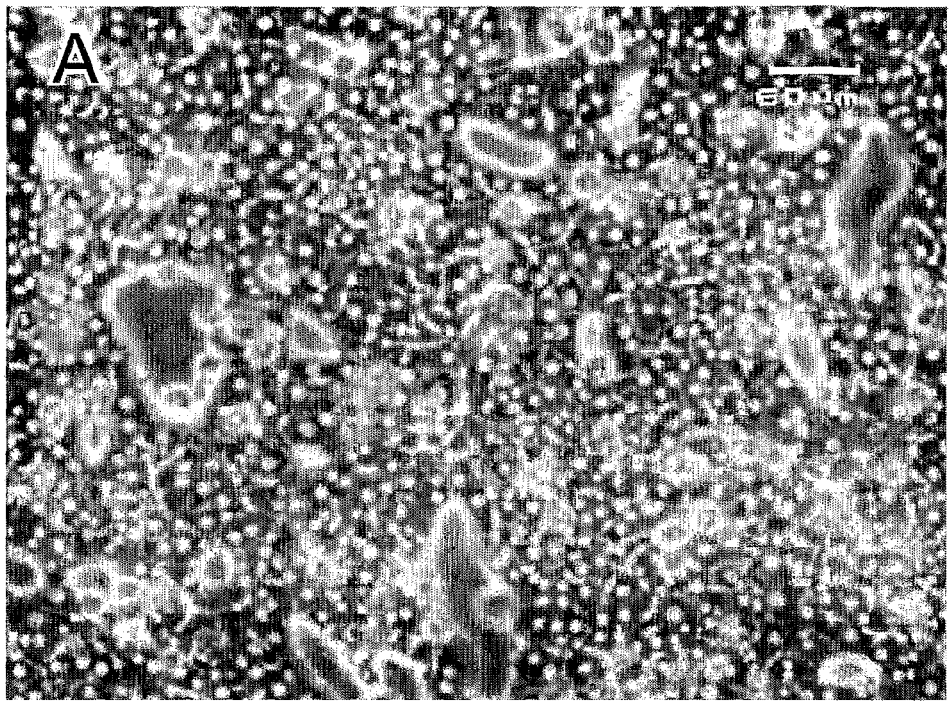
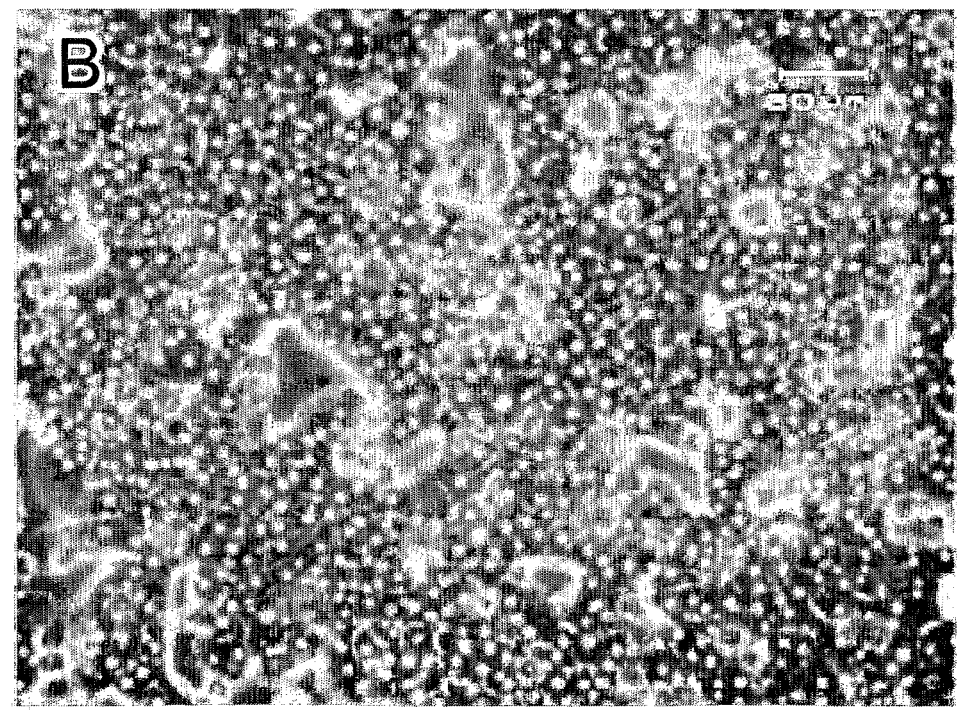
Fig. 9 (cont. on next page)

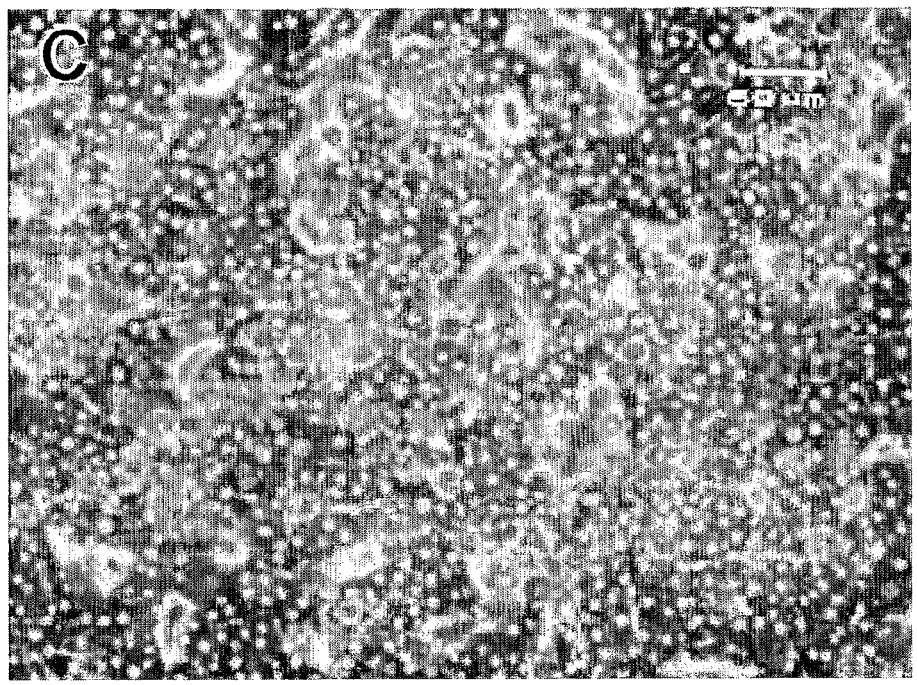
Fig. 9 (cont. from prev. page)
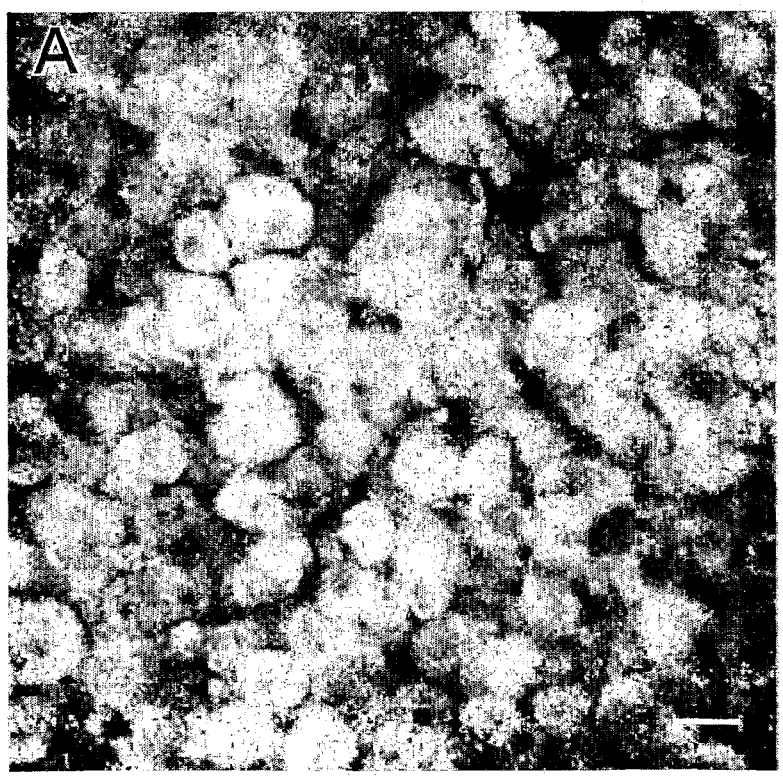
Fig. 10 (cont. on next page)

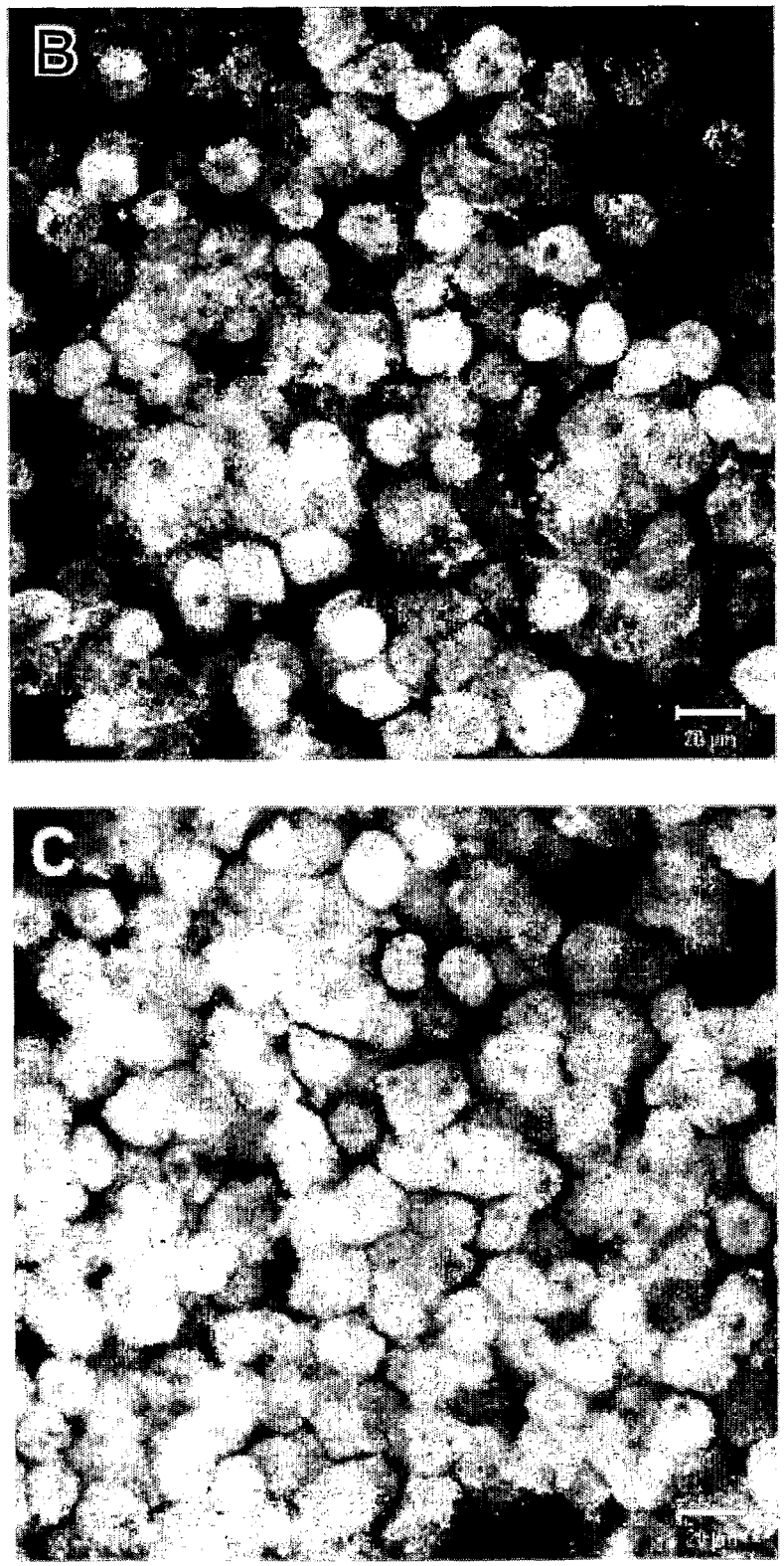
Fig. 10 (cont. on next page)

Fig. 10 (cont. from prev. page)

| Flowrate (mL/min) | WSS$_{Ave}$ (Pa) | WSS$_{Max}$ (Pa) |
|---|---|---|
| 1 | 0.002 | 0.005 |
| 5 | 0.010 | 0.027 |
| 10 | 0.020 | 0.059 |

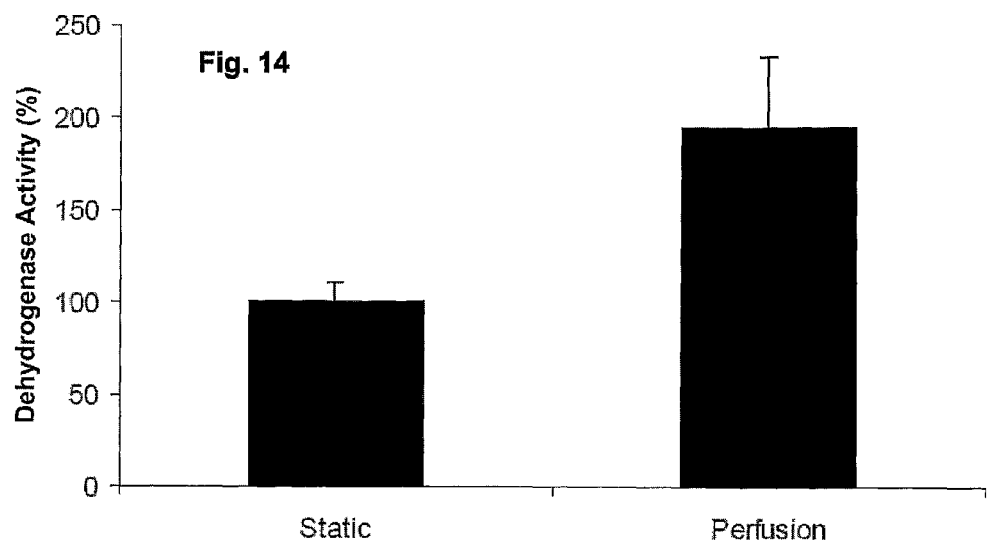
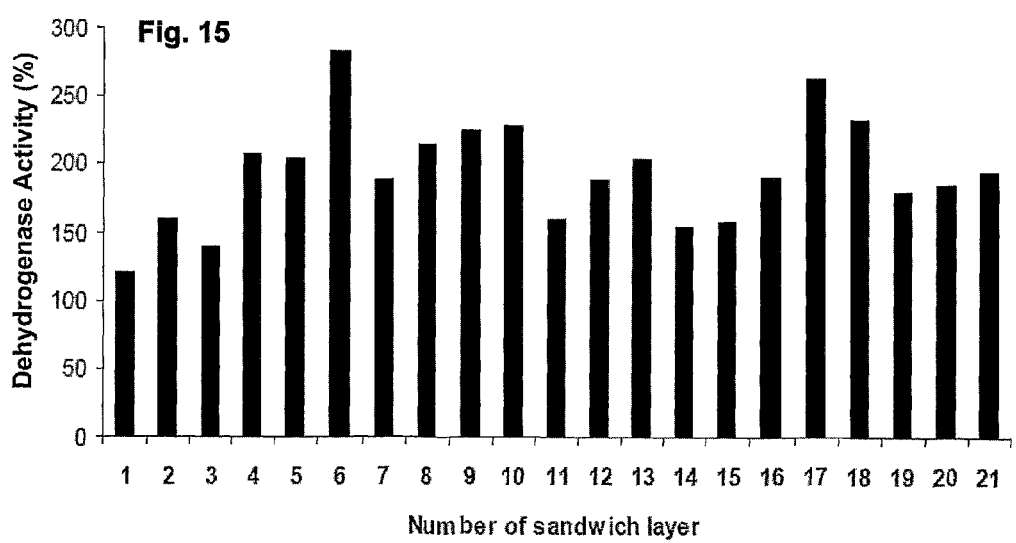

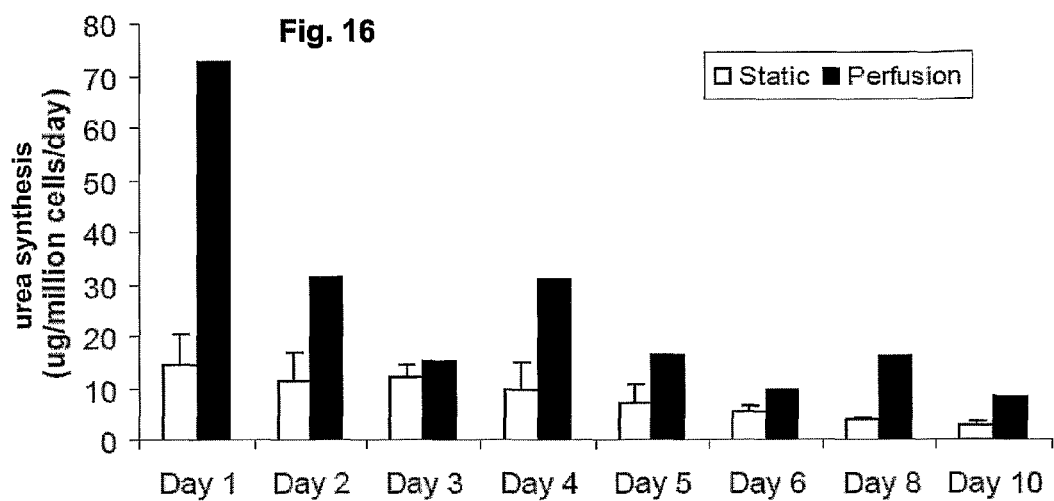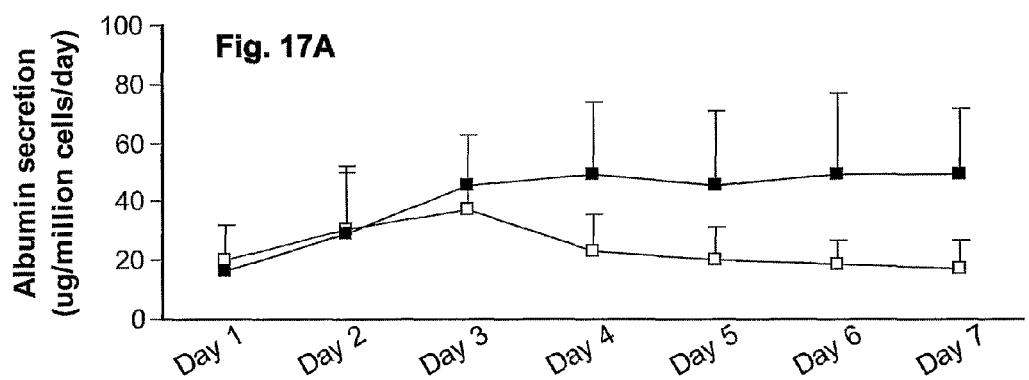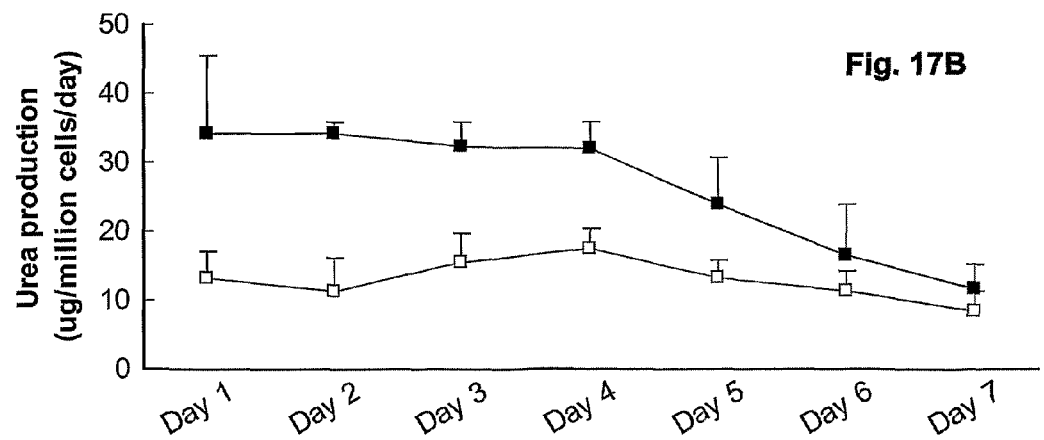

APPARATUS FOR CULTURING ANCHORAGE DEPENDENT CELLS

CROSS REFERENCE TO RELATED APPLICATIONS

This application makes reference to and claims the benefit of priority of a provisional application for a "Sandwich Culture Based Stack-Plate Hepatocytes Bioreactor" filed on Oct. 8, 2008 with the United States Patent and Trademark Office, and there duly assigned Ser. No. 61/136,838. The contents of said application filed on Oct. 8, 2008 is incorporated herein by reference for all purposes, including an incorporation of any element or part of the description, claims or drawings not contained herein and referred to in Rule 20.5(a) of the PCT, pursuant to Rule 4.18 of the PCT.

FIELD OF THE INVENTION

The present invention relates to an apparatus for culturing anchorage-dependent cells. One or more respective may be included in a cell culture system and be used as a liver assist device.

BACKGROUND OF THE INVENTION

Acute liver failure is a disease with a mortality of 60-90% depending on the cause, despite maximal supportive intensive care treatment. Even though liver transplantation remains the main curative option for patients suffering from acute liver failure, it is constrained by cost, donor scarcity and donor compatibility. A high incidence of patients with acute liver failure is dying on the transplantation waiting list. Artificial liver assist devices are particularly useful to sustain patients with acute and chronic liver failure that are awaiting liver transplantation or recovery/regeneration of their liver, but are ideally also capable of improving a patient's condition and converting patients from a non-transplantable to a transplantable state. Such devices ideally have to fulfil a variety of functions such as detoxification, regulation and synthesis of molecules in a manner resembling a healthy liver.

Devices for artificially providing liver functions can be grossly divided into non-biological and biological liver support. Early attempts of treating liver failure focused on non-biological means, using of hemodialysis and/or plasmapheresis for detoxifying the patient's blood through action of adsorption, filtration or centrifugation separation of the blood elements. Such approaches of developing non-biological liver support therapies have, however, yielded only limited or no success. The development of bio-artificial liver devices capable of supporting multiple liver specific functions began to gather speed as advances made in liver biology revealed the liver as a complex organ supporting multiple synthetic and metabolic functions. It thus became clear that replacement of a single hepatic function such as blood detoxification is not sufficient. Recent years have accordingly witnessed the advent of the bioartificial liver assist devices (BLADs) as a promising therapeutic for the treatment of acute liver failure. These BLA-type devices include mammalian cells and serve as an extracorporeal support for liver failure patients. Unlike a membrane-based liver dialysis system that provides passive detoxification treatment for patients with liver failure, BLADs set out to take over most if not all of the liver functions in the patient. This is achieved through the integration of isolated hepatocytes (liver cells) either of allogeneic or xenogeneic origin (e.g. porcine hepatocytes) with the ex vivo perfusion membrane-based bioreactors and perfused with either patients's plasma or blood. By using hepatocytes the BLAD not only performs blood detoxification but also provides liver-synthetic functions. Accordingly, the basic design consideration for BLADs is to ensure the maintenance of cell viability and functions with optimal control of nutrient and gases, coupled with metabolites exchanges, within the bioreactor cell culture.

Currently bio-artificial liver support systems of several alternative designs are either under development or undergoing pre-clinical/clinical trials. These BLADs can be classified into four basic designs according to the method of cells immobilization and the mode of perfusion used: 1) semi-permeable hollow fiber membranes, 2) encapsulations, 3) flatbed, and 4) perfused bed or scaffolds. In these configurations, the cells can be immobilized by Means of a microcarrier or be seeded in a collagen gel matrix or polymeric scaffold to form a 2D or 3D culture. Among the numerous BLAD designs, the hollow-fiber based liver support system, has been the most intensively studied and reviewed. Hollow fiber based BLAD configurations provide the ease of scaling up and the cells embedded within the hollow fiber are protected from the direct effect of the fluid shear as a result of the semi-permeable hollow fiber membrane. Certain difficulties nevertheless remain with this architecture, such as achieving uniform cell distribution within the luminal or capillary spaces of the hollow fiber and an inadequacy of the oxygen supply to the cell surfaces. The latter problem leads to the buildup of the non-physiological gradients in the bioreactor. In addition, hepatocytes are polarized cells and the liver specific functions are highly depends on cell polarity. During isolation, hepatocytes quickly lose their functions since cell polarity is disrupted. The lack of a cellular microenvironment to re-establish hepatocyte polarity in these configurations results in the deterioration of hepatocyte in vitro functions, thereby compromising the effectiveness of these BLADs.

An alternative architecture used is the flatbed bioreactor, mostly based on monolayer or sandwich culture. Such a design generally provides better control in terms of the uniformity of cell distribution and the regulation of micro environments mimicry of that found in vivo. Hepatocytes seeded as a monolayer on a substrate such as a collage gel form good cell-cell interaction as well as cell-matrix interaction. In the sandwich culture, the overlay of another collage gel layer on the top of the monolayer further stabilizes the structure. Hepatoycte polarity is re-established in sandwich culture, characterized by the exhibition of tight and gap junction, the formation of bile canalicular network, and the localization of sinusoidal and biliary transporters on the cell membrane, so that in vitro hepatocyte functions can be long-term maintained. Difficulties arising with this flatbed architecture include dead volume, regulation of the shear stress level on the cell surfaces, scalability of the bioreactor or low surface area to volume ratio. These problems have not been adequately addressed in many existing designs.

Thus on a general basis, the major drawback for many of the BLADs currently undergoing preclinical and clinical trials is the long-term maintenance of cell viability and functions as a result of inadequate cellular microenvironment and bidirectional mass transport. Indeed, research has shown that these bioreactors suffer from the rapid decline of cell functions due to poor maintenance of microenvironment cues, the inefficiency of nutrients and gas transport, and the inadequacy of the removal of accumulated toxic metabolites from the cells.

Accordingly it is an object of the present invention to provide a device or apparatus that overcomes at least some of these drawbacks. This object is solved by providing an apparatus according to claim 1.

SUMMARY OF THE INVENTION

The apparatus of the present invention may be termed a perfusion bioreactor. It may also be used as a module in a cell culture system, which may also be termed a bioreactor system. The apparatus is based on the sandwich culturing technique. When included in a cell culture system, such system may include a plurality of apparatuses, e.g. slotted onto a supporting platform. In short, an apparatus of the invention includes multiple stacked tissue culture plates, in which each plate is arranged at a distance from the next plate. Each plate is designed to have one cell culture or two sandwich cell cultures. Each plate may have a sleeve which may consist of an upper and a lower portion. Each plate may for instance have one or 2 interlock O rings used to secure 2 sandwich cell cultures. The final assembly may then have cell cultures on both top and bottom faces of the plate. A through-hole such as a slit is arranged at an outer end of each plate so that during the placements of the plates into the cylindrical culture chamber, the through-hole of each plate is placed distal, in particular at least directly opposite, those of its adjacent partners. This placement configuration allows the serial flow of culture media through each sandwich culture plate within the apparatus. This configuration ensures the optimal supply of nutrients and gases, at the same time allowing the removal and exchanges of metabolites, to and from the cell culture surfaces, thereby ensuring the long term cellular viability and functionality of a corresponding bioreactor.

In a first aspect the present invention provides an apparatus for culturing anchorage dependent cells. The apparatus includes a housing. The housing has an inlet and an outlet. Further, the housing has a circumferential wall, a base and a top wall. The base includes the inlet and the top wall includes the outlet. The circumferential wall of the housing defines a longitudinal axis of the housing. The circumferential wall of the housing also defines an inner cross section in a plane perpendicular to the longitudinal axis. The inner cross section defined by the circumferential wall of the housing has a shape and dimensions that are at least essentially uniform along the longitudinal axis of the housing. The apparatus also includes a plurality of culture plates. The culture plates are removably arranged within the housing. The culture plates are stacked within the housing. The culture plates of the plurality of culture plates are arranged at least essentially parallel to each other within the housing. In some embodiments each culture plate of the plurality of culture plates is at least essentially arranged in the plane of the inner cross section that is defined by the circumferential wall of the housing. Each culture plate is mounted and sealed to the circumferential wall of the housing. Furthermore, each culture plate is arranged at a distance from an adjacent culture plate; that is the culture plates are arranged in the direction of the longitudinal axis of the housing at a distance from each other. Each culture plate has a through hole. As a result the inlet and the outlet of the housing are in fluid communication. The through hole of each culture plate is positioned at an outer end of the culture plate, proximate the circumferential wall of the housing. The through holes of adjacent culture plates are distally positioned in the plane defined by the at least essentially parallel arrangement of the culture plates. In some embodiments this plane corresponds to the plane of the inner cross section of the housing.

In a second aspect the present invention provides a cell culture system for culturing anchorage-dependent cells. The cell culture system includes a plurality of apparatuses according to the first aspect. The plurality of apparatuses is removably positioned by a scaffold or by a housing. The apparatuses are positioned to allow a parallel connection of the inlets of the apparatuses to a feeding conduit.

In a third aspect the present invention provides a method of culturing anchorage-dependent cells. The method includes providing a plurality of culture plates. Each culture plate has an upper face and a lower face. The upper face and the lower face of each culture plate are arranged at least essentially parallel to each other. All of the culture plates have upper faces and lower faces of at least essentially identical shape and dimensions. Accordingly, the upper face of each of the culture plates has a shape that is at least essentially identical with the shape of the upper face of each other culture plate of the plurality of culture plates. The upper face of each of the culture plates also has dimensions that are at least essentially identical with the dimensions of the upper face of each other culture plate of the plurality of culture plates. Likewise, the lower face of each of the culture plates has a shape and dimensions at least essentially identical with the shape and dimensions of the lower face of each other culture plate of the plurality of culture plates. Furthermore each culture plate has a through hole. Each through hole is positioned at an outer end of the culture plate, being positioned contiguous the circumference of the culture plate. The method further includes seeding anchorage-dependent cells in the plurality of culture plates. The method also includes providing a housing. The housing includes a circumferential wall, a base and a top wall. The base includes an inlet. The top wall includes an outlet. The circumferential wall of the housing defines a longitudinal axis of the housing. The circumferential wall also defines an inner cross section in a plane perpendicular to the longitudinal axis of the housing. The inner cross section defined by the circumferential wall of the housing has a shape and dimensions that are at least essentially uniform along the longitudinal axis of the housing. The method also further mounting the plurality of culture plates stacked into the housing. The plurality of culture plates are mounted into the housing such that the culture plates are sealed to the circumferential wall of the housing. The plurality of culture plates are also mounted into the housing such that the culture plates are arranged at least essentially parallel to each other. Each culture plate is thereby arranged at a distance from an adjacent culture plate. The plurality of culture plates are further mounted into the housing such that the through holes of adjacent culture plates are distally positioned in the housing in the plane defined by the at least essentially parallel arrangement of the culture plates. In some embodiments this is the plane of the inner cross section of the housing.

BRIEF DESCRIPTION OF THE DRAWINGS

The invention will be better understood with reference to the detailed description when considered in conjunction with the non-limiting examples and the accompanying drawings.

FIG. 4 depicts an example of a cell culture system (3) according to the invention, which may be a hepatocytes bioreactor. The system includes four apparatuses (1) of the invention. FIG. 4E depicts the dimensions of a circumferential wall (7) of a housing of an apparatus in top view and side view. FIG. 4G depicts the dimensions of a bearing holder (50) of the housing of an apparatus in top view and side view. FIG. 4H depicts the dimensions of a bottom plate (41) of the cell culture system in top view and side view. FIG. 4J depicts the dimensions of a side plate (43) of the cell culture system in top view and side view. FIG. 4L depicts the dimensions of a motor rod (46) of the cell culture system in top view and side view. FIG. 4M depicts the dimensions of a roller (40) of the cell culture system in top view and side view.

FIG. 9 shows three phase-contrast photomicrograph visualizations of hepatocytes present on different regions of a PET film of a diameter of 5 cm, defining a central face of a culture plate in an apparatus of the invention. Photomicrographs were taken after 24 hours of pre-perfusion static stabilization in a 5% $CO_2$ incubator. Shown are cells on the center region (A), on the region between center and peripheral (B) and on the peripheral region (C) of the PET film. A white bar placed on each photo represents 50 µm.

FIG. 10 depicts confocal microscopy visualizations of hepatocytes present in a culture plate of an apparatus of the invention after 10 days of perfusion at 2.12 mL/min as compared to the static culture. Cells at different locations (B-D) within the apparatus are shown. Static culture (A), a bottom layer in perfusion culture (B), a middle layer in perfusion culture (C), and a top layer in perfusion culture (D); Nuclei of dead cells (red) with live cells (green) counter-staining. Depicted is the green channel of the recorded image, represented as white. Red channel representations resulted in black images. The white bar placed on each photo represents 20 µm.

FIG. 14 shows the dehydrogenase activity (%) of the hepatocytes culture within an apparatus of the invention in comparison to the static Culture after 10 days as monitored by the MTS assay.

FIG. 15 shows the dehydrogenase activity of the hepatocytes culture in each of the individual sandwich culture plates in the apparatus of the invention after 10 days as monitored by the MTS assay.

FIG. 16 depicts the daily urea synthesis rates of the perfusion culture using an apparatus of the invention as compared to those of the static culture over a period of 10 days.

DETAILED DESCRIPTION OF THE INVENTION

Figure 1A:
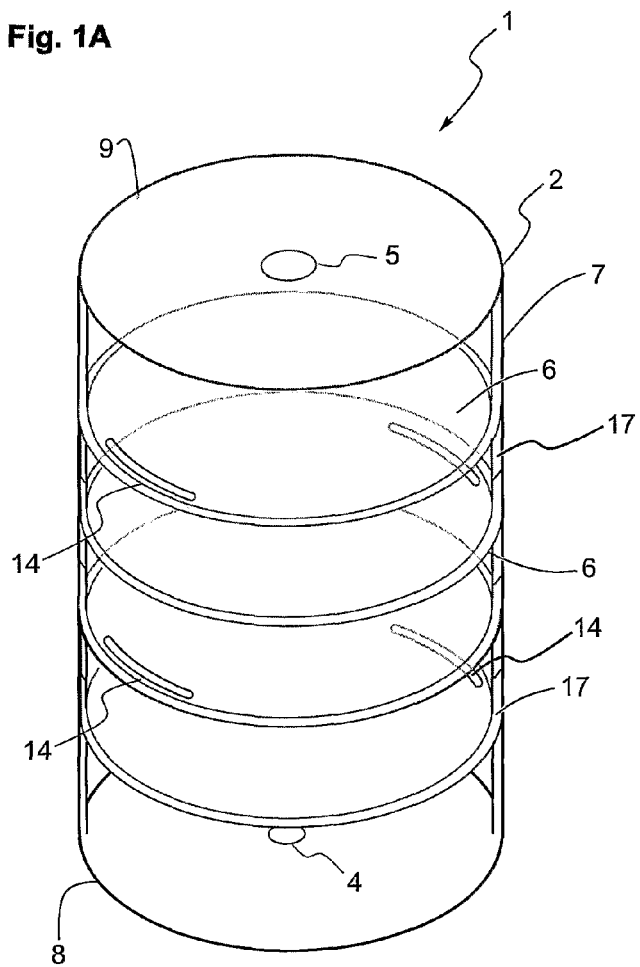
FIG. 1A depicts an embodiment of an apparatus (1) of the invention. A housing (2) with a circumferential wall (7), a base (8) and a top wall (9) includes a plurality of culture plates (6) that are stacked in parallel. An inlet (4) in the base (8) is in fluid communication with an outlet in the top wall (9) via through holes (14) in the culture plates (6). Each culture plate (6) has a sleeve (17), which establishes a seal with the circumferential wall (7) of the housing (2).
Figure 1B:
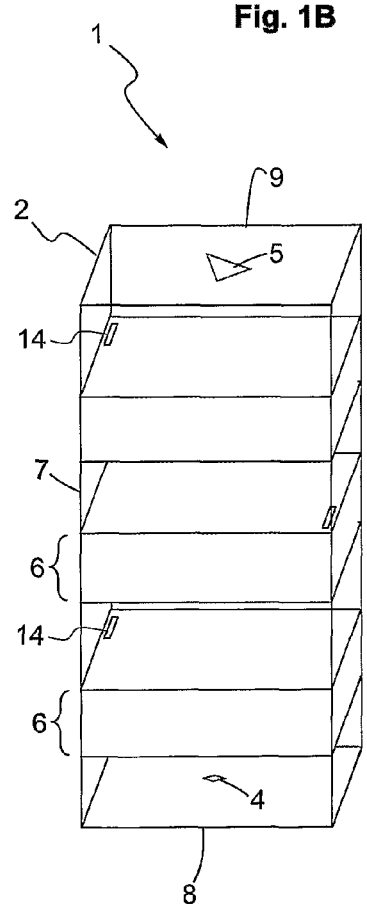
FIG. 1B depicts a further embodiment of an apparatus (1) of the invention. A housing (2) has a circumferential wall (7), a base (8) and a top wall (9). A plurality of culture plates (6) is stacked within the housing (2). An inlet (4) in the base (8) is in fluid communication with an outlet (5) in the top wall (9) via through holes (14) in the culture plates (6).
Figure 1C:
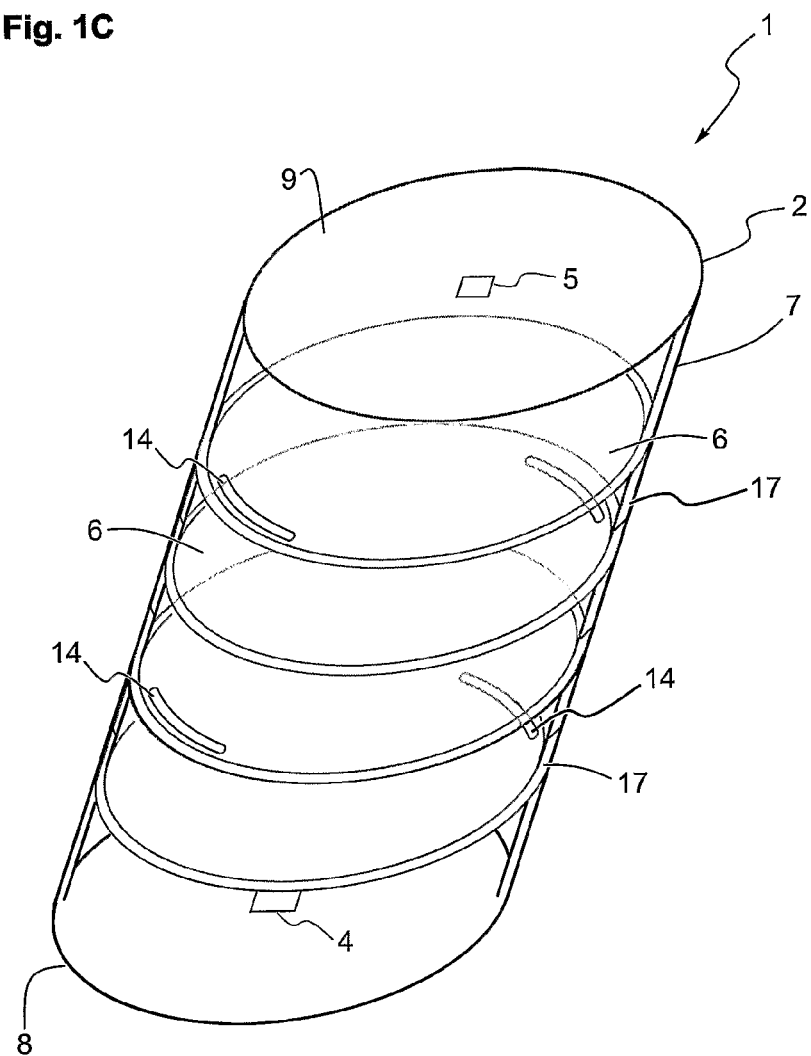
FIG. 1C depicts yet a further embodiment of an apparatus (1) of the invention. The housing (2) has a circumferential wall (7) that is inclined with regard to the base (8), the top wall (9) and the level in which the plurality of culture plates (6) is arranged in the housing (2). An inlet (4) in the base (8) and an outlet (5) in the top wall (9) are in fluid communication since a through hole (14) is arranged in each of the culture plates (6).

The present invention provides an apparatus that allows for a bioreactor design that is based on sandwich culture configuration. The apparatus addresses some of the persistent problems faced by the existing BLAD prototypes, namely the supply of adequate oxygen to cell surfaces, the regulation of fluid shear on the cell surfaces, and the ease of scalability of the bioreactor. The apparatus may in some embodiments be designed as a cylindrical culture chamber, as further explained below. The apparatus may be included in a system with a mounting platform, which has the capacity for simultaneously perfusing a plurality of apparatuses, for example up to four apparatuses. An apparatus of the invention has a stack of culture plates. In some embodiments this design provides a stack of culture plates having sandwich cultures on both sides of each plate. The design of the apparatus of the invention ensures the serial flow of culture medium through the respective apparatus, including a corresponding system that includes several apparatuses, and promotes longer residence time for the exchanges of metabolites and transport of essential gases and nutrients to the cell surfaces. The inventors found that the apparatus was able to maintain hepatocyte function over a period of 10 days. These results demonstrated that apparatus of the present invention is capable of maintaining long-term in vitro functions of the hepatocytes.

An apparatus for culturing anchorage-dependent cells according to the present invention includes a housing with a circumferential wall. The circumferential wall may include any desired material. Typically, it is solid and able to remain intact during the entire culturing process to be performed therein. As a few illustrative examples, the circumferential wall, or a portion thereof, may include glass, polypropylene (PP) or polytetrafluoroethylene (PFTE, Teflon). In some embodiments at least a portion of the circumferential wall, the base and/or the top wall is of matter that allows light to enter into the culture chamber. The term "light" is understood to include electromagnetic radiation of any wavelength, including a distinct wavelength, a set of distinct wavelengths or any region of the electromagnetic spectrum. Two examples of a region of the electromagnetic spectrum are visible light, corresponding to a wavelength range of about 400 to about 700 nanometers, and ultraviolet light, corresponding to a wavelength range of about 30 to about 400 nanometers. In some embodiments at least a portion of the circumferential wall, the base and/or the top wall is of matter that allows light to emerge from the culture chamber. A respective wall (including base) portion that allows light to emerge may be identical to, overlapping with or different from a wall portion (including a base) that allows light to enter the culture chamber. A wall portion may for instance be transparent or translucent. Examples of suitable material for a wall portion that allows light to pass include, but are not limited to, glass, quartz and plastic material. Suitable plastic materials for the construction of a respective wall portion include, but are not limited to, polymethyl-methacrylates (e.g. polymethyl-methacrylate (PMMA) or carbazole based methacrylates and dimethacrylates), polystyrene, polycarbonate, and polycyclic olefins. A further illustrative example of a material that is additionally suitable for the generation of a wall portion that allows light to pass only to a certain extent is fluoro-ethylen-propylen (FEP).

The circumferential wall may be of any thickness/strength, as long as it capable of remaining at least essentially intact during the culture of cells therein. Accordingly, the geometry of the outer shape of an apparatus of the invention may differ from the geometry of the culture chamber, its interior defined by the circumferential, the base and the top wall.

The inner and outer faces of the circumferential wall may also possess any internal surface characteristics, as long as they allow the storage of a medium, in particular a liquid. The circumferential wall of the housing may be of any geometry as long as it fulfils two conditions. Firstly the circumferential wall, or at least the inner face thereof, needs to have such a degree of symmetry that it defines a longitudinal axis of the housing. Secondly, at any desired position the circumferential wall defines an inner cross section, or inner transverse section, in a plane perpendicular to the longitudinal axis. This inner cross section is defined by the distances between opposing portions of the inner faces of the circumferential wall. This inner transverse section needs to be of a shape and of dimensions that are at least essentiallly uniform along the longitudinal axis of the housing. Accordingly, at any desired position on the circumferential wall, the inner face of the circumferential wall defines a transverse section that is at least essentially identical to the transverse section defined by the inner face of the circumferential wall at any other position on the circumferential wall. These requirements are for instance not fulfilled by an ellipsoid, while they are fulfilled by a cylinder or the circumference of a cuboid.

Besides these requirements the inner cross section of the housing may have any desired profile, such as ovoid shape, the shape of a circle, an egg, letters V or U, a triangle, a rectangle, a square, or any polyhedron. Hence, in one embodiment where the base and the top wall of the housing are arranged parallel to each other the housing defines an at least essentially cylindrical interior. Typically, the maximal distance spanning the inner cross section, i.e. its maximal width, is selected within the range of about 1 centimeter to about 2 meters, about 2 centimeters to about 1 meter or about 2 centimeters to about 50 centimeters, such as about 2 centimeters to about 25 centimeters, about 4 centimeters to about 25 centimeters, about 2 centimeters to about 15 centimeters, about 4 centimeters to about 15 centimeters, about 2 centimeters to about 10 centimeters or about 3 centimeters to about 10 centimeters. In one embodiment the maximal width is about 6 cm, e.g. 5.8 cm.

The circumferential wall may be of any height in the direction of its longitudinal axis. The height may in some embodiments be selected in the range from about 1 centimeter to about 2.5 meters, about 2 centimeters to about 1 meter, about 2 centimeters to about 1.5 meters or about 2 centimeters to about 1 meter, such as about 2 centimeters to about 75 centimeters, about 5 centimeters to about 75 centimeters, about 2 centimeters to about 50 centimeters, about 4 centimeters to about 50 centimeters, about 3 centimeters to about 40 centimeters, about 5 centimeters to about 30 centimeters, about 5 centimeters to about 20 centimeters or about 10 centimeters to about 20 centimeters. In one embodiment the height is about 14 cm.

The housing of the apparatus further includes a base and a top wall. Both the base and the top wall may be of any inner and outer geometry and include any desired material. The base and the top wall may for instance be curved, round, straight or flat. They may be arced, such as concave or convex, undulated, or include a dent, a nook or any other geometrical element. In typical embodiments both the base and the top wall are solid and able to remain intact during the entire culturing process to be performed therein. Any one of the base, the circumferential wall and the top wall may be a part of another, typically larger, wall or base, respectively. The base and the top wall of the housing may be of any desired material. In some embodiments the base, the top wall and the circumferential wall of the housing include one or more identical material(s). In one embodiment the base, the top wall and the circumferential wall of the housing are made of the same material(s). The base and the top wall may be arranged at any desired orientation with regard to each other. In some embodiments one or both of the base and the top wall of the housing are arranged at least essentially perpendicular to the longitudinal axis defined by the circumferential wall of the housing. In one embodiment the base and the top wall of the housing are arranged at least essentially parallel to the plane of the inner cross section of the circumferential wall thereof.

The inner faces of this circumferential wall, of the base and of the top wall define a culture chamber. The interior of the culture chamber means any space or matter that is in direct contact with fluid filled into the culture chamber while any inlets or outlets, e.g. openings, are sealed. It also refers to any space or matter that may be included in space or matter contacting such fluid. Accordingly the term "inner face", when used in connection with the culturing chamber, refers to surface areas that face the interior of the culturing chamber in that they are able to contact fluid filled therein, in particular while any opening is sealed. The culturing chamber is then capable of receiving a fluid and/or a sample, e.g. a suspension of cells, blood or plasma, as well as optionally further matter. Hence, in some embodiments the culture chamber is filled with a medium, for instance an aqueous medium for culturing cells, such as one of the well known cell culture media ("growth media") available in the art, e.g. LB medium; a monosaccharide containing liquid—possibly including e.g. Hank's Salts; Eagle's minimal essential medium (including e.g. Dulbecco's Modified Eagle Medium); RPMI (Roswell Park Memorial Institute) medium; HyClone medium; Ham's tissue culture medium; Chee's medium; Y M Broth; or Murashige and Skoog medium, to name a few, or blood. In other embodiments it may be desired to fill the culturing chamber with such medium in order to culture cells or to detoxify the medium by means of cells present in the culturing chamber.

The culture chamber defined by the circumferential wall, the base and the top wall of the housing may be designed to be capable of accommodating any desired fluid. The fluid may be of any properties, whether polar or non-polar. Typically the fluid is an aqueous liquid such a cell culture medium, blood or plasma. Through the inlet in the base the fluid may be disposed into, or enter, the sample compartment. Through the outlet in the top wall the fluid may exit the culture chamber.

Within the interior of the culture chamber there may be provided further elements such as one or more sensors, e.g. for detecting temperature or oxygen levels, or one or more oxygen support elements. Oxygen support elements may for example be designed to include capillaries that are in fluid contact with an external oxygen supply. Such elements are in direct contact with fluid filled into the culture chamber and are thus included in the interior of the culture chamber. Further matter in communication with such elements, such as tubing or wiring, is however typically not in direct contact with fluid filled into the culture chamber and thus not part of the interior of the culture chamber.

The culture chamber defined by the inner faces of this circumferential wall, the base and the top wall may be of any volume. The volume may in some embodiments be selected in the range from about 0.01 to about 3000 liters, 0.1 to about 3000 liters, about 0.05 to about 1000 liters, about 0.2 to about 1000 liters, about 0.1 to about 500 liters, about 0.25 to about 500 liters, about 0.1 to about 100 liters, about 0.5 to about 100 liters, about 0.2 to about 50 liters, about 0.5 to about 50 liters, about 0.25 to about 20 liters, about 0.5 to about 20 liters, about 0.5 to about 10 liters, about 0.5 to about 5 liters, about 0.1 to about 5 liters, about 0.25 to about 2.5 liters, about 0.5 to about 2 liters, about 0.5 to about 1.5 liters or about 1 to about 2 liters. In one embodiment the volume is about 1.5 liters.

The circumferential wall, the base and the top wall as such thus act to prevent any communication between fluid filled into the chamber and the surrounding environment. Generally the base and the top wall thus prevent any fluidic communication between the interior of the chamber and the surrounding environment. Elements such a sensor or an oxygen support element are designed to prevent fluid communication with the interior of the chamber by means of a membrane or one or more walls. Where an oxygen support element has a membrane via which a fluid such as a gas is permitted to contact fluid filled into the chamber and to dissolve therein, any direct communication between the respective fluids is prevented by the barrier provided by the membrane. The term "fluid communication" is accordingly understood not to include diffusion or osmosis across a barrier. Any inlets or outlets that such elements may have, for instance in order to allow supply with a fluid, are accordingly neither in fluid communication with fluid filled into the chamber and thus not part of the interior of the chamber.

As explained above, the base has, however an inlet and the top wall has an outlet. Via the inlet and the outlet—and generally only via the inlet and the outlet, since no additional inlets or outlets are generally present—the interior of the culture chamber is in contact with the environment. Independent from one another the inlet and the outlet may consist of or may include any means. Each of them may for instance be an opening, a channel or a valve. A respective opening, as well as the profile of a respective channel, may be of any size and shape. Examples include, but are not limited to, the shape of a circle, rectangular or square shape or the shape of a triangel. In some embodiments the inlet and or the outlet of the housing of the apparatus may be entirely sealable.

Within the housing of the apparatus there is further included a plurality of culture plates. The culture plates may include any desired material. Typically, it is solid and able to remain intact during the entire culturing process to be performed therein. The above said with regard to the properties and requirements circumferential wall of the housing applies mutatis mutandis to the culture plates as a whole as well as to elements and portions defining an outer surface of the culture plate. There is thus for example no fluid communication between the inlet and the outlet of the housing across a culture plate, except for a through hole present therein. The culture plates are removably arranged in the housing. They are stacked in that they are arranged at least essentially parallel to each other. These plates may be of identical dimension and located in positions exactly on top of each other. In such embodiments each culture plate is at least essentially arranged in the plane of the inner cross section defined by the circumferential wall of the housing. Hence, a first plane defined by the at least essentially parallel arrangement of the culture plates and a second plane of the inner cross section defined by the circumferential wall of the housing are in these embodiments at least essentially identical. In other embodiments these two planes, i.e. the plane defined by the at least essentially parallel arrangement of the culture plates and the plane of the inner cross section defined by the circumferential wall of the housing are arranged in an angle of inclination with regard to each other. This angle may be selected in a range from 0 to 90 degrees. Typically this angle is selected in a range from 0 to about 45 degrees. It may for instance be selected in a range from 0 to about 40 degrees, in a range in a range from 0 to about 45 degrees, from 0 to about 30 degrees, from 0 to about 20 degrees, from 0 to about 15 degrees, from 0 to about 10 degrees or from 0 to about 5 degrees. Accordingly, in some embodiments the plates are arranged offset with regard to the plane defined by their parallel arrangement to each other.

The culture plates are arranged in the housing at a distance from each other. Each of the plurality of culture plates is accordingly arranged at a distance from an adjacent culture plate. In typical embodiments the distance between adjacent culture plates may be selected in the range from about 0.25 mm to about 5 mm, such as about 0.35 mm to about 3 ram, about 0.5 mm to about 2 mm or about 0.75 mm to about 1.5 mm. In one embodiment the distance between adjacent culture plates is about 1 mm. The distance between any two adjacent culture plates may be different from the distance between any two adjacent culture plates. In some embodiments the distance between any adjacent culture plates is independently selected in the range from about 0.25 mm to about 5 mm, e.g. about 0.35 mm to about 3 mm or about 0.5 mm to about 2 mm. In some embodiments the distances between two adjacent culture plates, at least within a selected region of more than three culture plates, differs by no more than 0.5 mm, no more than 0.2 mm, no more than 0.1 mm, no more than 0.05 mm or no more than 0.01 mm. In one embodiment the distance between adjacent culture plates is at least substantially uniform.

The culture plates are mounted to the circumferential wall of the housing. This may be achieved by a mechanical fastening such as a fixture included in the circumferential wall of the housing of the apparatus. As an illustrative example, the culture plates may snap in place if arranged in the housing. In some embodiments the culture plates may be in physical contact with the circumferential wall of the housing without any further anchorage or fixing that would achieve a locking connection between housing and plates. In such embodiments the plurality of culture plates is simply stacked by using one or more element or device(s) that serve(s) as a spacer, providing a distance between adjacent culture plates (cf. also below). Due to the matching outer dimensions of the culture plates with regard to the inner cross section of the housing of the apparatus each culture plate is fitted within the circumferential wall of the housing. Since the inner cross section defined by the circumferential wall of the housing has a shape and dimensions that are at least essentially uniform along the longitudinal axis thereof, culture plates are positionable in an interchangeable way. Any culture plate can be arranged at any position within the housing of the apparatus. Thus a selected culture plate can also be moved from one position in the housing to another position.

Each culture plate is sealed to the circumferential wall of the housing. In some embodiments the shape and dimensions of one or more, including each culture plate are designed to define an at least essentially fluid-tight seal with the circumferential wall of the housing. A seal may for instance be selected to be sufficient tight to allow enclosure of fluid in the space between adjacent culture plates. The seal may be achieved by a sufficiently accurate match of the inner dimensions of the circumferential wall of the housing and the circumference of the culture plates. In some embodiments the seal may be achieved by an appropriate selection of a flexible material to be included in the circumferential wall of the housing and/or in the culture plates. In some embodiments additional matter in form of a sealing means may be arranged within the housing such as a gasket, e.g. an O-ring. Such sealing means may be of any suitable rigid or semi-rigid material. In some embodiments a sealing material may be applied to provide a desired tight seal, e.g. a sealing fluid in form of e.g. a gel or a liquid, which may harden to form or to maintain a tight seal. As an illustrative example a sealing material may include a polymer that is derived from a photosensitive and/or heat-sensitive polymer precursor. Thus, the sealing material may be formed from a respective precursor after positioning it at the contact face between the circumferential wall of the housing and the circumference of the culture plates, by polymerisation. A corresponding sealing process may be of reversible or irreversible nature. As an example, without oxidative treatment PDMS forms a non-covalent reversible seal with smooth surfaces. A respective sealing may in some embodiments be performed by a glue. Any glue that is compatible with the desired use of the apparatus in culturing cells may be used.

The culture plates have an upper face and a lower face. In typical embodiments there is an inner distance within the culture plate between the upper face and the lower face thereof, once included in the housing. Hence, in some embodiments the upper face, the lower face and the circumferential wall of the housing of the apparatus define an interior space of the culture plate, which may be taken to define a compartment. In some embodiments the culture plate has a sleeve around its circumference, defining a circumferential wall. Once included into the housing of the apparatus such a circumferential wall of the culture plate has an orientation that corresponds to the circumferential wall of the housing. Generally such a circumferential wall of the culture plate is in mechanical contact with the circumferential wall of the housing. It may for instance form a seal with the circumferential wall of the housing. In this regard the circumferential wall of the culture plate may be designed to match the cross section of the circumferential wall of the housing, such that the culture plate is fitted within the circumferential wall of the housing. In such embodiments the upper face, the lower face and the circumferential wall of the culture plate define an interior space of the culture plate. It is understood that adjacent culture plates are positioned within the apparatus such that a first culture plate and an adjacent second culture plate can be arranged with the first culture plate being positioned below the second culture plate. Hence the upper face of a respective first culture plate is in abutment to the lower face of a respective second culture plate.

As noted above, both the upper and the lower face of each culture plate may include, as well as be of, any desired material, as long as the material prevents a fluid coupling between inlet and outlet of the housing. In some embodiments at least one of the upper and the lower face of at least one culture plate is porous, for instance microporous or nanoporous. In some embodiments at least one of the upper and the lower face of each culture plate is porous, for instance microporous or nanoporous. In one embodiment each upper face and each lower face, i.e. each of the upper and the lower faces of each culture plate are porous. In some embodiments the upper and/or the lower face of one or more, including each, cell culture plate(s) includes or consists of a porous, e.g. nanoporous semi-rigid layer that permits ions, small proteins, metabolites, gases dissolved in the medium, such as oxygen, to pass. In such embodiments cells may be arranged behind a corresponding upper and/or lower face, or a respective portion thereof (cf. also below). The cells may accordingly be arranged within the cell culture plate, at the inner side of the upper and/or lower face thereof. The cells may also be arranged behind an anchorage substrate that allows ions, small proteins, metabolites, or gases to pass, thereby reaching the cells. In the latter case the anchorage substrate may be, at least to a certain extent, arranged between the upper and/or the lower face of the cell culture plate and the cells included therein. In either of these cases the semi-rigid layer is capable of protecting the cells to a large extent from the effects of shear stress. Shear stress is for example not typically encountered by hepatocytes in vivo, since in the liver they are shielded by a layer of sinusoidal endothelial cells from the direct shear of the blood flow.

The interior of a culture plate may be of any desired shape and dimensions as long as the desired cell type can be safely arranged within culture plate(s). With regard to the outer dimensions and shape of a culture plate it is however noted that the culture plate needs to be fitted to the circumferential wall of the housing. Accordingly, the selection of the inner dimensions of the housing in the plane of the cross section defined by the circumferential wall of the housing is also a selection of the outer dimensions of a matching culture plate in the same plane. This sets an upper limit to the interior with of the culture plate in the same plane. The interior of the culture plate may further be of any desired volume. The volume may in some embodiments be selected in the range from about 0.05 to about 500 milliliters, about 0.1 to about 500 milliliters, about 0.1 to about 200 milliliters, about 0.1 to about 100 milliliters, about 0.25 to about 100 milliliters, about 0.25 to about 50 milliliters, about 0.5 to about 50 milliliters, about 0.5 to about 25 milliliters, about 0.5 to about 15 milliliters, about 0.5 to about 10 milliliters, about 0.5 to about 5 milliliters or about 0.5 to about 2 milliliters. In one embodiment the volume of the interior of the culture plate is about 1 milliliter.

The terms "horizontal", "vertical", "below", "above", "lower", "upper", "top" and "on top" as used herein, refer to a position, where the apparatus of the present invention is oriented in such a way that the plane defined by the at least essentially parallel arrangement of the culture plates in the housing is oriented at least largely (if not at least substantially) perpendicular to the direction of the gravitational force of the earth. Typically this plane defined by the arrangement of the culture plates is at least roughly parallel to the ground. In this orientation the inlet of the apparatus is arranged, relatively to the culture plates, in the direction in which the gravitational force of the earth is acting. In such an orientation the outlet of the apparatus is arranged, relatively to the culture plates, in the direction opposite to the direction in which the gravitational force of the earth is acting. In this orientation the circumferences of the culture plates in the housing extend at least roughly about the direction of gravitational force of the earth. The culture plates are in this position oriented on top of each other. In typical embodiments, this position reflects an orientation of the apparatus, where the inlet of the housing is facing downward, and in which the apparatus can be placed onto a flat surface. In some embodiments the circumferential wall of the housing is arranged at least essentially perpendicular to the plane defined by the at least essentially parallel arrangement of the culture plates. In this case the circumferential wall of the housing extends, in an orientation defined here, at least essentially in the direction of the gravitational force of the earth. Typically the inner cross section defined by the circumferential wall of the housing is in this case arranged at least roughly parallel to the ground, i.e. the surface of the earth.

The upper face, the lower face and, if present, a central face may be of any inner and outer geometry and include any desired material. They may for instance be curved, round, straight or flat. They may be arced, such as concave or convex, undulated, or include a dent, a nook or any other geometrical element. It is noted in this regard that the parallel arrangement of surface elements such as dents may lead to the creation of swirls, which may require particular optimizations with regard to the maximal flow rate that the selected cells to be cultured in the apparatus can stand over extended periods (e.g. over a week or more). In typical embodiments both the upper face and the lower face, as well as, if present, a central face are at least essentially straight, including plain, faces that may be taken to define a straight wall. In some embodiments all three faces or both the upper face and the lower face are arranged in parallel.

The upper face and the lower face, if present a central face and a circumferential wall, e.g. a surface of a sleeve that faces the interior of the culture plate, may be of any desired surface properties and surface characteristics, such as surface morphology and structure. Any internal surface of the plate may thus be rendered polar and thus hydrophilic or non-polar and thus hydrophobic. Furthermore, different internal areas of inner surfaces may provide different surface characteristics. Thus, some surface(s) or surface areas within a culture plate such as a wall or wall-portion, may be rendered polar, while other areas may be rendered non-polar. Where desired, a treatment of a surface area of a plate of the apparatus or any other part of the apparatus may be carried out that achieves an alteration of surface characteristics. Such treatment may include any process that leads to an alteration of the respective surface characteristics that lasts long enough to maintain at least essentially or at least to certain degree, an altered surface characteristic upon subsequent contact with a fluid, possibly with a culture of cells. Typically, this treatment does not affect the composition of a fluid contacting the respective surface area. In some embodiments the treatment does not affect the composition of any fluid that contacts the respective surface area. In some embodiments the treatment does not alter the composition of a polar medium such as a polar fluid if filled into the interior of a respective plate(s) or into the apparatus.

A treatment that may be carried out to alter surface characteristics may include various means, such as mechanical, thermal, electrical or chemical means. A method that is commonly used in the art is a treatment with chemicals having different levels of affinity for the fluid sample. As an example, the surface of plastic materials can be rendered hydrophilic via treatment with dilute hydrochloric acid or dilute nitric acid. As another example, a polydimethylsiloxane (PDMS) surface can be rendered hydrophilic by an oxidation with oxygen or air plasma. Alternatively, the surface properties of any hydrophobic surface can be rendered more hydrophilic by coating with a hydrophilic polymer or by treatment with surfactants. Examples of a chemical surface treatment include, but are not limited to exposure to hexamethyldisilazane, trimethylchlorosilane, dimethyldichlorosilane, propyltrichlorosilane, tetraethoxysilane, glycidoxypropyltrimethoxy silane, 3-aminopropyltriethoxysilane, 2-(3,4-epoxy cyclohexyl)ethyltrimethoxysilane, 3-(2,3-epoxy propoxyl) propyltrimethoxysilane, polydimethylsiloxane (PDMS), γ-(3,4-epoxycyclohexyl)ethyltrimethoxysilane, poly(methyl methacrylate), a polymethacrylate co-polymer, urethane, polyurethane, fluoropolyacrylate, poly(methoxy polyethylene glycol methacrylate), poly(dimethyl acrylamide), poly[N-(2-hydroxypropyl)methacrylamide] (PHPMA), α-phosphorylcholine-o-(N,N-diethyldithiocarbamyl)undecyl oligoDMAAm-oligo-STblock co-oligomer (see Matsuda, T et al., *Biomaterials* (2003), 24, 24, 4517-4527), poly(3,4-epoxy-1-butene), 3,4-epoxy-cyclohexylmethylmethacrylate, 2,2-bis[4-(2,3-epoxy propoxy)phenyl] propane, 3,4-epoxycyclohexylmethylacrylate, (3',4-epoxycyclohexylmethyl)-3, 4-epoxycyclohexyl carboxylate, di-(3,4-epoxycyclohexylmethyl)adipate, bisphenol A (2,2-bis-(p-(2,3-epoxy propoxy) phenyl) propane) or 2,3-epoxy-1-propanol.

As mentioned above, the culture plates may have a circumferential wall. This circumferential wall, the upper face and the lower face of the culture plate may define the interior of a respective culture plate. The upper face of a culture plate is typically arranged at least essentially parallel to the lower face of the culture plate. In some embodiments the upper face of a culture plate is arranged at least essentially perpendicular to the circumferential wall of the culture plate and at least essentially perpendicular to the longitudinal axis of the housing. In some embodiments both the upper face and the lower face of a culture plate are arranged at least essentially in the plane of the inner cross section defined by the circumferential wall of the housing.

In some embodiments the upper face and/or the lower face of a culture plate is (are) arranged in an angle of inclination with regard to the circumferential wall of the culture plate. This angle may be selected in a range from 90 to 0 degrees. Typically this angle is selected in a range from 45 to about 90 degrees. It may for instance be selected in a range from about 50 to about 90 degrees, in a range from about 60 to about 90 degrees, from about 70 to about 90 degrees, from about 75 to about 90 degrees, from about 80 to about 90 degrees or from 85 to about 90 degrees. Accordingly, in some embodiments the upper face and the lower face of a culture plate are arranged offset with regard to each other.

Figure 2A:
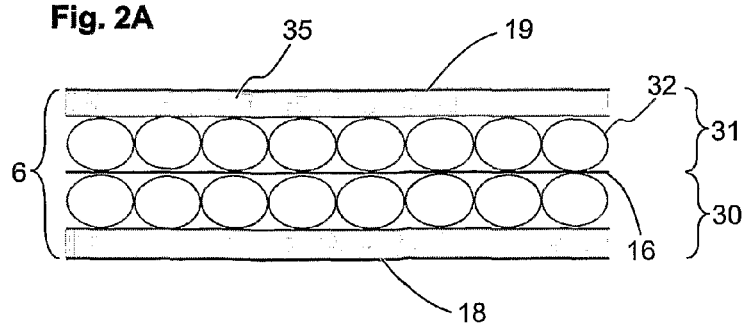
FIG. 2A depicts a cut-out of a cross section of an exemplary culture plate (6) that may be included in an apparatus of the invention. The culture plate has an upper face (19) and a lower face (18). An anchorage substrate (35) is included inside the culture plate, being deposited onto both the upper face (19) and the lower face (18). Cells (32) are arranged on the anchorage substrate (35). The culture plate (6) has a central face (16) that is sandwiched between the upper face (19) and the lower face (18). The central face (16) thus sections the interior of the culture plate into an upper (31) and a lower (30) compartment.
Figure 2B:
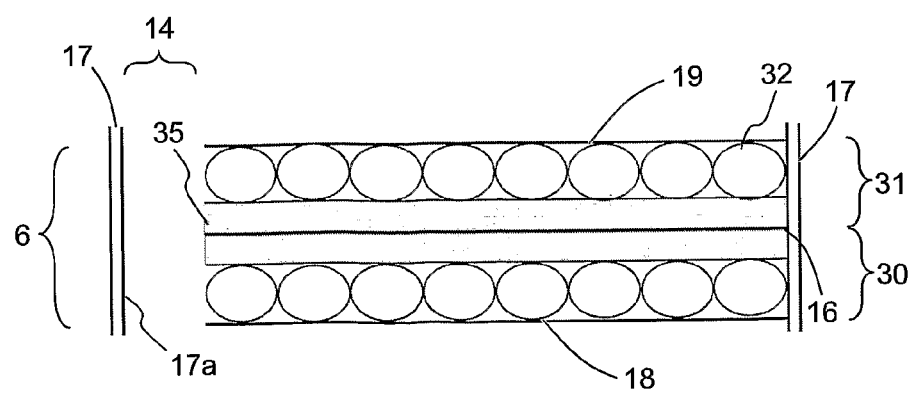
FIG. 2B depicts a schematic of a cross section of a further exemplary culture plate (6), which can be included within an apparatus of the invention. The culture plate has an upper face (19), a lower face (18), a central face (16) and a circumferential sleeve (17). The inner face (17a) of the sleeve (17), facing the central face (16), defines a circumferential wall of the culture plate (6). An anchorage substrate (35) is included inside the culture plate, being deposited onto both sides of the central face (16). Cells (32) are arranged on the anchorage substrate (35). One portion of the cells is arranged in the upper compartment (31) and one portion in the lower (30) compartment defined by the central face (16). Between the edges of the central face (16) and the inner face (17a) of the sleeve (17) there is a void interspace, in which no cells are arranged. The through hole (14) spanning the culture plate (6) is arranged at a position of the culture plate (6) where it spans this void interspace.
Figure 2C:
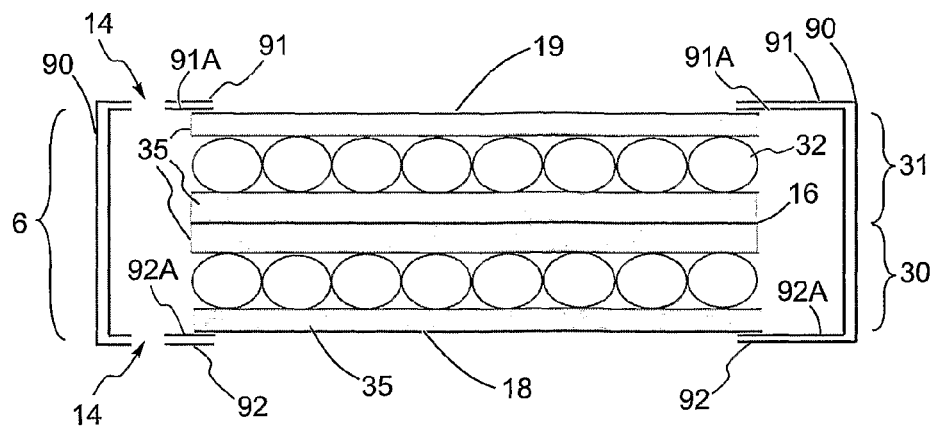
FIG. 2C depicts a schematic of a cross section of yet a further exemplary culture plate (6), which can be included within an apparatus of the invention. The culture plate has an upper face (19), a lower face (18), a central face (16) and a circumferential holder (90). The holder has an upper (91) and a lower (92) annular fringe projecting inward. Both the upper and the lower annular fringe have a lower (91A) and an upper (92A) portion, respectively, configured to contact the upper face (19) and the lower face (18), respectively. The through hole (14) spanning the culture plate (6) is arranged at a position of the culture plate (6) where it spans only the upper and lower annular fringes (91, 92) and otherwise void. An anchorage substrate (35) is included inside the culture plate, being deposited onto both sides of the central face (16) and onto both the upper face (19) and the lower face (18). Cells (32) are arranged on the anchorage substrate (35). One portion of the cells is arranged in the upper compartment (31) and one portion in the lower (30) compartment defined by the central face (16).
Figure 2D:
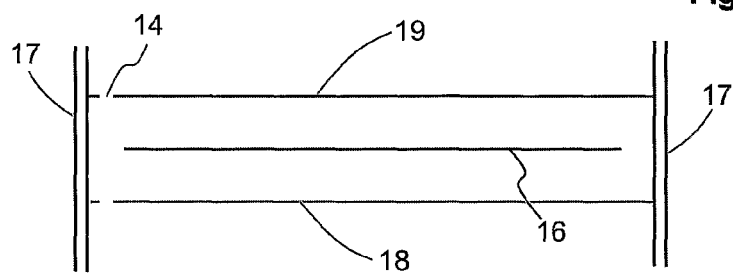
FIGS. 2D and 2E depict schematics of further possible arrangements of an upper face (19), a lower face (18), a central face (16) and a sleeve (17), with a through hole (14) arranged in the culture plate.
Figure 2E:
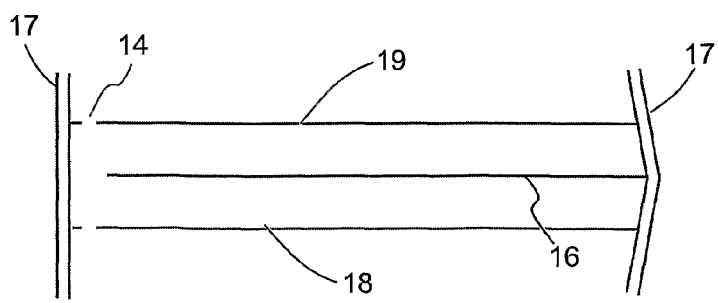
Figure 2F:
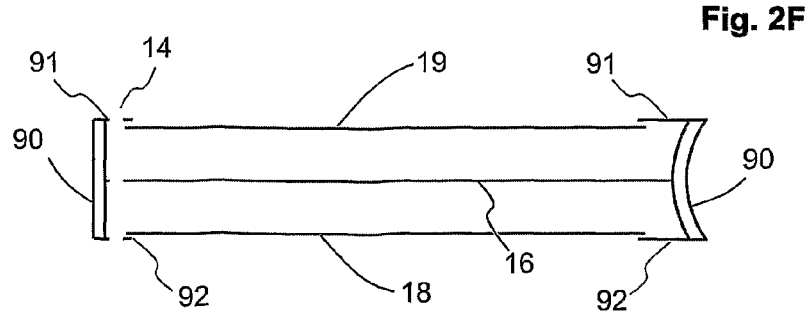
FIG. 2F depicts a schematic of a further possible arrangement of an upper face (19), a lower face (18), a central face (16) and a circumferential holder (90), with a through hole (14) arranged in the culture plate. The through hole (14) spans the upper and lower annular fringes (91, 92) of the circumferential holder (90), as well as the central face (16).
Figure 3:
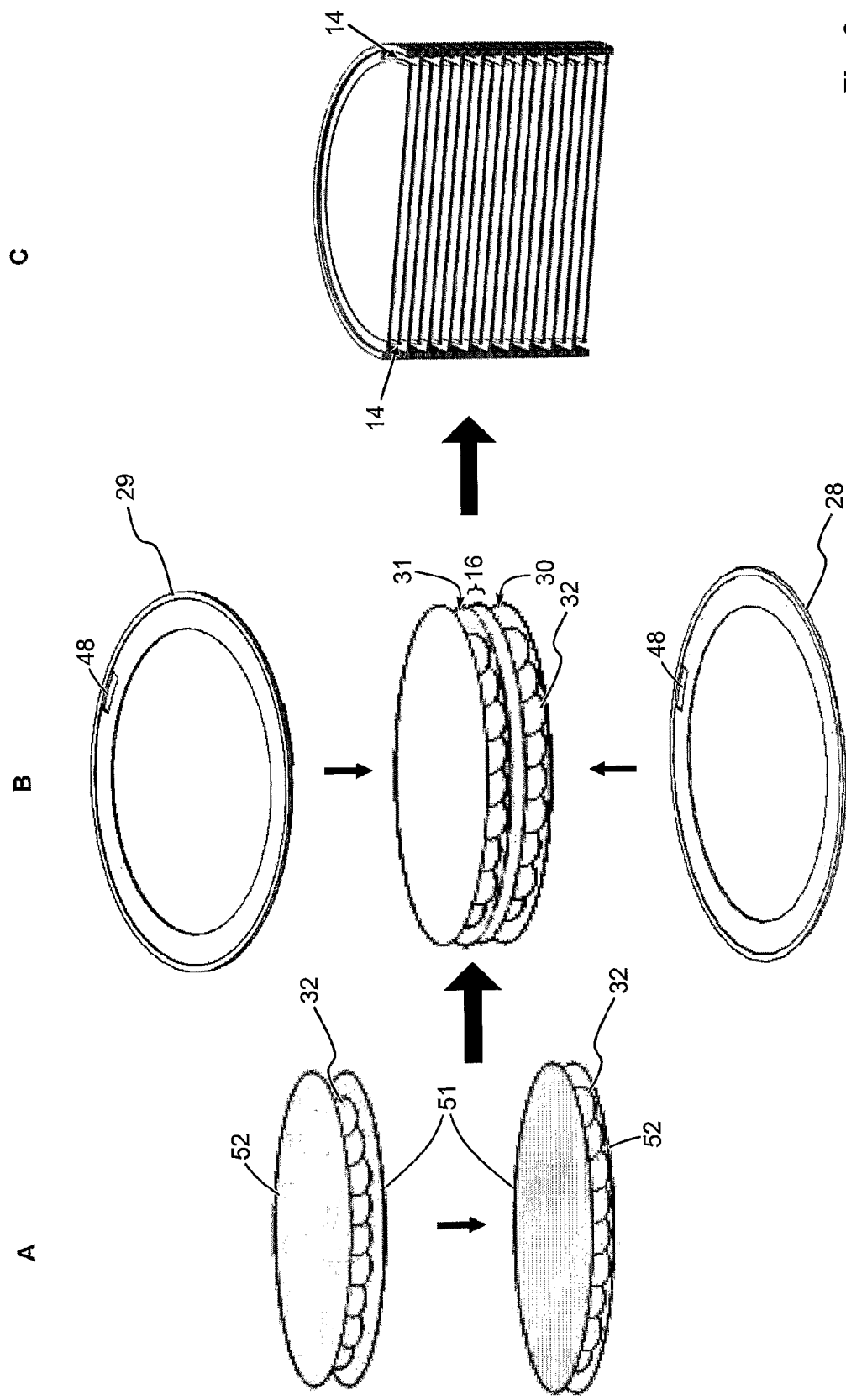
FIG. 3 depicts an example of assembling and stacking culture plates (6) in a method of the present invention. The upper and lower faces of the culture plate are formed from a porous PET membrane (52). A central face of the culture plate is formed from two non-porous PET films (51). Cells (52) are seeded on (typically anchorage substrate coated) non-porous PET films (51). Subsequently cells (52) are covered with a (typically anchorage substrate coated) porous PET membrane (52) (A). Upon assembly each cell culture plate has an upper (31) and a lower (30) compartment, each compartment corresponding to one non-porous PET film (51) covered with cells and a PET membrane (52) (B). The non-porous PET films define a central face (16) of the assembled plate. A two-part holder consisting of an upper (29) and a lower (28) portion is used to assemble the culture plates. This two-part holder is of a larger diameter than the PET films (51) and the PET membranes (52). Apertures (48) in the upper (29) and the lower (28) portion of the holder are arranged close to the circumference of the portions of the holder so as to define through-holes (14) of the plates. The plates are stacked (C) and can be placed into a correspondingly matching housing.
Figure 4A:
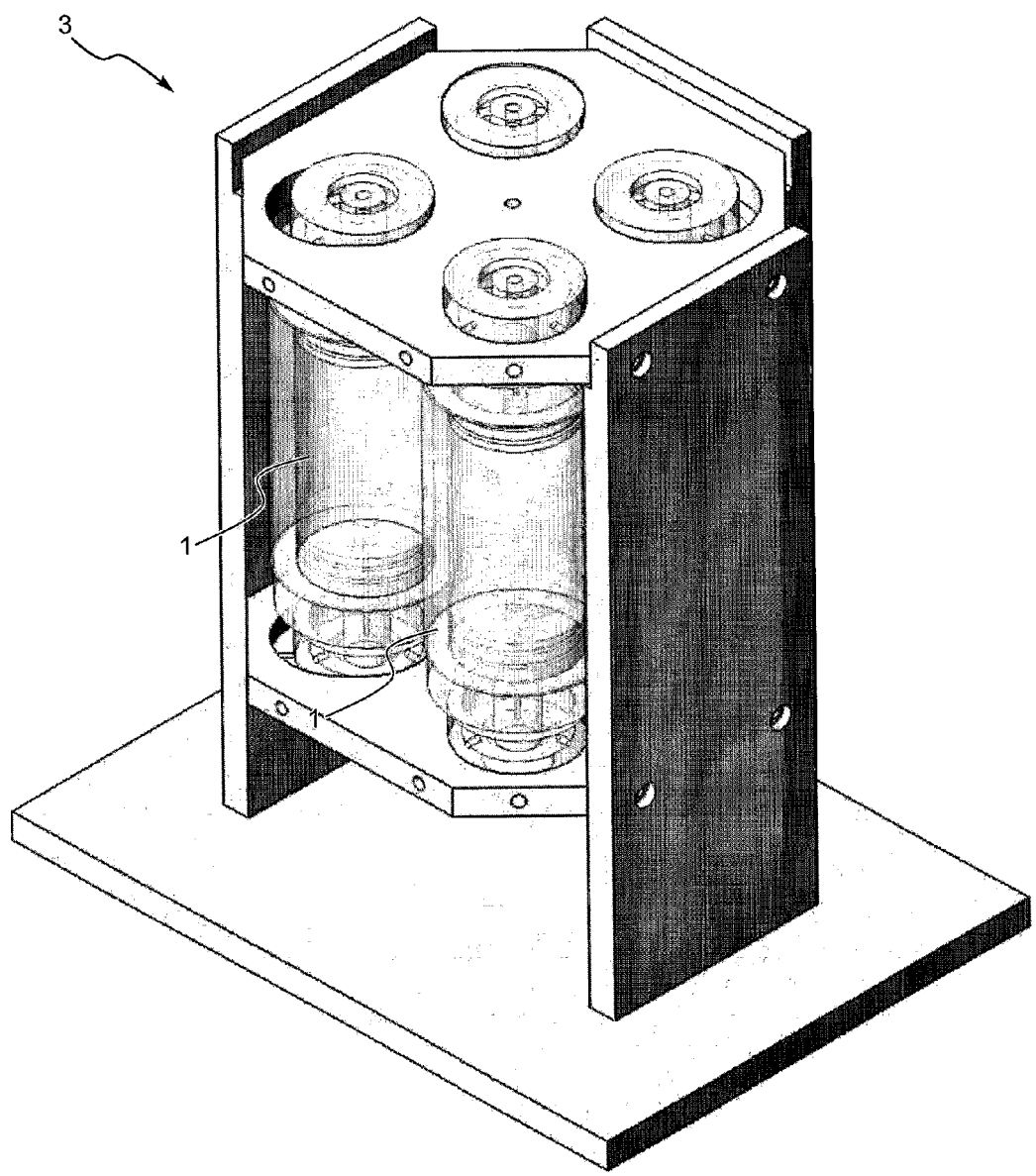
FIG. 4A shows the assembled cell culture system.
Figure 4B:
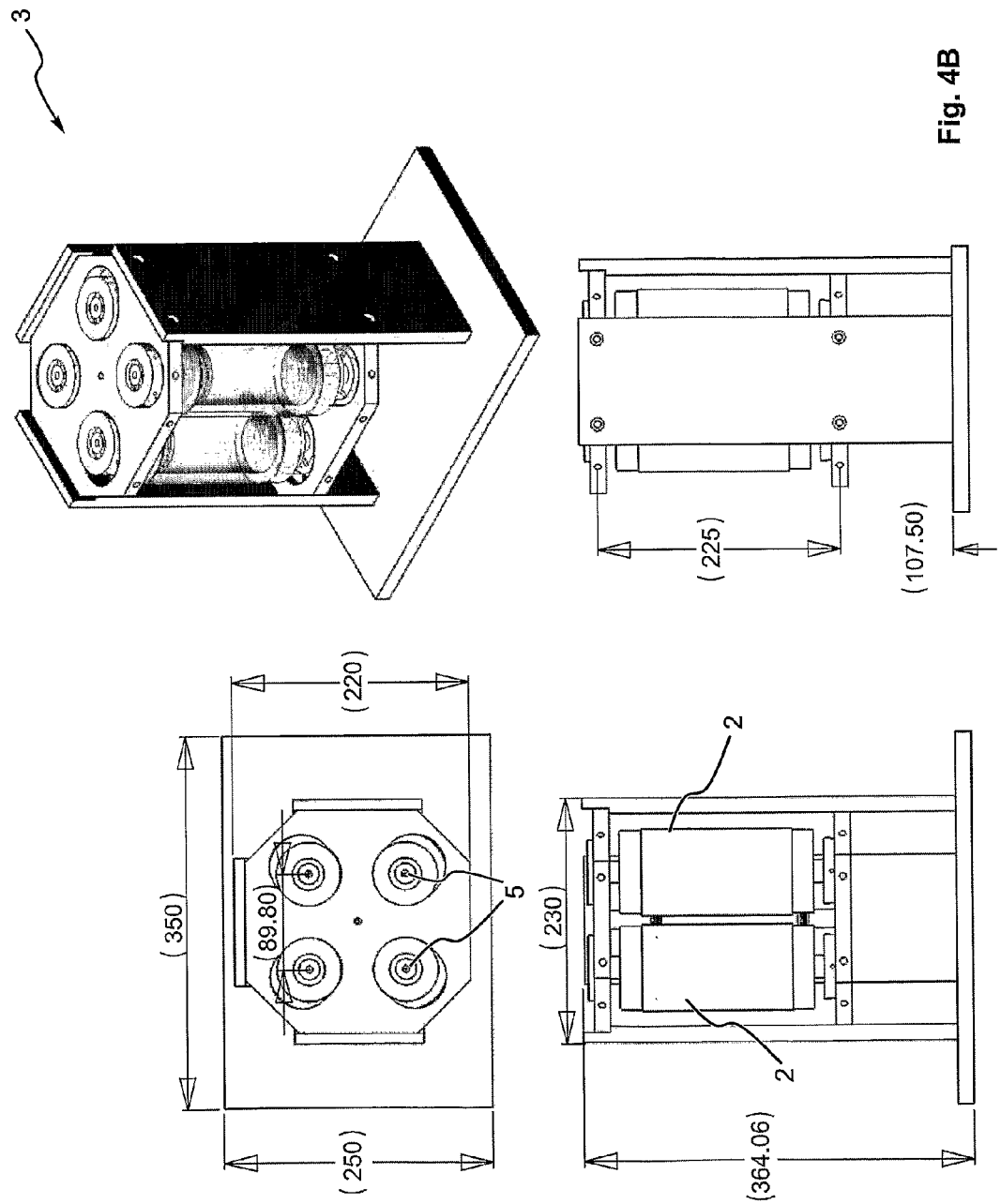
FIG. 4B depicts the dimensions of the cell culture system in top view, where the outlets (5) are visible and side view where the housings (2) are visible (lower left panel) or covered by elements of the system (lower right panel).
Figure 4C:
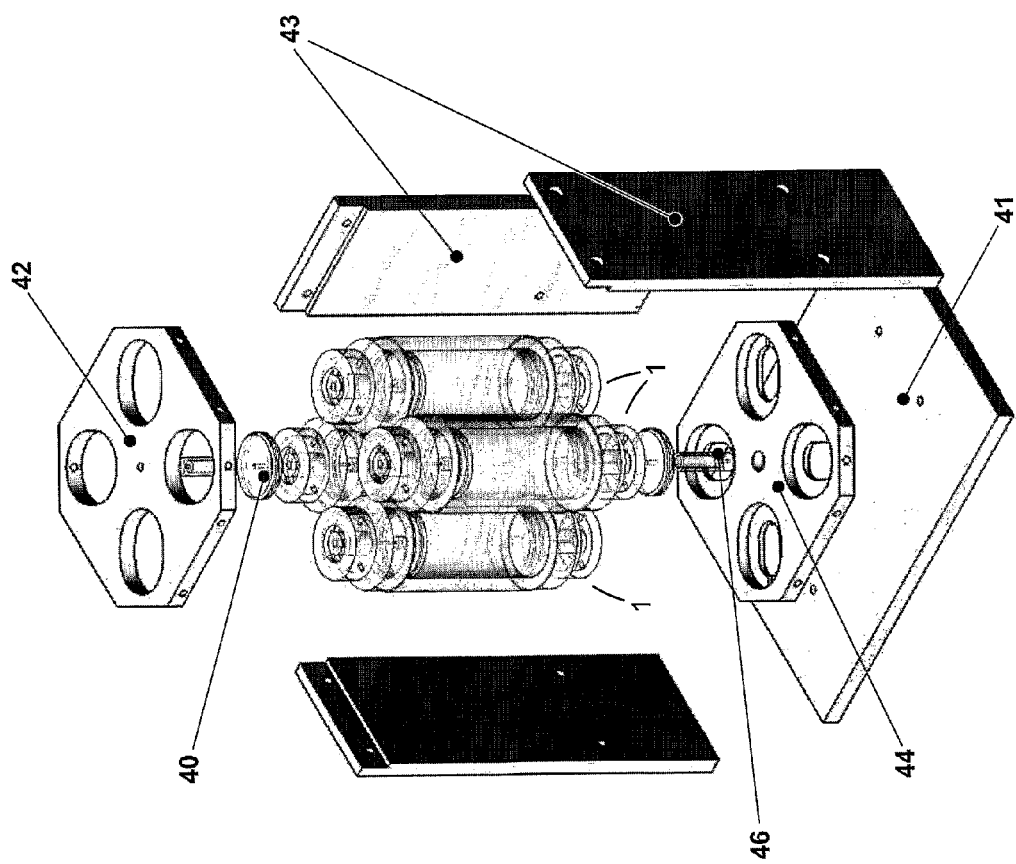
FIG. 4C shows the cell culture system in exploded view, where the apparatuses (1), side supports (43), a top support (42), a bottom support (44) and a bottom plate (41) can be seen. The system further has a motor rod (46) and a roller (40).
Figure 4D:
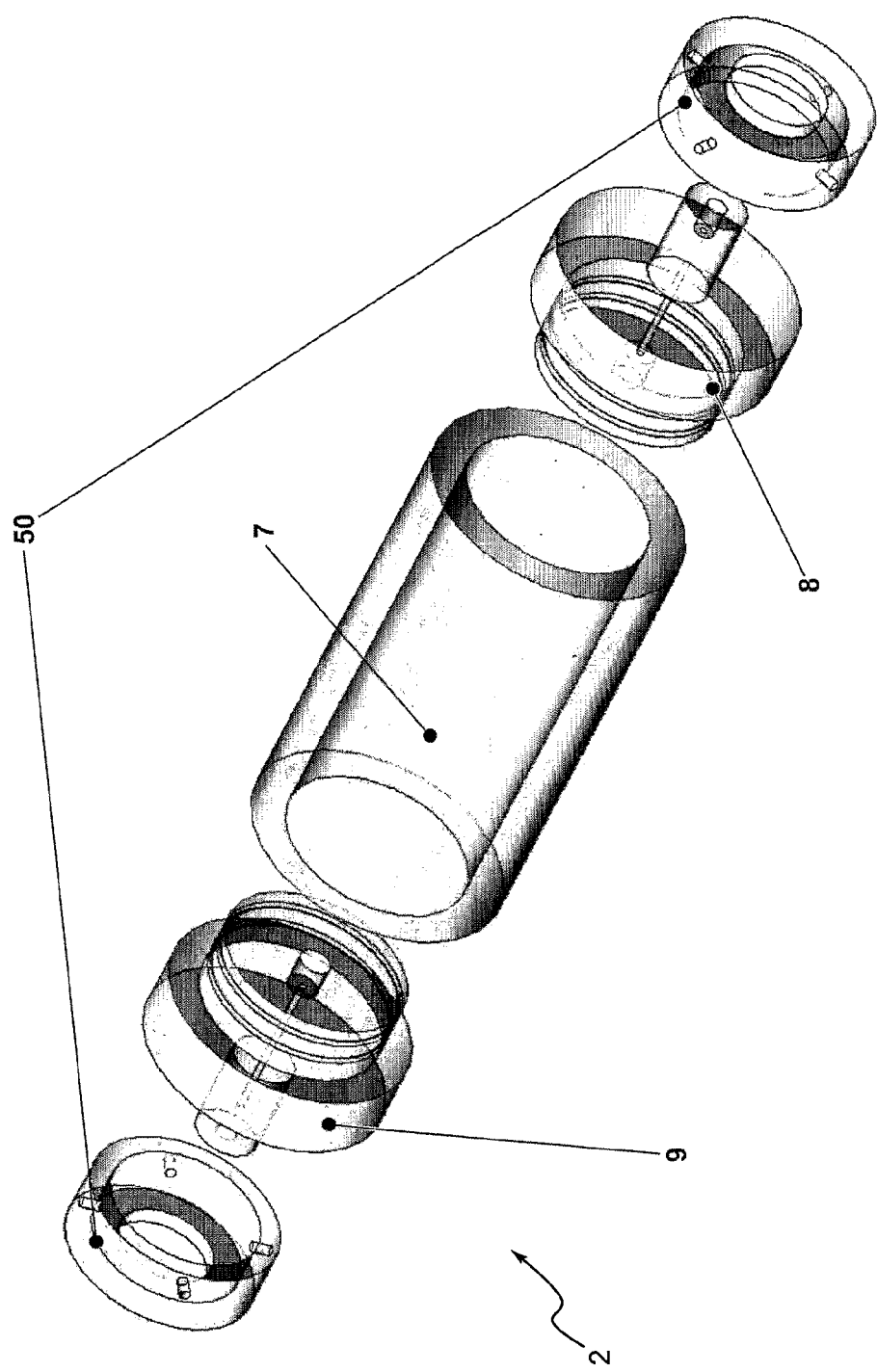
FIG. 4D depicts the housing (2) of an apparatus, which is included in the system, in exploded view. The housing includes a circumferential wall (7) in the form of a cylinder, a top wall (9) and a base (8), and bearing holders (50).
Figure 4F:
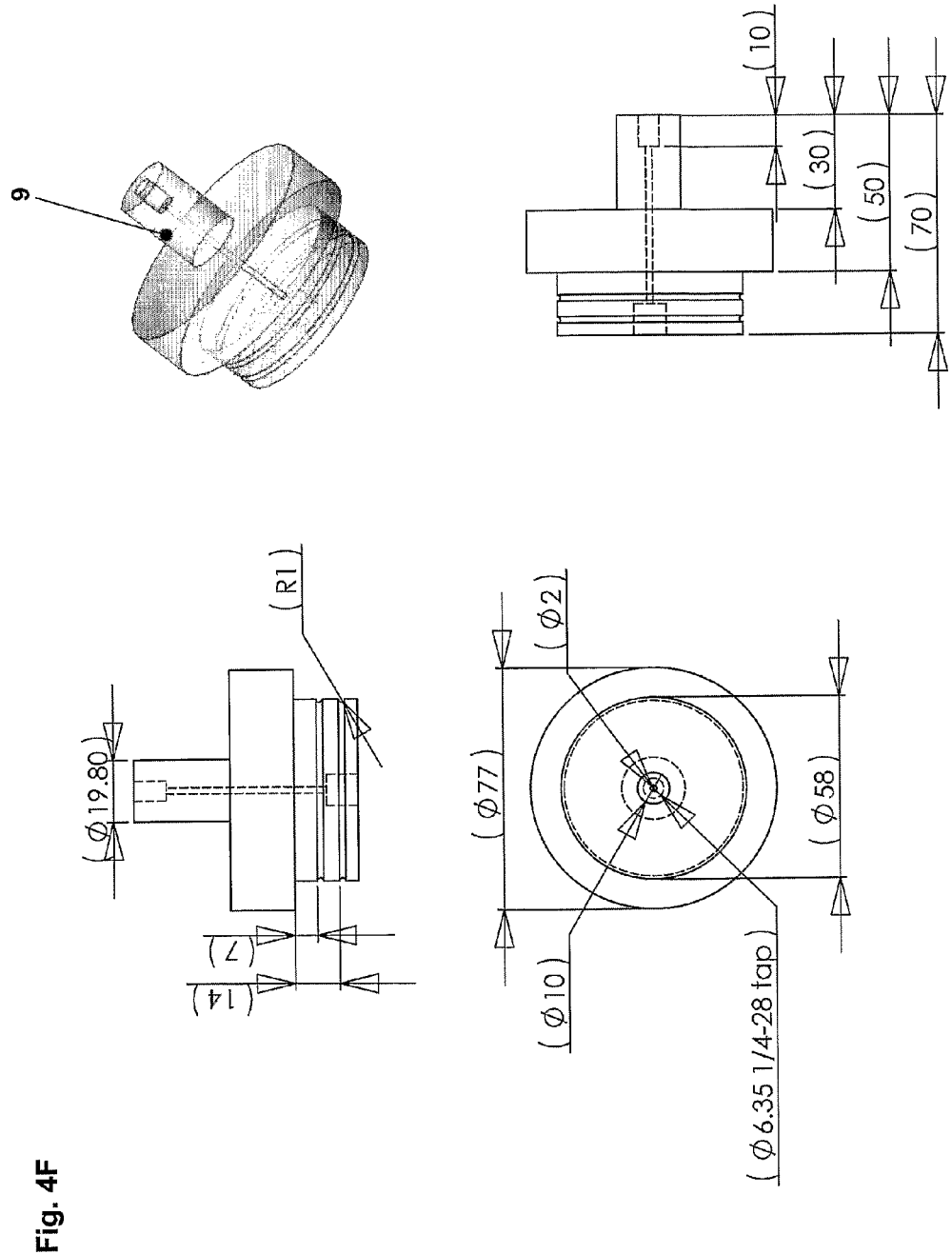
FIG. 4F shows the dimensions of a top wall (9) of an apparatus which has in the present example identical dimensions as the corresponding base (8). The top wall is depicted in top view and side view.
Figure 4I:
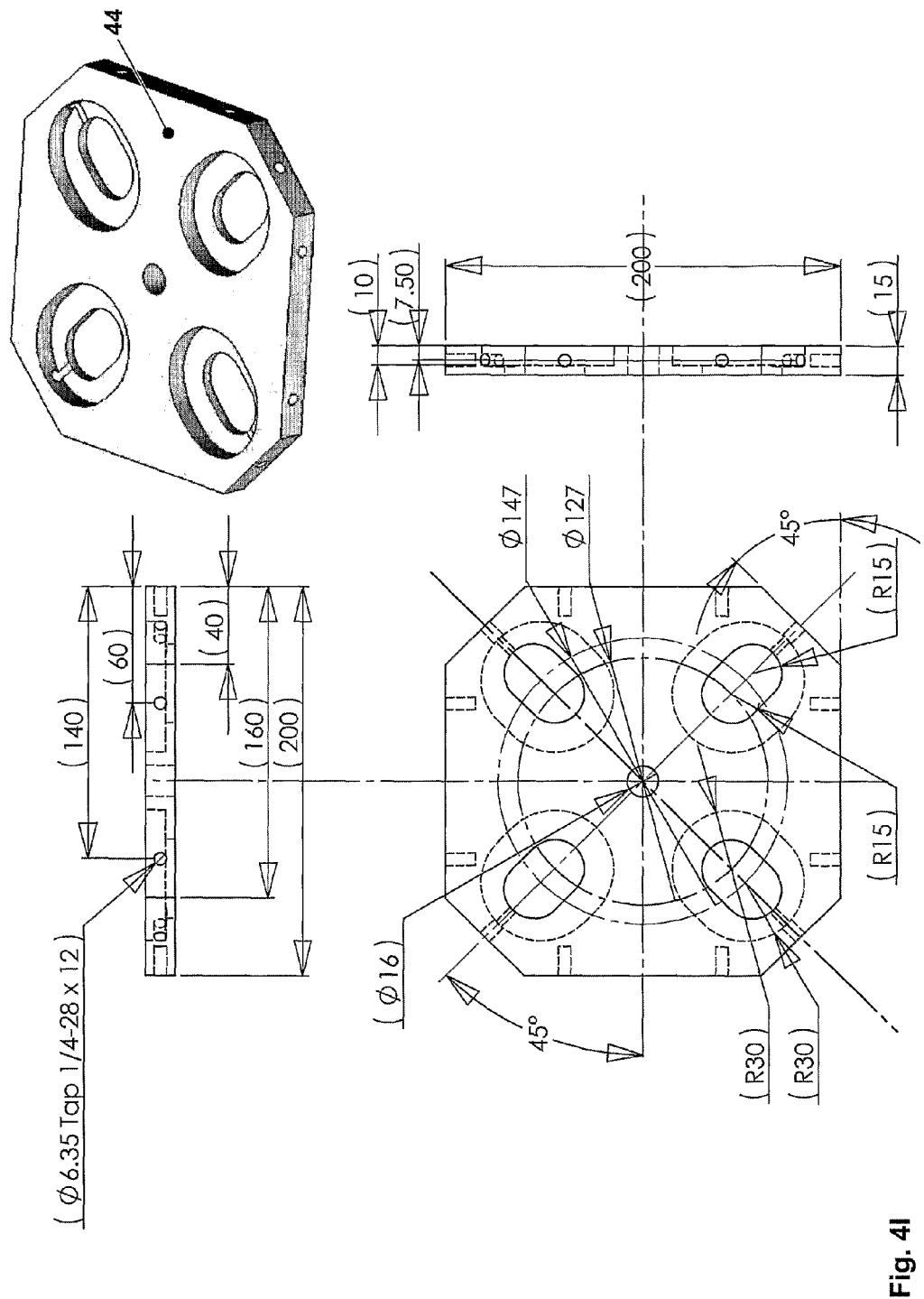
FIG. 4I shows the dimensions of a bottom support (44) of the cell culture system in top view and side view.
Figure 4K:
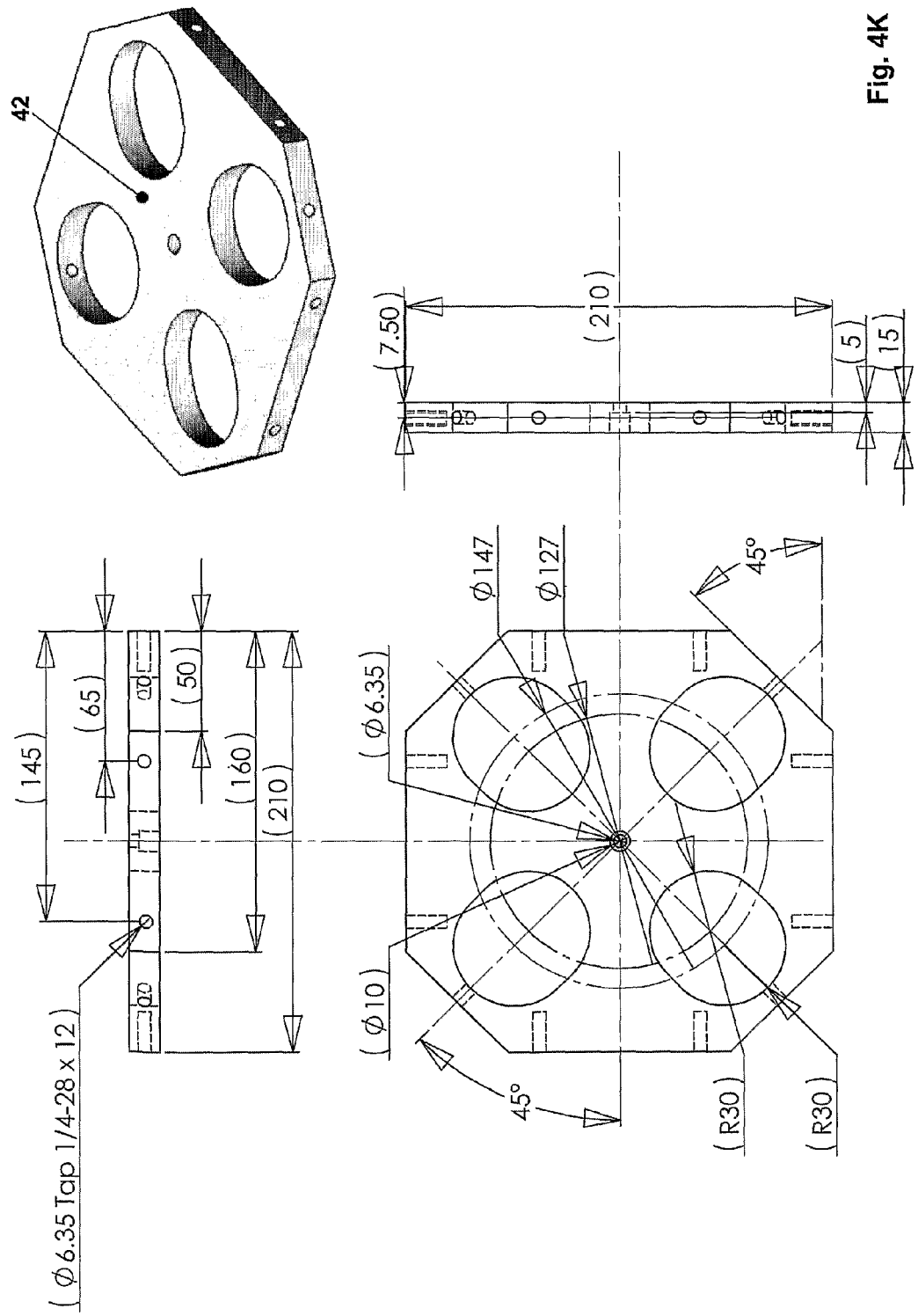
FIG. 4K shows the dimensions of a top support (42) of the cell culture system in top view and side view.
Figure 4N:
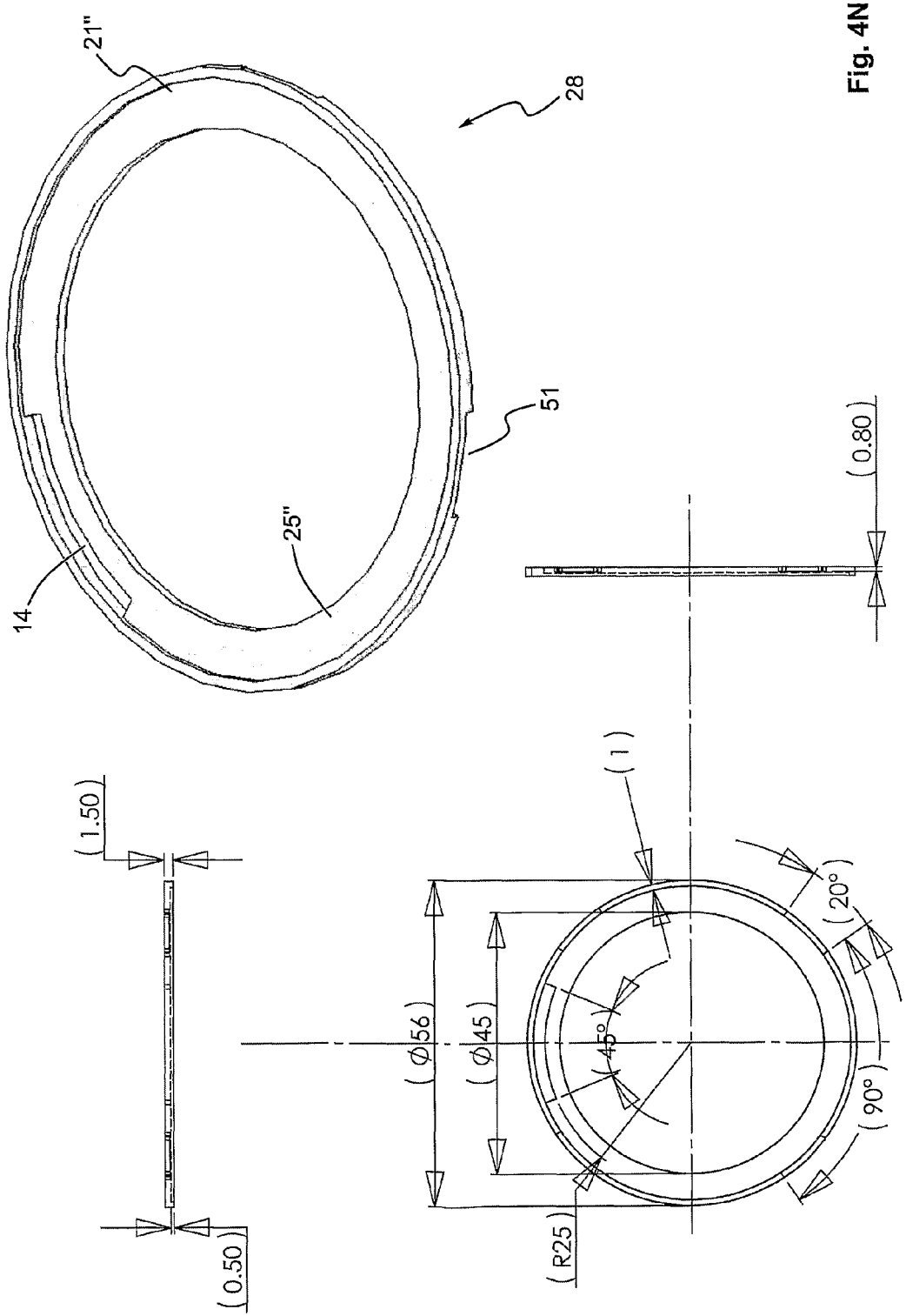
FIG. 4N shows the dimensions of the lower portion (28) of a two-part holder of an apparatus of the invention, both in top view and side view. The depicted portion has the shape of an O-ring with a lower annular stacking protrusion (21") and a lower annular fringe (25"). The depicted portion further has a recess (51) in the portion defining the sleeve of a cell culture plate, once the latter has been assembled.
Figure 4O:
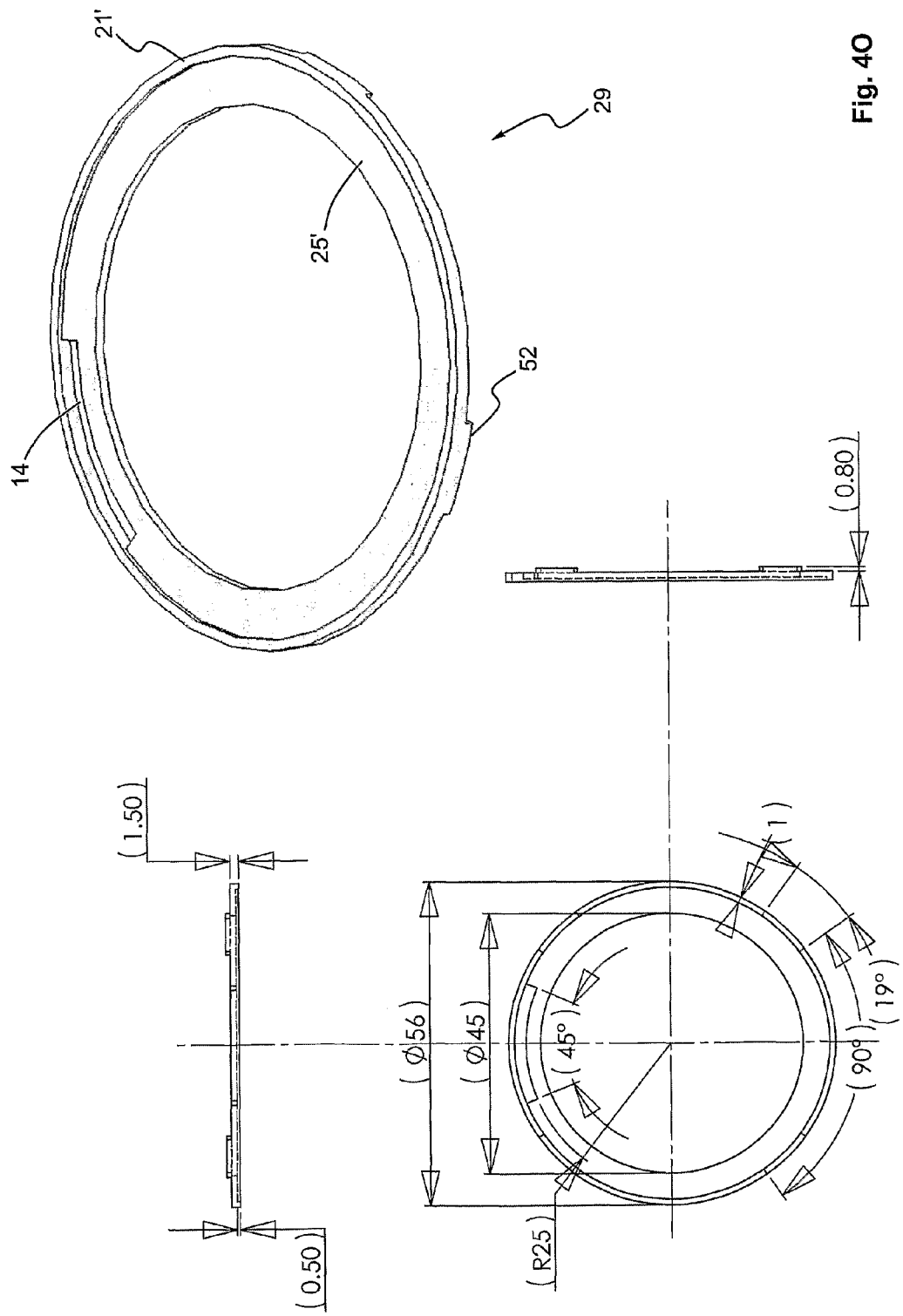
FIG. 4O shows the dimensions of the upper portion (29) of a two-part holder of an apparatus of the invention, both in top view and side view. The depicted portion has the shape of an O-ring with an upper annular stacking protrusion (21') and an upper annular fringe (25'). The depicted portion further has a ledge (52) for assembly with a lower portion of the two-part holder to secure and form a sleeve of a cell culture plate. All dimensions are in mm.

As already mentioned above, in some embodiments between the upper face and the lower face of a culture plate there is arranged a central face. This central face may be arranged at least essentially parallel to both the upper face and the lower face. The central face may accordingly be sandwiched between the upper face and the lower face of a culture plate. In some embodiments the central face is arranged in a level at least essentially perpendicular to the longitudinal axis of the housing. This central face is generally of maximally about the same dimensions, in particular the same width, in the plane defined by the (at least essentially) parallel arrangement of the culture plates in the housing. Nevertheless the central face may slightly exceed the outer dimensions of the upper and the lower face of the culture plate (cf. FIG. 2E). By "slightly" is meant in this regard that the maximal width of the central culture plate in said plane is not exceeding the maximal width of the upper and the lower plate by more than 10%, including not more than 8%, not more than 6%, not more than 5%, not more than 4%, not more than 3%, not more than 2%, not more than 1% or not more than 0.5%. In terms of absolute values by "slightly" is generally meant that the maximal width of the central face exceeds the maximal width of the upper and the lower face by no more than about 1 cm, such as about 0.5 cm, about 0.3 cm, about 0.2 cm or about 0.1 cm. In embodiments where the dimensions of the central face exceed those of the upper and the lower face, the central face determines—at least partially—the circumference and the outer dimensions of the culture plate. It is however noted that plate designs with such a prominent central face require particular attention with regard to the stability as well as with regard to the fitting into the housing of the apparatus. It may in such embodiments be advisable to equip the housing of the apparatus with circumferential indentations that are capable of securing the culture plates by accommodating the respective jut or protrusion defined by the large central face.

In some embodiments the central face is accordingly of smaller dimensions in the plane defined by the parallel arrangement of the culture plates than the upper and the lower plates. The circumference of the central face may in such embodiments be arranged in any desired orientation. Where the upper and the lower face are for instance of square profile, the central face may be of smaller square profile with the respective angles of its profile offset with regard to the angles of the profile of the upper and the lower face. In this example the central face may also be of any other profile such as triangular or ovoid as long as its maximal width allows it to be arranged within the profile of the upper and the lower face. If an arrangement of the profile of the central face causes any portion of the central face to exceed the profile of the upper and the lower face, this embodiment falls under the slightly exceeding outer dimensions defined above. As will be apparent from the above the profile of the central face may be selected in such a way that the central face does not entirely span the circumference of the culture plate. Thus in some embodiments there are positions on a face of a culture plate below which a central face is arranged while below other positions on the same face of the same culture plate no central face is arranged. The latter positions correspond to positions up to which the central face does not span the culture plate in the plane of the respective face.

The central face may be rigid or flexible. In some embodiments the central face is of the same rigidity as the upper face and the lower face. In some embodiments the central face is of lower rigidity as the upper face and the lower face. In some embodiments the central face is of higher rigidity as the upper face and the lower face. Such a central face may thus separate the culture plate, including each culture plate, into a lower compartment and an upper compartment. Typically the lower and the upper compartment are in fluid communication with each other, for instance via an aperture in the central face. In some embodiments the central face includes, e.g. is made up of, two layers arranged in parallel. These two layers of the central are in some embodiments flexible layers that include a polymer.

As mentioned above, in some embodiments a respective circumferential wall of a culture plate is included in a sleeve thereof, the sleeve thus defining the circumference of the culture plate. Each culture plate may be mounted and sealed to the circumferential wall of the housing of the apparatus by means of such a sleeve of the culture plate. Such a sleeve may be provided by a circumferential holder as explained below. A respective sleeve may further define an annular stacking protrusion. The annular stacking protrusion may project from the upper face of the culture plate, from the lower face of the culture plate or from both faces. This annular stacking protrusion generally has the same profile as the circumference of a corresponding culture plate and thus also a profile matching the circumferential wall of the housing. The annular stacking protrusion may for instance have the shape of a circular or ovoid collar, the profile of an egg, letters V or U, the profile of a triangle, the profile of a rectangle, of a square, or of any polyhedron. This annular stacking protrusion may project parallel to the longitudinal axis of the housing. Accordingly, the annular stacking protrusion generally projects along the direction of the circumference of the plate defined be the sleeve. In some embodiments the annular stacking protrusion is projecting perpendicular to the plane defined by the culture plate. In some embodiments the annular stacking protrusion is projecting perpendicular to the face of the culture plate from which it is projecting. Where the annular stacking protrusion projects from the upper face of the culture plate it may thus for instance be projecting perpendicular to the upper face of the culture plate. In some embodiments a sleeve has an upper annular stacking protrusion and a lower annular stacking protrusion, i.e. an annular stacking protrusion projects from both the upper face of the culture plate and from the lower face of the culture plate. In some embodiments both the upper annular stacking protrusion and the lower annular stacking protrusion project in a direction perpendicular to both faces of the culture plate.

Annular stacking protrusions of culture plates may be used as a spacer in the stacking of culture plates in the housing of the apparatus of the invention. In some embodiments a culture plate of the plurality of culture plates is accordingly mounted to an adjacent culture plate via its annular stacking protrusion. Where the culture plates have annular stacking protrusions projecting from both the upper face and the lower face of the culture plate, two adjacent culture plates are coupled via contact of their stacking protrusion. In some embodiments the stacking protrusions of adjacent culture plates are fitted to define a circumferential wall of the space between two adjacent culture plates. In some embodiments the annular stacking protrusions of the plurality of culture plates are of at least substantially uniform height in the direction of the longitudinal axis of the housing. As explained above, in some embodiments this direction is the direction perpendicular to the culture plates. Thereby the annular stacking protrusions define, in such embodiments, an at least essentially unitary distance between opposing faces of adjacent culture plates.

In some embodiments where a sleeve is arranged at the circumference of a culture plate the sleeve may be included in a circumferential holder, providing a circumferential wall of the culture plate. The sleeve may define the circumferential wall of the culture plate and further be a portion of the circumferential holder. A respective holder may have an upper and/or a lower fringe. The fringe may be arranged in abutment to the upper face of the culture plate. In such an embodiment the fringe may be termed an upper fringe. Typically the upper fringe is arranged in a position above the upper face of the culture plate. Further the upper fringe projects in the plane of the width of the respective upper face of the culture plate. It projects toward the longitudinal axis of the housing of the apparatus, i.e. in the direction, for instance radially, of the center of the upper face of the culture plate. Further, the upper annular fringe may include a contacting portion. This contacting portion is configured to contact the upper face of the culture plate. The contacting portion may for instance be a surface facing the upper face of the culture plate. It may be of corresponding surface characteristics, i.e. selected to match those of the upper face of the culture plate. The contacting portion may further be of a width that is selected to provide a space for contacting, possibly also for securing, the upper face of the culture plate. In some embodiments the fringe may be arranged in abutment to the lower face of the culture plate. In such an embodiment the fringe may be termed a lower fringe. Typically the lower fringe is arranged in a position below the lower face of the culture plate. The above definitions regarding the relation of upper fringe and upper face of the culture plate apply mutatis mutandis to the lower fringe of the circumferential holder.

In some embodiments such a holder has an upper and a lower fringe. The upper and the lower fringe may be projecting at least essentially perpendicular to the circumferential wall of the holder. The upper and the lower fringe of the circumferential holder may be designed to removably hold the upper face and the lower face of a culture chamber, respectively, in position. In some embodiments the circumferential holder is a two-part holder. The two-part holder may be separably consisting of an upper and a lower portion. The upper portion may include an upper fringe and the lower part may include a lower fringe, each fringe defining a corresponding annular stacking protrusion. In addition to a corresponding fringe the circumferential holder may include an annular stacking protrusion of a culture plate as defined above.

In some embodiments a holder further has an annular fringe projecting inward from the circumferential wall of the holder. The fringe may project in a direction at least essentially parallel to the plane defined by the parallel arrangement of culture plates in the housing. The annular fringe is arranged at the upper face or the lower face of the culture plate. It is arranged above the upper plate or below the lower plate. Accordingly the annular fringe is orientated towards the space between two adjacent culture plates. In other words, seen from the interior of the culture plate the annular fringe is arranged beyond the upper and the lower face of the culture plate, respectively, i.e. on the other side. In some embodiments a holder has an upper annular fringe and a lower annular fringe. Both the upper and the lower annular fringe are orientated toward the space between two adjacent culture plates. In one embodiment each culture plate of an apparatus of the invention has a holder with an upper annular fringe and a lower annular fringe. A respective upper annular fringe may contact the upper face and a lower annular fringe may contact the lower face. Hence, in such embodiments the holder is capable of supporting the respective upper and lower face and holds the upper and the lower face in position.

In some embodiments the maximal width of a culture plate is defined by the holder. In some embodiments the profile of the culture plate in the plane defined by the parallel arrangement of the culture plates is defined by the holder. In such embodiments the upper face and/or the lower face may be of smaller profile in the plane defined by the parallel arrangement of the culture plates than the circumference of the culture plate. In such embodiments the upper and/or the lower face do(es) not entirely span the culture plate between the outer ends thereof that define the circumference. In such embodiments there thus remains a distance between the circumference of a face of the culture plate and the circumference thereof. This distance is covered by the annular fringe of the holder.

As an illustrative example, the culture plate may be a flat plate of circular profile. A plain upper face and a plain lower face may be arranged in parallel, both having the same radius. Both the upper face and the lower face may have a radius that is smaller than the radius of the holder. In such an embodiment the upper and the lower face may both have a radius of 3.5 cm (i.e. a diameter of 7 cm). The holder may be of circular profile in the plane defined by the parallel arrangement of the culture plates and have an inner radius of 4 cm (i.e. a diameter of 8 cm). The holder may further have an upper and a lower annular fringe projecting inward in a plane parallel to the upper and the lower face. Both the upper and the lower annular fringe may project inward over a distance of 0.7 cm. In such embodiments the upper and the lower face can safely be arranged in the holder albeit not spanning the entire diameter. Further matter in the interior of the culture plate such as cells and/or an anchorage substrate may provide further support for the upper and lower faces from inside the culture plate, thereby further securing the position of the upper and lower faces.

Accordingly, in some embodiments the sleeve may be, or be included in, a two-part holder. Such a two-part holder may separably consist of an upper and a lower portion. In some embodiments a respective two-part holder has both an upper annular stacking protrusion and a lower annular stacking protrusion as defined above. The upper portion of the two-part holder may include the upper annular stacking protrusion, and the lower part of the two-part holder may include the lower annular stacking protrusion.

Each culture plate of the plurality of plates has a through hole. As a result the inlet and the outlet of the housing are in fluid communication. The through hole spans each culture plate. Accordingly the upper face and the lower face of each culture plate have an opening, thereby providing fluid communication of the interior of each culture plate with the inlet and the outlet of the housing. The openings in the upper and in the lower face, defined by a through hole, are thus arranged in at least essentially identical orientation with respect to the longitudinal axis of the housing. Generally, the openings in the upper face and the lower face are arranged at at least substantially about the same position with regard to the distance to the longitudinal axis of the housing and within the plane of the respective culture plate. In this regard the plane of a culture plate with parallel upper and lower faces is a plane parallel to the plane of each respective face. The plane of a culture plate with upper and lower faces that are inclined to each other is defined by a plane that would correspond to a mean plane that has equal distances to both the upper and the lower face of a culture pate.

The through hole of each culture plate is furthermore positioned at an outer end of the culture plate, i.e. at an outer end with regard to the longitudinal axis defined by the circumferential wall of the housing. The through hole is positioned next to the circumference of the plate, e.g. contiguous to a circumferential wall of the culture plate, if present, and thus also proximate the circumferential wall of the housing. As explained above, in some embodiments a culture plate has a sleeve that provides a circumferential wall of the culture plate. Accordingly, in such embodiments the through hole may be positioned proximate the sleeve. In some embodiments the through hole of each culture plate is positioned at an outer end of the culture plate, proximate the sleeve thereof. In some embodiments the through hole is positioned at a distance of less than a quarter, of less than about a fifth, about a sixth or about a seventh part, such as less than about 12%, less than about 10%, or less than about 5%, of the maximal width of the culture plate away from its circumference, in a radial direction. In embodiments where the culture plates are of circular profile, embodiments the through hole is positioned at a distance of less than about half, less than about a third, about a quarter, about a fifth, about a sixth part, such as less than about 12%, less than about 10%, about 7.5%, or less than about 5%, of the radius of the culture plate away from its circumference, in a radial direction. The distance may in such embodiments of a culture plate of circular profile also be taken as more than about half, more than about two thirds, more than about three-fourths, such as more than about 80%, more than about 85%, more than about 90% or more than about 95% apart from the longitudinal axis defined by the circumferential wall of the housing.

In some embodiments a central face is sandwiched between the upper face and the lower face of the culture plate. The through hole of the culture plate may accordingly also span across such a central face longitudinally. This is generally the case in embodiments where the central plate spans the entire culture plate within the circumference thereof. In such embodiments the central face thus has an opening arranged in at least essentially identical orientation with respect to the longitudinal axis of the housing as the upper face and the lower face. The above said regarding the arrangements of the upper face and the lower face therefore likewise applies to a central face, if present. In some embodiments the central face is of smaller profile in the plane defined by the parallel arrangement of the culture plates than the upper and the lower face. In such embodiments the central face does not entirely span the culture plate between the outer ends thereof that define the circumference. In such embodiments the through hole may span across the central face longitudinally. This is the case if the through hole is arranged in a position in the plane of the culture plate where the central face is still present.

As an illustrative example, the culture plate may be a flat plate of circular profile. A plain upper face and a plain lower face may be arranged in parallel, both having the same radius. The upper the lower face may further be positioned level with each other in that centers of both faces define an axis that is about perpendicular to each of the faces. In other words, the circumferences of both faces define a common circumference of the culture plate that is perpendicular to each of the upper and lower face. The culture plate may also include a plane central face, arranged in parallel to the upper face and the lower face. The central face may have a radius that is smaller than the radius of the upper face and the lower face (cf. FIG. 2B). In such an embodiment the upper and the lower face may both have a radius of 4 cm (i.e. a diameter of 8 cm). The central face may have a radius of 3.5 cm (i.e. a diameter of 7 cm). In such embodiments the central face may be centrically arranged, i.e. its center may be arranged in the position that is defined by the center of both the upper face and the lower face. There thus remains a void around the central face, between the circumference of the central face and the circumference of the culture plate. If the through hole spanning the culture plate is arranged at the edge of the culture plate, i.e. at the circumference of both the upper and the lower face of the plate and the through hole is of a width of less than about 0.5 cm in the plane of the two faces, it does not span the central face. If the through hole is however arranged radially at a distance of e.g. 3.5 cm or less from the center of the culture plate (i.e. 0.5 cm or more from its circumference) it spans the central face. Likewise, if the central face is arranged offset with regard to the upper and the lower face of a culture plate, rather than centrically arranged, the thorough hole may span the central face. If for example the central face in the above example with a radius of 3.5 cm is arranged to adjoin the circumference of the culture plate with a radius of 4 cm on one side, there is a void between circumference and central face of 1 cm on the opposite side. If the through hole is positioned to span this void, it does not span the central face.

As explained above, in some embodiments one or more culture plates, including all culture plates, have a holder with a circumferential wall, an upper and a lower annular fringe. The maximal width of a culture plate may be defined by the holder. In some embodiments the upper face and/or the lower face may be of smaller profile in the plane defined by the parallel arrangement of the culture plates than the circumference of the culture plate. In some embodiments a culture plate with a respective holder includes a central face. Each of the upper, the lower and the central face may be of smaller profile in the plane defined by the parallel arrangement of the culture plates than the profile of the holder in this plane. In such embodiments none of the three faces does entirely span the culture plate between the outer ends thereof that define the circumference. In such embodiments the through hole may span across any, including all of the upper, lower and central face longitudinally. This is the case if the through hole is arranged in a position in the plane of the culture plate where the respective face is still present.

In some embodiments the through hole is arranged in the upper and lower annular fringes of the holder of a culture plate. In some of these embodiments the through hole is arranged at a position up to which only one or two of the upper, lower and central face are spanning. In one embodiment the through hole is arranged at a position where between all three faces and the circumference of the culture plate there is a void. In such embodiments the through hole spans the entire culture plate without spanning any of the upper, lower and central face.

Following the illustrative example above, the culture plate may be a flat plate of circular profile. A plain upper face, a plain lower face and a plain central face may be arranged in parallel, all three of them having the same radius. All three faces may further be positioned level with each other in that centers of all three faces define an axis that is about perpendicular to each of the faces. The culture plate may also include a circumferential holder that has a circumferential wall, an upper and a lower annular fringe, arranged in parallel to the upper face and the lower face. The upper, lower and central faces may have a radius that is smaller than the radius defined by the inner face of the circumferential wall of the holder. The upper and the lower annular fringes of the holder may project inward over a distance of 0.7 cm. In such an embodiment the radius defined by the inner face of the circumferential wall of the holder may be 4 cm (i.e. a diameter of 8 cm). The upper, lower and central faces may have a radius of 3.5 cm (i.e. a diameter of 7 cm). In such embodiments the upper, lower and central faces may be centrically arranged, i.e. their centers may be arranged in the position that is defined by the center of the inner cross-section of the circumferential holder in the same plane. There thus remains a void around all three faces, between the circumference of the faces and the inner circumference of holder. If the through hole spanning the culture plate is arranged at the edge of the culture plate, i.e. in the upper lower annular fringes and the through hole is of a width of less than about 0.5 cm in the plane of the faces of the plate, the through hole not span any of the three faces—albeit spanning the entire culture plate. The above said with regard to the orientation of a smaller central face in relation to larger upper and lower faces applies mutatis mutadis.

The through holes of adjacent culture plates are positioned distally in the plane defined by the at least essentially parallel arrangement of the culture plates. As explained above, this plane corresponds in some embodiments to the plane defined by the inner cross section of the circumferential wall of the housing.

In some embodiments a first culture plate and an adjacent second culture plate of the plurality of culture plates are arranged in the housing in at least essentially opposite orientations of their through holes with respect to the longitudinal axis of the housing. The through holes of adjacent culture plates are thus in some embodiments positioned at at least essentially opposite ends with respect to the longitudinal axis of the housing. Accordingly, where a first culture plate and an adjacent second culture plate are arranged with the upper face of a first culture plate being in abutment to the lower face of a second culture plate, the through hole included in the upper face of a first culture plate is in some embodiments positioned in at least essentially opposite orientation to the through hole included in the lower face of the second culture plate with respect to the longitudinal axis of the housing.

In some embodiments the through hole(s) of one or more culture plates, including of each culture plate, is arranged at the edge of both the upper and the lower face thereof. In these embodiments the through hole may be laterally defined by the circumferential wall of the housing of the apparatus. Where the respective culture plate has a circumferential wall, in these embodiments the through hole may be laterally defined by the circumferential wall of the culture plate. In embodiments where a culture plate has a sleeve that provides a circumferential wall of the culture plate, the through hole may be laterally defined by the sleeve of the culture plate Such an arrangement of through holes of adjacent culture plates achieves a serial flow of a medium through the spaces between adjacent culture plates. A medium in the form of a fluid enters the culture chamber that is defined by the inner faces of the circumferential wall of the housing, of the base and of the top wall thereof (supra) via the inlet in the base wall. It flows to a first through hole in a culture plate, passes the through hole, flows through the space between the opposing faces of two adjacent culture plates and flows further through another through hole. In use for culturing anchorage-dependent cells (adherent cells) each culture plate includes a plurality of adherent cells. These cells may advantageously be arranged about the face of a culture plate, in particular within the culture plate, contiguous to a face thereof, for example immediately below the upper face of a culture plate. In order to maintain these cells it is vital to provide a continuous flow of nutrients and oxygen around the cells without exposing the cells to an overly high shear stress. The arrangement of through holes distally in the plane defined by the at least essentially parallel arrangement of the culture plates forces fluid to perform this task by forcing it to flow parallel to the opposing faces of two adjacent culture plates. Furthermore with an optimized shape and arrangement of the through hole arranged in a culture plate (e.g. close to the edge, lengthy) it is possible to aim for a flow velocity that is at least substantially uniform along the face of a culture chamber. Using the architecture of the apparatus of the invention it is possible to achieve, at least along a large portion of the face of a culture plate (cf. FIG. 7) flow conditions that resemble the laminar flow obtainable in a single-chamber bioreactor for drug testing (cf. e.g. Xia, L, et al., *Biomaterials* (2009) 30, 5927-5936).

As explained above, in one embodiment the through holes are provided by a holder with an upper and a lower annular fringe, while the dimensions of the upper, the lower and a central face of a culture plate provide a void between the circumferential wall of the plate and the respective plate. This void is spanned by the through hole. In such an embodiment the upper and he lower face may be defined by a porous semi-rigid layer that permits nutrients and gases dissolved in the medium, such as oxygen, to pass. The central face may in such an embodiment be defined by one or two layers of a rigid or semi-rigid matter that does, at least essentially, not permit nutrients and gases dissolved in the medium to pass. A medium in the form of a fluid passing the through hole of such a culture plate enters the same via the hole on the lower annular fringe. It then flows past a porous semi-rigid layer, then past a layer or a double layer of a rigid or semi-rigid matter, thereafter past a further porous semi-rigid layer and finally exit the plate via a hole in the upper annular fringe.

The through holes of the culture plates may be of any profile in the plane of the culture plate. In typical embodiments the profile of a though hole is of elongated shape in the plane of the culture plate. In some embodiments the through hole of a culture plate is a slit. In some embodiments the through holes of the culture plates in the apparatus are all at least essentially of the same dimensions and the same any profile in the plane of the culture plate. Thus in some embodiments the though hole of each culture plate is a slit.

The through holes of the culture plates are selected to be of dimensions that allow an at least essentially uniform flow distribution of a fluid flowing along the upper and lower faces of the plate. In this regard it is advantageous to select a though hole to be of elongated shape in the plane of the culture plate, lengthwise arranged at least essentially parallel to the circumference of the culture plate. The though hole may for instance define a longitudinal axis in the plane of the culture plate, as is for example the case with a straight slit. This longitudinal axis may be arranged perpendicular to a radial direction of the culture plate. In embodiments where the faces of the culture plates and accordingly the cross section of the inner face of the circumferential wall of the housing are/is of circular profile, the longitudinal axis of such a though hole can be arranged perpendicular to the radius of a face of the culture plate. In embodiments where the culture plates have an angular profile, e.g. with the shape of a triangle, a rectangle or a square the longitudinal axis of such a though hole can be arranged parallel to the closest edge of the culture plate. In embodiments where the faces of the culture plates are of circular profile it may be advantageous to select a through hole in the form of a slit of arcuated shape. The curvature of such an arcuated shape may define a radius, which may be arranged to at least essentially run in the direction of the radius of the culture plate. In one embodiment the curvature of a respective slit is arranged parallel to the circumference of the culture plate. A single, several or all of the culture plates of an apparatus of the invention may have an elongated shape as explained above. In one embodiment each culture plate has a slit of arcuated shape. Where the through holes of the culture plates are slits, the slits are likewise selected to be of dimensions that allow an at least essentially uniform flow distribution of a fluid flowing along the upper and lower faces of the plate. If for example a too wide or too narrow slit length and width is/are selected, the flow distribution will not be uniform, which will result in uneven distribution of nutrients and oxygen across the cell surface.

As already mentioned above, the culture plates are designed for the culture of anchorage-dependent cells. For this purpose the interior of each culture plate may include a suitable anchorage substrate for anchorage-dependent cells. The anchorage substrate may for example be deposited at a face of the culture plate. It may for instance be deposited at both the upper face and the lower face of the culture plate. It may also be deposited on a central face of the culture plate. It may in this regard also be deposited at both sides of the central face of the culture plate. The anchorage substrate may for example include one or more components of the extracellular matrix as present in higher organisms. It may for instance include a collagen.

By combining several apparatuses as defined above a cell culture system for culturing anchorage-dependent cells can be formed. A cell culture system for culturing anchorage-dependent cells according to the invention accordingly includes a plurality of apparatuses as described above. The plurality of apparatuses is removably arranged in a scaffold or in a housing. The apparatuses are positioned to allow a parallel connection of the inlets of the apparatuses to a feeding. In some embodiments the longitudinal axes defined by the inner cross sections of the housings of the apparatuses are arranged in parallel. In some embodiments the apparatuses are arranged on a common base plate. In some embodiments the cell culture system further includes a feeding conduit. The plurality of apparatuses may in such embodiments be connected in parallel to the feeding conduit via the inlets of the apparatuses. In some embodiments the inlets of the apparatuses are or have apertures of at least essentials identical profile. The cell culture system may further include a drain conduit. The plurality of apparatuses may be connected in parallel to the drain conduit via the outlets of the apparatuses. In some embodiments a control valve is coupled to each apparatus thereby allowing control of the flow of fluid through each apparatus. A respective control valve may for example be positioned adjacent to the inlet or to the outlet of an individual apparatus.

A respective system may further include further devices that provide desired functions such as maintaining an appropriate ambience in terms of e.g. temperature, atmosphere composition and humidity. The cell culture system may also include a device for mechanical blood filtration, including blood purification by e.g. sorption, hemofiltration and/or diafiltration. As an illustrative example, the system may include a dialysis module for continuous hemofiltration.

As mentioned above the culture plates can be removed from the apparatus. Hence, culture plates may be prepared in advance and be stacked in the apparatus for use. In this regard culturing anchorage-dependent cells may include providing a plurality of culture plates. The culture plates may be of any desired embodiment as explained above. Nonetheless the design of the culture plates and the design of the housing of the apparatus need to be selected to match as explained above. The outer dimensions of the culture plates have to match the inner dimensions of the housing, so as to allow mounting and sealing them to the circumferential wall of the housing.

Providing the plurality of culture plates may include assembling one or more, including each, of these culture plates. The culture plates may be assembled upon mounting into the housing. In some embodiments the culture plates are assembled to a defined unit in advance, i.e. before being mounted into the housing. In such embodiments each culture plate typically has a sleeve (supra). The sleeve defines the circumference of the culture plate and may be taken to define a circumferential wall of the culture plate. The sleeve may further define an annular stacking protrusion. Such an annular stacking protrusion is projecting upward and/or downward in relation to the culture plate when assembled to a unit. A respective annular stacking protrusion is thus projecting from the position of at least one of the upper and the lower face of the culture plate. An annular stacking protrusion may be projecting from the point of contact of the respective upper or lower face of the culture plate and the sleeve. An annular stacking protrusion may be projecting perpendicular to the plane defined by the culture plate. In any case the annular stacking protrusion is projecting from the plane of the face of the culture plate, which is orientated to the same side of the culture plate as the stacking protrusion. Accordingly an upper annular stacking protrusion is projecting from the plane of the upper face of the culture plate. An upper annular stacking protrusion may for instance project in a direction that is at least essentially perpendicular to the plane of the upper face of the culture plate. Likewise a lower annular stacking protrusion is projecting from the plane of the lower face of the culture plate.

In embodiments where a sleeve is used, each culture plate has an interior defined by the sleeve, the upper face and the lower face of the culture plate. As explained above, the sleeve may be included in a circumferential holder, which may be a two part holder. Assembling a culture plate may include providing a circumferential holder as defined above. Assembling may further include providing the lower face and the upper face. Accordingly, providing the plurality of culture plates may include providing a circumferential holder. The circumferential holder includes a circumferential wall and an annular fringe. The annular fringe is projecting inward from the circumferential wall of the holder. Assembling may include mounting the lower face and the upper face into the circumferential holder. The faces are mounted such that the circumferential holder forms a sleeve of the culture plate (see above) and holds the lower face and the upper face in position.

The circumferential holder used may be a two-part holder as defined above. The two-part holder may separably consist of an upper and a lower portion. The upper portion may include an upper annular fringe and an upper annular stacking protrusion. The lower portion may include a lower annular fringe and a lower annular stacking protrusion. The upper and the lower annular fringes of the circumferential holder are projecting inward from the circumferential wall of the holder. The upper and the lower annular fringes of the circumferential holder are designed to removably hold the lower face and the upper face of the culture plate, respectively, in position. The upper and the lower annular stacking protrusions of the circumferential holder are projecting at least essentially in the direction of the circumferential wall of the holder. In some embodiments the upper and the lower annular fringes of the circumferential holder that is being used are projecting inward from the circumferential wall of the holder in an at least essentially perpendicular direction thereof.

A housing as defined above is provided. The culture plates, in some embodiments after having been assembled, are mounted stacked into the housing. The plates are mounted in such a way that they are sealed to the circumferential wall of the housing. In some embodiments the housing may include fixtures. Such fixtures may be close-fitting with the culture plates to provide a seal. In some embodiments additional matter may be used as a sealing means, for example a glue. As explained above the culture plates are arranged at least essentially parallel to each other, with each culture plate being arranged at a distance from an adjacent culture plate. Further, as a result of mounting the through holes of adjacent culture plates are distally positioned in the housing in the plane defined by the at least essentially parallel arrangement of the culture plates. In some embodiments the plates are mounted in such a way that the through holes of adjacent culture plates are distally positioned in the housing in the plane of the inner cross section thereof.

Anchorage-dependent cells are seeded in the plurality of culture plates. In some embodiments a suitable anchorage substrate for anchorage-dependent cells is deposited in the interior of the culture plates. Generally the anchorage substrate is deposited first before cells are seeded. In some embodiments the anchorage substrate is deposited onto both the lower face and the upper face of the culture plates. In such embodiments the anchorage substrate may be deposited onto all upper and lower faces before they are assembled into culture plates. Cells may then be seeded onto the anchorage substrate. The upper and lower faces are then assembled with the anchorage substrate facing inward, i.e. into the interior of the culture plate(s). Hence, in embodiments where both the upper and the lower face of a culture plate have anchorage substrate deposited thereon, any cells seeded on the anchorage substrate of the upper and the lower face of the plate face each other. Cells seeded on the anchorage substrate of the upper and the lower face of the plate may in such embodiments also contact each other.

The anchorage-dependent cells may be any desired type of cells. The cells may for instance be cells of a cell line or cells isolated from the ambience. The cells may have been obtained from an organism. In some embodiments the cells have been isolated from an organism. In some embodiments the cells have been directly isolated from an organism while in other embodiments the cells have been isolated from an organism and subsequently been grown in culture before including them into an apparatus of the invention. In some embodiments the cells are animal cells, e.g. cells of a mammalian species, including a rodent species, an amphibian, e.g. of the subclass Lissamphibia that includes e.g. frogs, toads, salamanders or newts, an invertebrate species, or of a plant. Examples of mammals include, but are not limited to, a rat, a mouse, a rabbit, a guinea pig, a squirrel, a hamster, a hedgehog, a platypus, an American pika, an armadillo, a dog, a lemur, a goat, a pig, an opossum, a horse, an elephant, a bat, a woodchuck, an orang-utan, a rhesus monkey, a woolly monkey, a macaque, a chimpanzee, a tamarin (saguinus oedipus), a marmoset or a human. The cells may for instance be cells of a tissue, such as an organ or a portion thereof. Examples of a respective organ include, without being limited thereto, adrenal tissue, bone, bladder, brain, cartilage, colon, eye, heart, kidney, liver, lung, muscle, nerve, ovary, pancreas, prostate, skin, small intestine, spleen, stomach, testicular, thymus, tumour, vascular or uterus tissue, or connective tissue. In some embodiments the cells include hepatocytes. In such embodiments assembling the apparatus is a method of forming a liver assist device.

As explained above, in some embodiments at least one of the culture plates includes a central face sandwiched between the upper face and the lower face of the culture plate. This central face may be a central wall separating the culture plate into two compartments. In such embodiments the upper and the lower face of the respective culture plate may, to a certain degree, allow fluid to pass. The upper and the lower face may allow the diffusion of nutrients and water molecules, which can thereby access the two compartments of the culture plate. The upper and the lower face may for instance be defined by track-etch membranes, which may include a polymer such as polyethylene terephthalate (PET), polyvinylidene fluoride (PVDF), polypropylene (PP), a polyimide, CR-39 or polycarbonate (PC). The shape of pores in such a membrane may be freely selected. The shape of pores can be controlled upon their formation to be for instance cylindrical, conical, funnel-like, or cigar-like. An overview on the technique of track-etching has for example been given by Apel (*Radiation Measurements* (2001) 34, 559-566). In such embodiments the central face, e.g. the central wall, is at least essentially impermeable for fluid. A respective central wall has an upper side facing the upper face of the culture plate and a lower side facing the lower face of the culture plate. In some embodiments the anchorage substrate is deposited at both sides of the central wall of the culture plate. Cells seeded on the anchorage substrate are thus cultured on the two opposite faces of the central plate. In these embodiments the cells do not face each other but rather face the upper and the lower face of the culture plate, respectively. As explained above both the upper and the lower face of the culture plate may to a certain extend permit fluid to pass. As a result cells cultured on anchorage substrate on the central wall are exposed to a continuous supply of nutrients and oxygen once the apparatus is in use and fluid such as plasma or cell culture medium flows along the upper and lower faces of the culture plates (supra).

In some embodiments providing the plurality of culture plates includes providing a plurality of circumferential holders (cf. also above). This circumferential holder includes a circumferential wall and an annular fringe projecting inward from the circumferential wall of the holder. In such embodiments each culture plate is assembled by mounting the lower face and the upper face into the circumferential holder, such that the circumferential holder forms a sleeve of the culture plate and holds the lower face and the upper face in position. In some embodiments the culture chamber includes a central face, e.g. a central wall. In such an embodiment a respective culture plate is assembled by mounting the lower face, the central face and the upper face into the circumferential holder. In some embodiments only one or only a number smaller than the total number of culture plates is assembled using a circumferential holder as explained in the forgoing.

After assembling the culture plates the through hole may be formed by incising or drilling through each culture plate. The through hole may for instance be punched through the upper and the lower faces of the plate. In embodiments where at least one of the culture plates includes a central face sandwiched between the upper face and the lower face of the culture plate, after incising or drilling the through hole into the plate the through hole spans across the central face.

As explained above, in some embodiments the through hole is arranged in the upper and lower annular fringes of the holder of a culture plate. In such embodiments the upper and lower annular fringes of the holder may include perforations or bores. By means of corresponding perforations or bores in the upper and the lower portion of the holder the through-holes of the final assembled culture plates may be formed. These perforations or bores may for example serve as a guiding means, via the perforations or bores cutting, punching or drilling into/through the plates may be carried out. In some of these embodiments the through hole of the final culture plate is arranged at a position up to which only one or two or none of the upper, lower and, if present, the central face are spanning. In such embodiments the through hole, spanning the entire culture plate without spanning any of the upper, lower and central faces, is already defined once the upper, lower and optionally central face are assembled in the holder. Accordingly, where a holder is provided that has a respective through hole, no drilling or incising is required.

Once the apparatus has been assembled the flow of a medium may be allowed through the apparatus. The medium is allowed to enter the apparatus and thereby the culture chamber defined by its interior (supra) via the inlet of the housing and to leave the apparatus via the outlet of the housing. Hence, continuous in vitro perfusion can be provided for cells cultured within a culture plate of an apparatus of the invention.

In order that the invention may be readily understood and put into practical effect, particular embodiments will now be described by way of the following non-limiting examples. It is understood that modification of detail may be made without departing from the scope of the invention.

EXEMPLARY EMBODIMENTS OF THE INVENTION

Materials and Methods

Material 1.5 mg/ml neutralized collagen solution was prepared by mixing 8 ml of 3 mg/ml Type I Bovine dermal collagen (INAMED BioMaterials Corp, Fremont, Calif., USA), 1 ml 0.1 M NaOH, 1 ml 10×PBS and 6 ml 1×PBS. William's E culture medium (Sigma-Aldrich, Singapore) was supplemented with 1 mg/ml BSA, 10 ng/ml of EGF, 0.5 mg/ml of insulin, 5 nM dexamethasone, 50 ng/ml linoleic acid, 100 units/ml penicillin, and 100 mg/ml streptomycin. MTS assay using CellTiter 96 Aqueous One Solution Reagent was purchased from Promega, Singapore. Polyethylene Terephthalate (PET) film and PET track-etched membrane were purchased from Goodfellow Inc. of Cambridge, UK, and SterilTech Corp, Kent Wash., respectively.

Collagen Coating

PET film (bottom substratum) or PET track-etched membrane (top substratum) was cut into round plate with a diameter of 50 mm. Each respective plate of PET track-etched membrane would define the upper or lower face, respectively, of a culture plate, once assembled into an apparatus of the invention. Two plates of PET film would define the central face of a culture plate, once assembled into an apparatus of the invention. 600 μl of 1.5 mg/ml collagen solution was spotted onto hydrophobic petri dishes. PET film or membrane was placed on the droplet overnight at 4° C. before being transferred into a 37° C. incubator for one hour for collagen gelation to occur.

Hepatocytes Isolation and Sandwich Culture

Hepatocytes were harvested from male Wistar rats weighing 250-300 g by a two-step in situ collagenase perfusion method. Viability of the hepatocytes was determined to be >90% as determined by Trypan Blue exclusion assay with a yield of 1.5-2.0×10$^8$ cells/rat. 4 million freshly isolated hepatocytes suspended in 3.5 ml William's E culture medium were seeded onto collagen coated PET film. The medium was changed to remove unattached cells after 4 hours incubation. Hepatocytes were then overlaid with collagen coated PET membrane 24 hours after cell seeding. Hepatocyte sandwich culture was stabilized for an additional 24 hours before perfusion.

Bioreactor and Perfusion Circuit

The bioreactor system of the present example includes four vertically supported cylindrical culture chambers slotted onto a supporting platform (see FIG. 4). Each cylindrical chamber contains 24 stacked tissue culture plates. Each plate is made up of two interlocked O-rings use to secure 2 sandwich cell cultures with the bottom PET films facing each other. The final assembly has cell cultures at both top and bottom faces of the plate. The distance between adjacent plates is 1 mm, which is maintained by the circular extrusion along the edge of each plate. A slit is machined at the outer circumference of each plate so that during the placements of the plates into the cylindrical culture chamber, the slit of each holder is placed directly opposite those of its adjacent partners. This placement configuration allows the serial flow of culture media through each sandwich culture plate within the bioreactor. The current BLAD configuration ensures the optimal supply of nutrients and gases, at the same time allowing the removal and exchanges of metabolites, to and from the cell culture surfaces, thereby ensuring the long-term cellular viability and functionality in the bioreactor.

Figure 5:
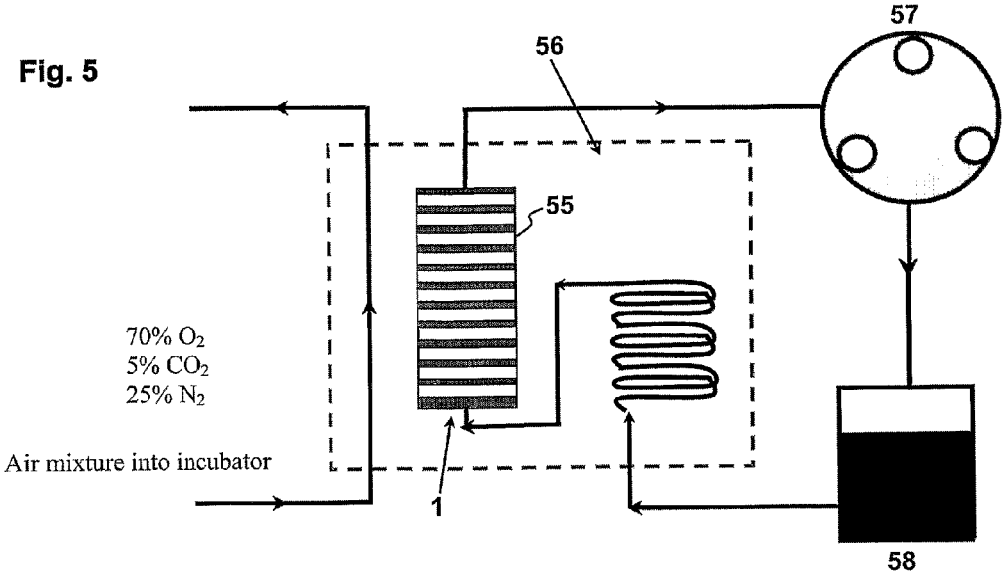
FIG. 5 is a schematic diagram of a cell culture system (3) according to the invention. The system is a perfusion circuit with one or more apparatuses (1) and oxygenator (55) inside an incubator (56) equilibrated to air mixture of 70% $O_2$, 5% $CO_2$, and 25% $N_2$. A peristaltic pump (57) and a reservoir (58) are included in the perfusion circuit.

The schematic of the perfusion loop, which includes a pump, a reservoir, an oxygenator unit and the bioreactor, is shown in FIG. 5. The perfusion direction through the bioreactor is bottom-top. The oxygenator, which consisted of 10 m long gas permeable Ismatec tubing (Tygon ST, Upchurch Scientific, United States) of 1.52 mm in inner diameter, is placed upstream of the bioreactor. The entire perfusion circuit is placed within an incubator set to a physiological temperature of 37° C. and the oxygenator is equilibrated to an air mixture of 70% $O_2$ 5% $CO_2$ and 25% $N_2$. The rationale for the elevated oxygen level is to meet the demand of larger cell mass and the serial flow configuration of the bioreactor.

Oxygen Concentration Measurement

The oxygen concentration at the inlet and outlet of the stack-plate sandwich culture bioreactor was measured using a VWR Dissolved Oxygen meter (Model 4000, VWR Scientific Products, Singapore) every day.

Hepatocyte Viability Assay

Live and dead cells were visualized using calcein AM and propidium iodine (PI) co-staining. Sandwich cultures were stained with 20 μM of calcein AM (Molecular Probes, USA) and 50 μg/ml of PI (Molecular Probes, USA) diluted with William's E culture medium for 30 minutes. After being rinsed with 1×PBS once, cell culture were viewed with confocal microscopy. Viable cells were stained with calcein AM while dead cell nuclei were stained with PI.

Hepatocyte Functional Assays

Culture medium was sampled every day in the perfusion and static culture for measurement of urea synthesis. The urea concentration in the sample medium was measured using Urea Nitrogen Kit (Stanbio Laboratory, Boerne, Tex.). MTS assay was to measure the mitochondrial dehydrogenase activity and was used as quantitative marker for cell viability. At the end of culture period, sandwich culture was exposed to 5×diluted MTS reagent in William's E culture medium and incubated for 3 hours at 37° C. The absorbance value was measured at 450 nm using microplate reader (Tecan Safire2). All the data were normalized to $10^6$ cells based on the number of seeded cells.

Computer Model

Figure 6:
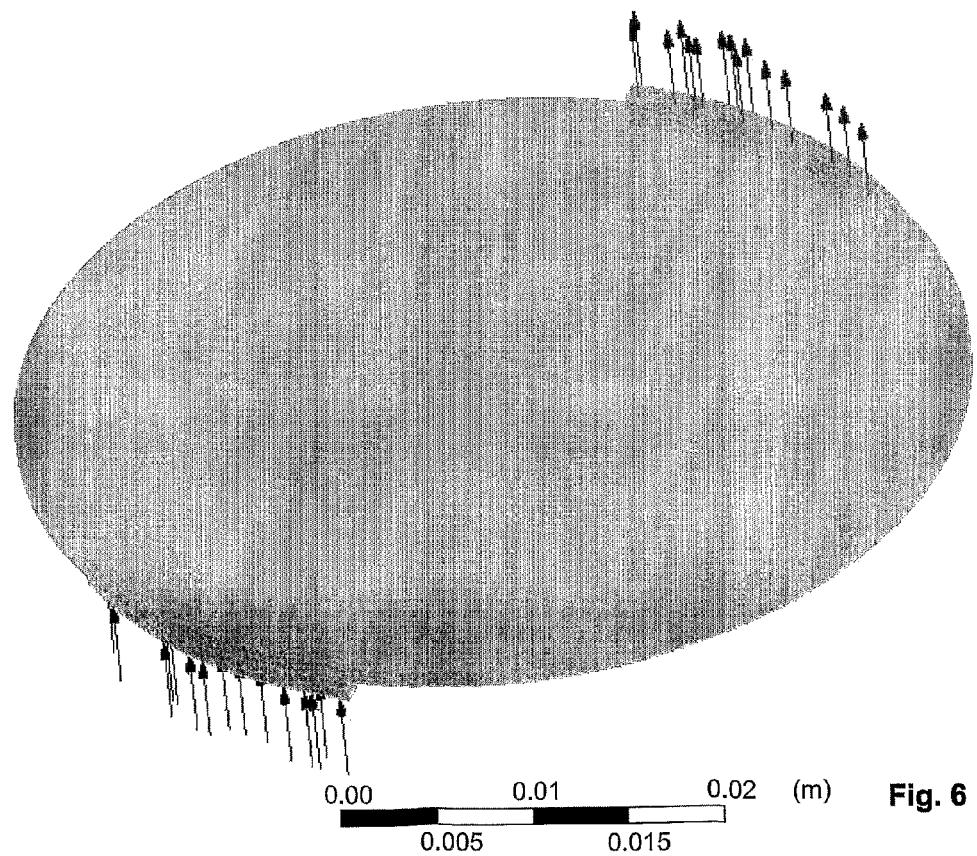
FIG. 6 is a three-dimensional tetrahedral meshed model for use in the modeling of fluid flow between two culture plates in an apparatus of the invention.

Since the entire bioreactor geometry is too large and complex to model, only a three-dimensional fluid volume between two sandwich stacked plates was modeled. FIG. 6 shows the three-dimensional computer model of the fluid flow between two culture plates with the inlet and outlet of the flow depicted by the protrusion from the peripheral of the disc. The fluid flow volume between the plates has the thickness of 1 mm and a diameter of 50 mm. Both inlet and outlet protrusion have height of 2 mm. The three-dimension model was first created using Solidworks (Solidworks, Singapore) before being discretized using ANSYS meshing software ICEM CFD (ANSYS, Singapore). Tetrahedral meshing was used for the volume discretization resulting in a total of 55360 nodes and 268755 elements.

Modeling Fluid Flow

A finite element approach was adopted in order to evaluate the distribution of fluid shear stress on the cell surface at various flow rates. To simulate the flow, the commercial CFD package (ANSYS Inc, Singapore) was used to numerically solve the steady-state Navier-Stokes equations. Fluid properties were set to those of the culture media and the culture medium was modeled as an incompressible, isothermal, Newtonian fluid with a density of 1000 kg/cm$^3$ and a dynamic viscosity of 0.889 mPa s. Flow rates of 1, 5 and 10 mL/min were simulated for comparison. Outlet boundary condition was set at zero pressure outflow, while the no-slip walls boundary conditions were used along the walls of the model.

Results

Wall Shear Stress

Figure 7:
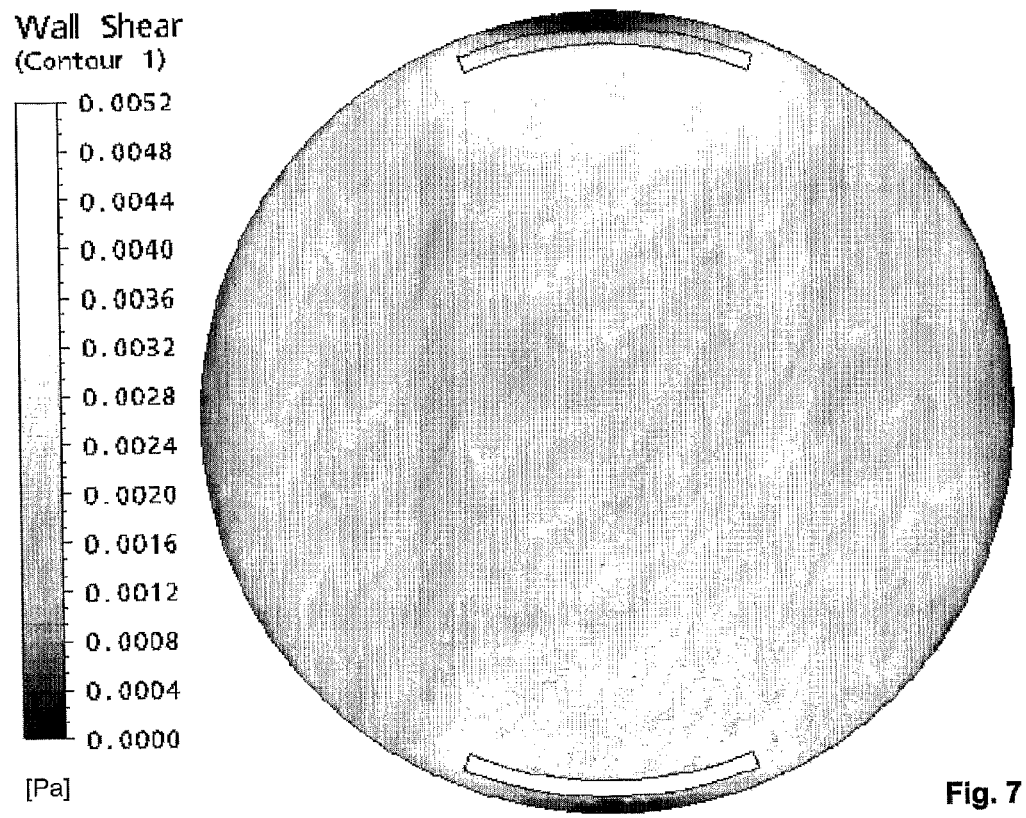
FIG. 7 is a contour plot of wall shear stress across the surface of the flow between two culture plates in an apparatus of the invention, at a flow rate of 1 mL/min. Elevated wall shear stresses of approximately 0.0048 Pa were observed at both sites of contact with a through hole of a culture plate, as the fluid enters and exits the flow volume, respectively, between two adjacent culture plates. These sites of contact with a through hole may be taken as inlet and outlet regions of the volume between two adjacent culture plates in the flow model.
Figure 8:
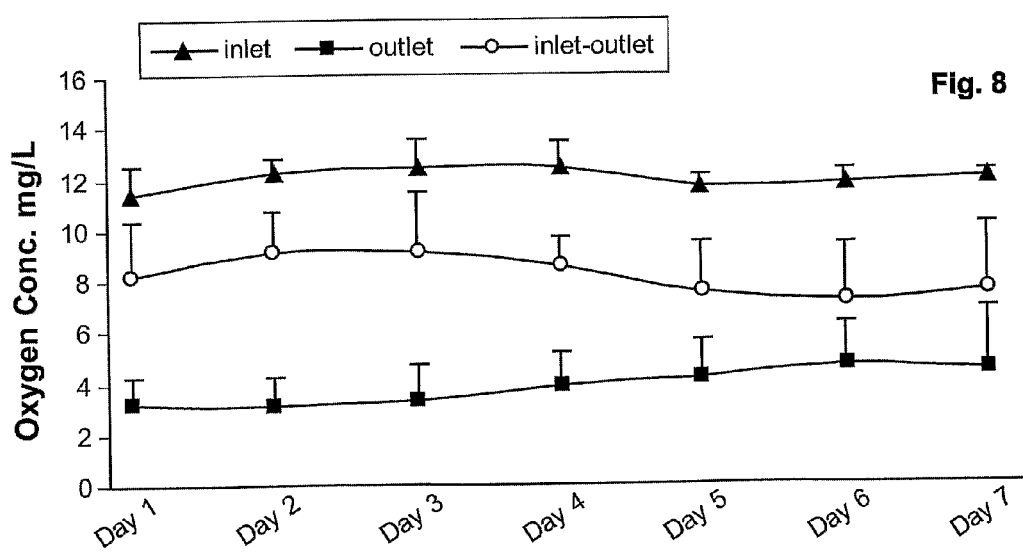
FIG. 8 shows the oxygen concentrations determined at the inlet and the outlet of an apparatus according to the invention. The oxygen consumption of the cells in the bioreactor is obtained by calculating the difference of the oxygen concentration at the inlet and outlet of the bioreactor.
Figure 11:
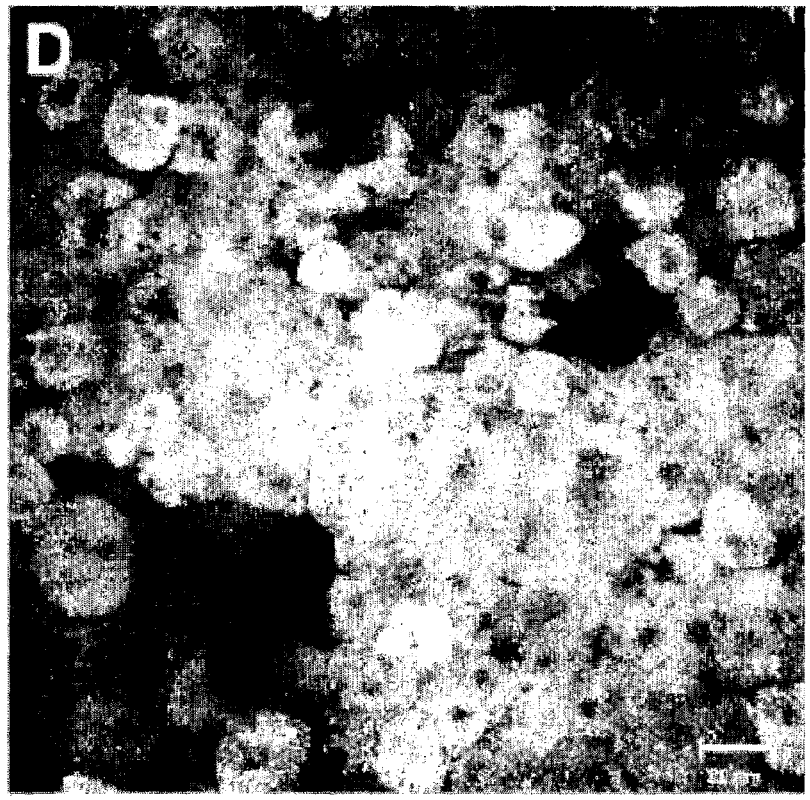
FIG. 11 depicts the average and maximum wall shear stresses at different flow rates on the surface of a cell culture plate in an apparatus of the invention.
Figure 12:
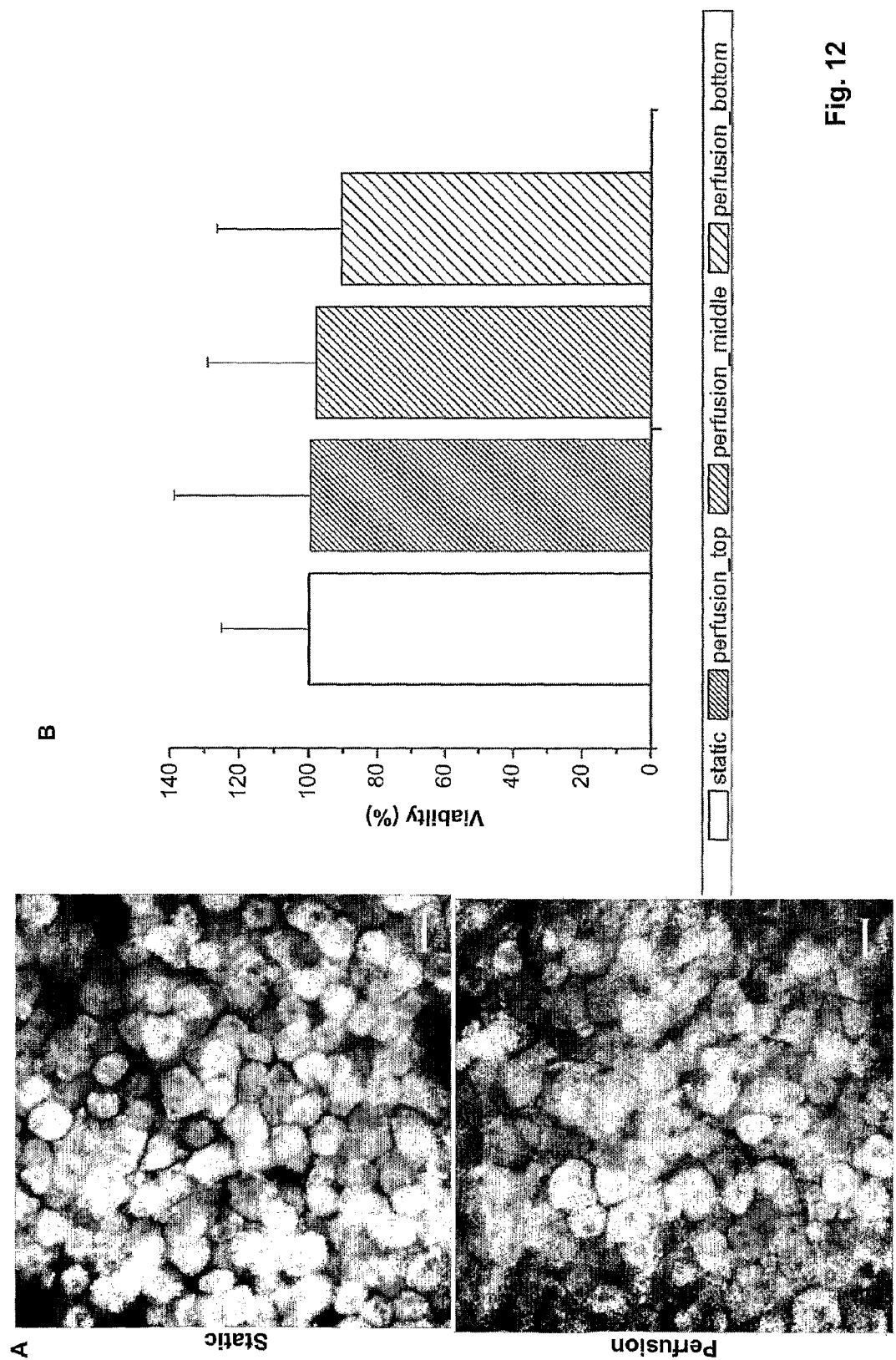
FIG. 12 depicts the cell viability at different locations within the apparatus compared to static culture (cf. the legend of FIG. 10). Cell viability was investigated by live and dead staining (Calcein AM and PI staining) (A). The cells were stained by calcein AM and shown in bright tone (green, see legend of FIG. 10), indicating as good as all the cells were alive in both static and perfusion culture. The white bar placed on each photo represents 20 µm. The viability was further quantified using MTS assay (B).
Figure 13:
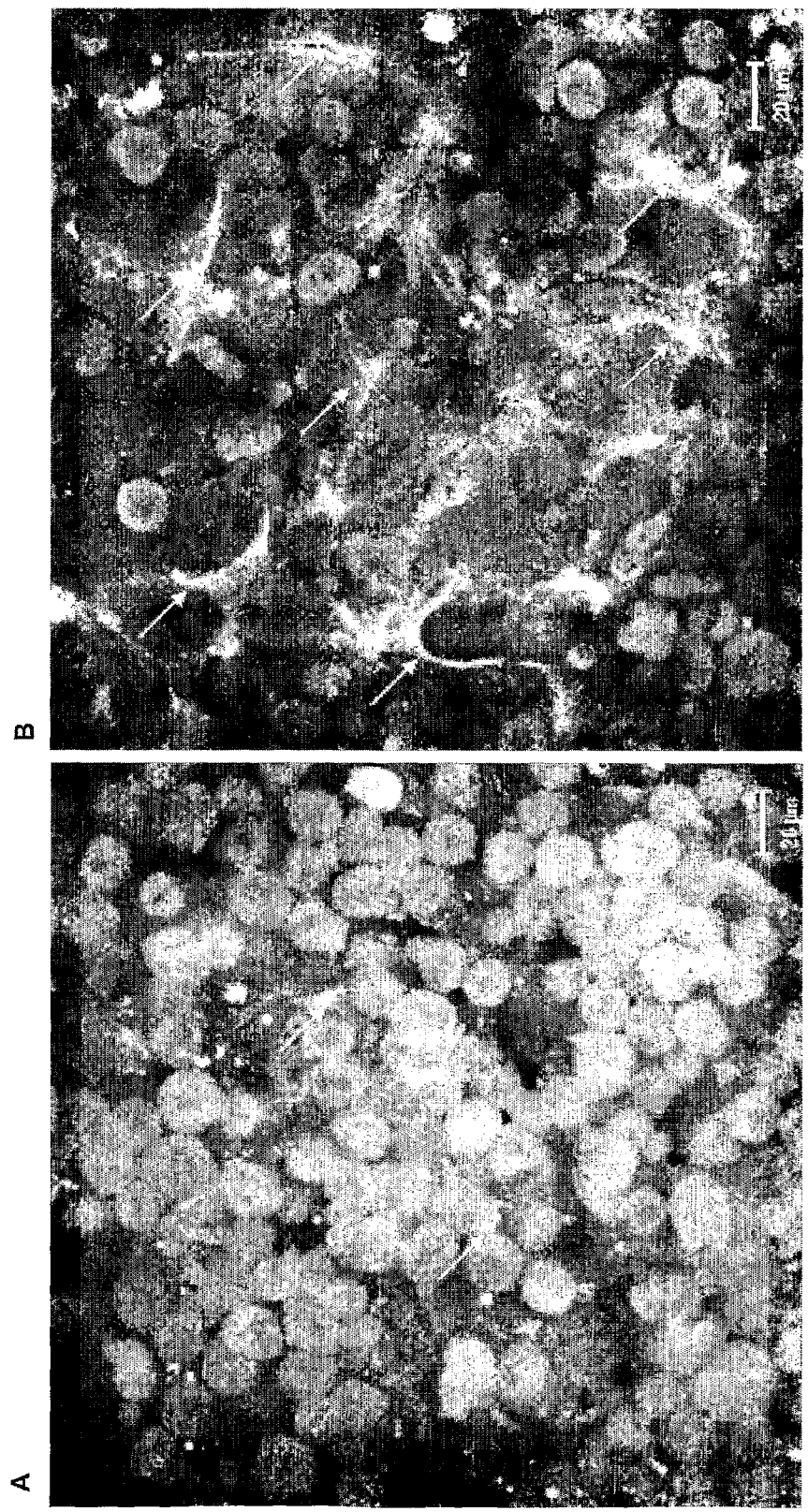
FIG. 13 shows the analysis of hepatocyte excretory functions of cells in static culture (A) and perfusion (B) in an apparatus of the invention, using fluorescein diacetate (FDA) staining. FDA was excreted out of the cells (arrows indicate excretion) and accumulated in the intercellular region, indicating good excretory function and cell re-polarization in the perfusion culture. The white bar placed on each photo represents 20 µm.
Figure 17C:
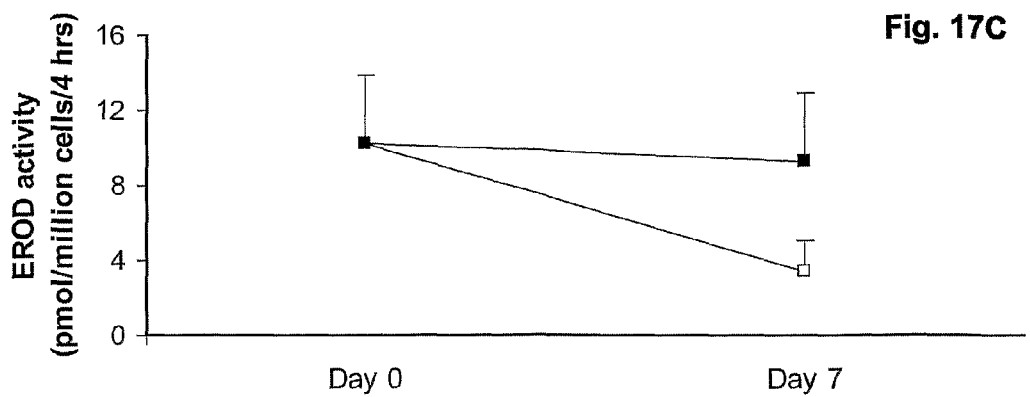
FIG. 17 shows the differentiated functions of albumin synthesis, (A), urea production (B), phase I enzyme activity (C) and phase II enzyme activity (D) of cells in perfusion culture using an apparatus of the invention (■) and in static culture (□).
Figure 17D:
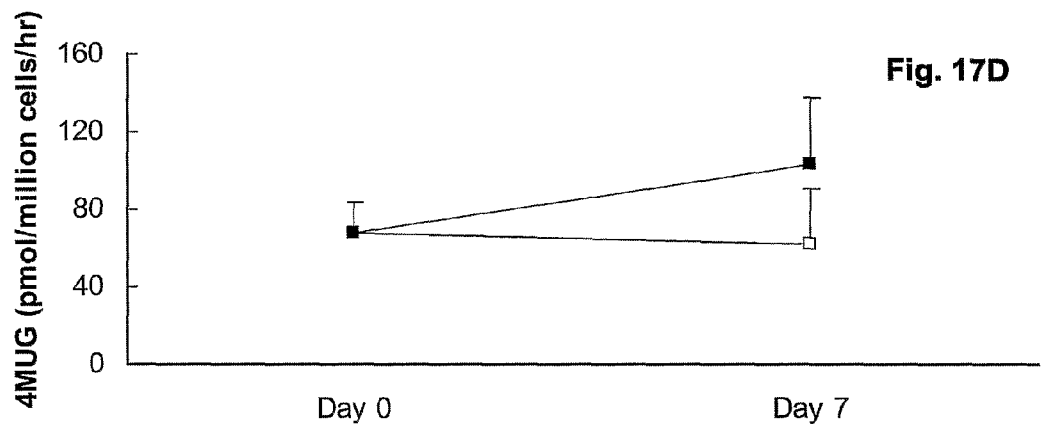

FIG. 11 tabulates the average and maximum wall shear stresses level on the surface of hepatocytes cultures (both top and bottom surfaces of the model). Taking the critical threshold of ≤0.033 Pa allowable for the hepatocytes culture (Park, J, et al., *Biotechnol Bioeng* (2008) 99, 2, 55-67), the wall shear stress levels generated by both flow rates of 1 and 5 mL/min fall within the acceptable range. On the other hand, the maximum shear stress level generated on the cell surfaces by flow rate of 10 mL/min may be detrimental to the hepatocytes culture. FIG. 7 shows the contour plot of wall shear stress across the surface of the flow between two culture plates at 1 mL/min. Elevated wall shear stresses of approximately 0.0048 Pa were observed at both the inlet and outlet regions of the flow model as the fluid enter and exit the flow volume, respectively. The wall shear level decreased to approximately 0.0016 Pa as the fluid flow between the two plates.

Hepatocyte Viability and Functions

In this study the stack-plate apparatus of the invention was evaluated by culturing rat hepatocytes over a perfusion period of 10 days at 2.12 mL/min, corresponding to a wall shear stress of 0.0042 Pa. This shear stress level has been shown to be well below the critical threshold detrimental to the long-term maintenance hepatocytes culture (Park, et al., 2008, supra). The inlet oxygen partial pressure in the bioreactor was kept at an elevated level of ~466 mmHg, taking into account the serial flow configuration of the bioreactor and the high oxygen consumption rate of the hepatocytes (Park, et al., 2008, supra; Curcio E, et al., *Biomaterials* (2007) 36, 5487-5497; Allen, J W, et al., *Toxicol Sci* (2005) 84, 1, 110-119). FIG. 9 shows the morphology of the 2D monolayer hepatocytes after 24 hours of pre-perfusion static stabilization, before the overlay of the collagen top layer.

The live and dead staining of the hepatocytes after 10 days of perfusion is shown in FIG. 10. Live cells were stained by calcein AM and shown in bright tone (green), while the nuclear of dead cells is stained by PI and shown in red: static culture (A), the bottom layer in perfusion culture (B), the middle layer in perfusion culture (C) and the top layer in perfusion culture (D). As good as all of the hepatocytes in the three different locations within the bioreactor were viable after the 10 days of perfusion. FIG. 14 shows the mitochondrial dehydrogenase activity (%) of the hepatocytes as monitored by the MTS assay after 10 days of perfusion. The activity of the sandwich perfusion culture in the bioreactor was normalized to that of the static cultures. MTS assay was commonly used as an indicator for cell viability. The perfusion culture showed the viability of 194% as compared to that of the static culture at 100%. These results demonstrated that the perfusion hepatocytes culture within a system according to the invention as the bioreactor was able to maintain high viability comparable to those in the static culture. FIG. 15 shows the dehydrogenase activity (%) of individual sandwich culture in the bioreactor after 10 days of perfusion. It can be seen that each perfusion culture plate had viability higher than that observed in the static culture.

In the current study, urea synthesis was used as a representative differentiated function of the hepatocytes in the perfusion culture. FIG. 16 compares the daily urea synthesis rate of both the perfusion and the static cultures. The normalized urea synthesis rates of the perfusion culture were shown to be consistently higher than those in the static culture. A marked decline in the urea synthesis from 73 to 31 $\mu g/\times 10^6$ cells/day was observed in the first two days of the perfusion culture, followed by a gradual decreased from the second to the fourth day, and finally stabilized at a range of 10-20 $\mu g/\times 10^6$ cells/day from the fifth day to the tenth day. For static culture, the urea synthesis rate was below 5 $\mu g/\times 10^6$ cells/day after the fifth day.

Discussion

Hepatocyte Functions in the Bioreactor

One of the several overarching aims of current BLAD designs is the maintenance of long-term viability and liver-specific functions of hepatocytes. And as such, two main, non-mutually exclusive, division of considerations need to be addressed in any BLAD devices: the biological and the engineering aspects. From the biological aspect, recent research focus has been the re-establishment of in vivo microenvironments in the hepatocytes culture: Several studies have shown that the creation of microenvironment mimicry of the liver native structure, after the hepatocytes isolation process, promote the re-establishment of the polarity in these hepatocytes cultures through the formation of bile canalicular network between contiguous cells and sealed by tight junctions, which invariably lead to longer culture period and significantly higher viability as well as liver-specific functions (Park, J K, & Lee, D H, *J Biosci Bioeng* (2005) 99, 4, 311-319; Allen, J W, & Bhatia, S N, *Semin Cell Dev Biol* (2002) 13, 6, 447-454; Marion, T L, et al., *Mol Pharm*. (2007) 4, 6, 911-918). In the current study sandwich culture configuration was used to evaluate the bioreactor design of an apparatus according to the invention. This intuitive technique strives to retain the sandwich configuration of the hepatocytes observed in vivo, where hepatocytes are organized into plates separated by sinusoidal cells. The space of Disse, thus formed between the hepatocytes and the sinusoidal cells, allows the drainage of metabolitic waste into the portal tract. From the engineering aspect, we strived to maintain conditions akin to those observed in vivo, i.e. sufficient delivery of oxygen supply to the cell surface and the regulation of fluid shear to allow the diffusive transport of oxygen and nutrient to the cell surfaces. To these ends, the present study has clearly demonstrated that a large hepatocytes culture (>100×10$^6$ cells) inside a perfusion bioreactor according to the invention can maintain better viability and liver-specific functions than culture in a static condition. Daily urea synthesis level of the perfusion culture was consistently higher than those observed in the static culture over the period of 10 days. The maximal urea synthesis rates found in the initial stage of the cultures (both in the static and perfusion cultures) can be attributed to the initial hypermetabolic state of the spreading of the hepatocytes (Smith, M D, et al., *Int J Artif Organs* (1996) 9, 36-44). This is followed by a more stable long term culture urea synthesis rate, which decreased from second to fifth day of culture before stabilizes from about seventh day onwards. MTS assays showed that the mitochondrial dehydrogenase activity of the hepatocytes in the perfusion culture was almost double than that observed in the static culture at day 10, which may be resulted from sufficient oxygen supply in perfusion culture.

Shear Stress Regulation in the Bioreactor

With a channel height of 1 mm and a flow rate of 2.12 mL/min, the fluid flow through the chamber is considered laminar flow with an estimated Reynolds number of 0.7, therefore diffusive transport dominates advective transport within the bioreactor. Similarly, viscous shear stress, as opposed to turbulence shear stress, dominates the characteristics of fluid shear experienced by the cells. The effect of fluid-induced shear stresses on hepatocytes has been well documented (Park, et al., 2008, supra; Tilles, A W, et al., *Biotechnol Bioeng* (1999) 73, 5, 379-389.). Numerical and experimental investigations have shown that exposing hepatocytes to shear stresses ≤0.033 Pa was not detrimental to their viability or function (ibid.). Computer simulation of the three flow rates at 1, 5 and 10 mL/min showed that the wall shear stresses were lower than that of the critical value (0.033 Pa). Even though the maximum wall shear stress of 10 mL/min (0.059 Pa) recorded at the inlet and outlet regions of the flow regimes exceeded that of the critical value (0.033 Pa), a large portion fluid volume between the plates recorded wall shear stress values were well below that of the threshold value. In general, the numerical studies have shown that elevated wall shear stresses were located mainly at the inlet and outlet of the flow volume because of the constriction of the flow area in these regions. Shear stresses level reduced gradually with the increase of the flow area between the two plates, where low wall shear stress values were typically observed at the cross-wise peripheral edge of the flow volume. In light of the current numerical investigation and previous studies, the fluid-induced shear stresses generated by flow rate of 2.12 mL/min used in this study should fall within the acceptable range of fluid shear not detrimental to the hepatocytes viability and function. Indeed, it was suggested that the flow rate could further be increased to 5 mL/min without incurring any shear induced damage on the cell culture.

Oxygen Tension Regulation in the Bioreactor

The maintenance of physiological oxygen partial pressure ($pO_2$) level for the sustenance of hepatocytes function has been an active area of research in bioreactor designs. The recorded $pO_2$ experienced by the hepatocytes in vivo is 3-4 mg/L (56-75 mm Hg) (Allen et al., 2005, supra; Smith, M D, et al., *Int J Artif Organs* (1996) 9, 36-44; Tilles et al., 1999, supra). However, given the numerous branching of capillaries, which resulted in copious parallel channeling of oxygen-rich blood supply to the hepatocytes, within the architectural structure of liver, it is not sensible to maintain similar inlet oxygen pressure of 75 mmHg for many of the current bioreactor designs, for the simple fact that far lesser branching of the oxygen supply can be effectively achieved with current technology. Further, a single pass of oxygen supply in a bioreactor typically encounter a larger mass of hepatocytes as compared to those observed in vivo. And as a result, many bioreactor designs nowaday have much higher $pO_2$ set at the inlet, typically in the range of 120-250 mmHg (Park et al., 2008, supra; Allen et al., 2005; supra; Tilles et al., 1999; supra; Smith et al., 1996, supra). The oxygen consumption rate (OCR) of hepatocytes has been experimentally shown to be in the range of 0.39-0.98 nmol/$\times 10^6$ cells/second (Allen et al., 2005; supra; Smith et al., 1996, supra; Tilles et al., 1999, supra). With this in mind, the setting of the inlet $pO_2$ level will invariably depend on the mass of the hepatocytes encounter by a single pass of oxygen rich media, the flow rate of the culture medium, and the design configuration of the bioreactor. To achieve such high level of $pO_2$ at the inlet, an oxygenator with at least 10 m long of silicone tubing is typically needed to equilibrate the culture media oxygen partial pressure with that of the atmosphere (~160 mmHg) (Park et al., 2008, supra). For $pO_2$ exceeding 160 mmHg, it is necessary to load the oxygenator in an environment with artificially elevated level of oxygen. For our current study, we supplied a 5% $CO_2$ incubator with air from a tank with of mixture 95% $O_2$ and 5% $CO_2$. Taking into account the $O_2$ diffusivity of the silicone tubing, the length of the coil, and the $pO_2$ of ~530 mmHg (it is not possible to achieved $pO_2$ of 722 mmHg because of the constant mixing of the gases from the tank with the atmospheric air), the $pO_2$ in the culture medium could reach level as high as ~446 mmHg within a day. Since the culture media was replaced everyday, the range of $pO_2$ experienced by the hepatocytes at the inlet of the bioreactor was recorded at ~446 mmHg, while the outlet was measured to be 130 mmHg. Since our bio-artificial liver device configuration is in essence a single pass bioreactor, such high $pO_2$ of ~446 mmHg is required for the ~7.0$\times 10^7$ cells.

Oxygen Toxicity

There is no documented literature on oxygen toxicity of hepatocytes, even though it has been suggested that elevated oxygen supply to the hepatocytes may enhanced the viability and function of the cell culture (Mareels, G, et al., *Ann Biomed Eng.* (2006) 34, 11, 1729-1744). A study by Mareels et al had shown that $pO_2$ of 235-250 mmHg led to higher metabolic stability and liver-specific functionality in their AMC Bioartificial Liver device (ibid.). In an earlier study by Yanagi et al demonstrated that under high oxygen tension of ~178-328 mmHg, albumin production and ammonium metabolic of rat hepatocytes in their pack-bed bioreactor are 17.9 and 10% higher than those in the bioreactor with normal oxygen tension (~100-128 mmHg) (Yanagi, K, et al., *ASAIO J* (1998) 44, M436-440). Hepatocytes culture in the apparatus of the invention under high oxygen tension did not demonstrate any adverse effect but have yielded viability and liver-specific functions better than those in the static culture. Hence, it is safe to surmise that our rat hepatocytes culture did not suffer any cellular damage as a result of the elevated $pO_2$.

Scalability of the Bioreactor

Scalability is an important consideration in all BLAD designs. Studies have shown that 10-20% of liver mass is sufficient to support a single patient (Mareels, G, et al., *Ann Biomed Eng* (2006) 34, 11, 1729-1744). Even with that amount, in a human patient it constitutes liver cells number of as much as 10-20$\times 10^9$, of approximately 1-2$\times 10^9$ in miniature pigs, and of approximately 100$\times 10^6$ in rat. At current setup, a single perfusion chamber of our BLAD system could support up to 300$\times 10^6$ rat hepatocytes, which is more than sufficient to support a single rat. Given that the hepatocytes of miniature pigs and human are approximately 1.5 smaller than those of the rat, four perfusion chambers of existing bioreactor design could pack up to 1.8$\times 10^9$ of porcine hepatocytes. Existing BLAD designs currently under clinical trials like the AMC Bioartificial Liver (Mareels et al., 2006, supra) (Hep-Art, Amsterdam, Netherland) support up to 10$\times 10^9$ porcine hepatocytes, while HepAssist21(Circe-Biomed. Inc, Los Angeles, Calif., USA) utilizes 5-7$\times 10^9$ cryopreserved porcine hepatocytes. To support a human patient, current design of our bioreactor need to be further scaled up by at least 5 times to accommodate the estimated 10$\times 10^9$ human hepatocytes. We envision that by doubling the existing diameter of our PET substrate from 50 mm to 100 mm, as well as the effective height of our perfusion chamber, our bioreactor could easily pack up to 10$\times 10^9$ human hepatocytes. This increase in cell number and density will lead to a concomitant increment of the oxygen tension at the inlet of the bioreactor and the flow rate necessary for the perfusion of larger cell mass.

Renewable Bio-artificial Liver Bioreactor as an Integrated Part of a an Existing Liver-dialysis System Besides ensuring efficacy of the bioreactor in treating patient with liver failure, one of the prime considerations in the development of the bioreactor is reducing the cost of the liver support system for patients. Studies have shown that early treatment with a bioreactor is effectively lower than the cost of liver transplantation, however, prolong treatment with the liver support system seen in many patients could well increase the overall treatment cost. One of the several attempts made to reduce the cost of treatment is through the use of polymeric hollow fiber cartridge as culture chamber, which is widely and commercially available, and has low production cost. However, these cartridges are still constraint by its one-time usage, which did not overcome the costly process of cell loading and culturing for each cartridge. To address such drawback, our group proposes the concept of a renewable bio-artificial bioreactor with the ability to restore the liver-specific functions of culture cells. The function enhancement of the culture liver cells is effected by switching the culture cartridge to a loop perfused with TGF-β1 supplemented culture medium. Preliminary studies in our lab have shown that a culture supplement consisting of TGF-β1 within defined range of effective concentrations and with suitable delivery/release vehicles has the ability to enhance the hepatocyte functions in simple hepatocyte culture configurations, i.e. without the supporting cells or sophisticated matrices or scaffolds. These studies indicated that TGF-β1 supplemented culture medium provide an economical and controllable way to culture hepatocytes with sustained high level functions for our bioreactor support applications. On the other hand, the culture cartridge perfused with TGF-β1 supplemented medium was temporarily removed from the exposure of patients toxic blood or plasma. The toxic metabolites excreted by hepatocytes to the surrounding region in the cartridge can be effectively wash-off during these perfusion phase. The intermittent perfusion strategy allows hepatocytes to regenerate their functions and the usage time for the cartridge is greatly prolonged.

Figure 18:
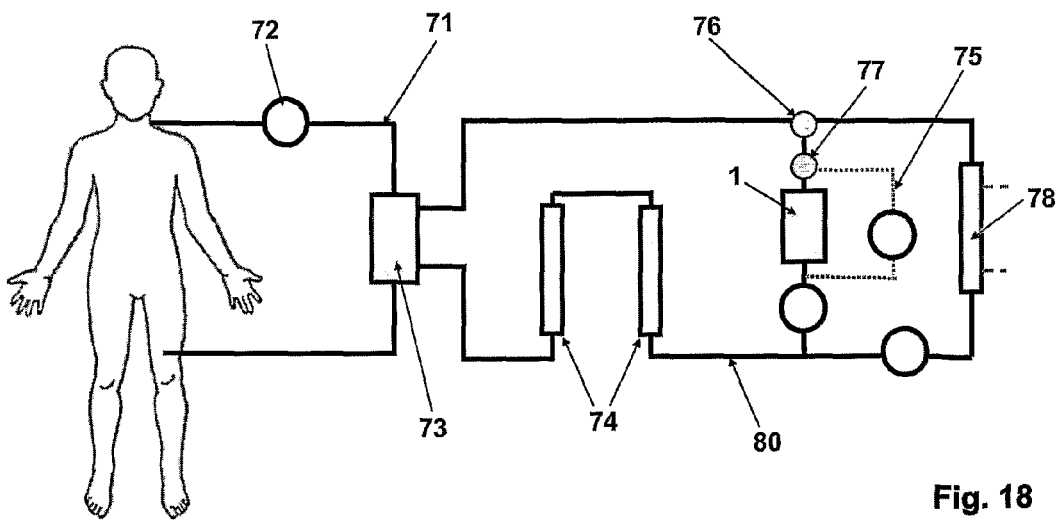
FIG. 18 is a schematic of a cell culture system according to the invention with an apparatus thereof (1), designed as an integrated module of an existing liver dialysis system with a blood circuit (71), a pump (72) and a plasma separator (73). A plasma circuit (80) of the system has adsorption columns (74) and a low-flux dialyzer (78). A separate TGF-β circuit (75) is incorporated to restore and enhance the hepatic functions of the culture system via a check valve (76) and a switch valve (77).

To evaluate further practical and commercial applicability, the perfusion system was designed to form an integrated module of an existing liver-dialysis system, which essentially makes use of filter with semi-permeable membrane for the sole purpose of blood detoxification. In contrast, the bioreactor provides an additional function of metabolism, which includes lipid and plasma lipoprotein synthesis and the production of serum albumin and clotting factors, often seen lacking in the existing liver-dialysis system. Our original design for the perfusion circuit of our bioreactor system comprises two loops, a blood circuit and a plasma circuit, interconnected by a plasma separator. Since the bioreactor is located in the plasma circuit, it can be easily incorporated into the plasma loop of the liver-dialysis system (FIG. 18). The flow rate in the plasma circuit of the liver dialysis typically exceeds 100 ml/min, well beyond that of our bioreactor critical range (1-20 ml/min), and as such a separate loop with a variable check valve upstream of the bioreactor will be installed to regulate the flow rate within acceptable range for the proper function of our culture chambers. The bioreactor is connected to an additional circuit that contains the TGF-β1 supplemented culture medium. A switch valve allows the bioreactor to switch between the plasma and the TGF-β1 loop.

SUMMARY

The above data demonstrate that a sandwich culture based stack-plate perfusion apparatus according to the invention is capable of regulating and shielding cells—using the example of hepatocytes—from the effects of shear stress caused by the flowing medium, and thereby allowing adequate convective oxygen delivery to the cells. Hepatocyte viability and function remained stable over 10 days of perfusion, and were increased compared to those in the static culture. By means of the present invention there is also presented the concept of renewable BLAD and the potential perfusion loop set-up, based on an apparatus of the invention. This study suggests that a bioreactor configuration based on the apparatus of the invention is scalable and has potential as a BLAD in the treatment of liver failure.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. An apparatus (1) for culturing anchorage-dependent cells, the apparatus (1) comprising a housing (2) with an inlet (4) and an outlet (5), and a plurality of culture plates (6) stacked within the housing (2), wherein the housing (2) has a circumferential wall (7), a base (8) and a top wall (9), the base (8) comprising the inlet (4) and the top wall (9) comprising the outlet (5), wherein the circumferential wall (7) of the housing (2) defines a longitudinal axis of the housing (2) and an inner cross section in a plane perpendicular to the longitudinal axis, wherein the inner cross section defined by the circumferential wall (7) of the housing (2) has a shape and dimensions that are at least essentially uniform along the longitudinal axis, wherein the culture plates (6) are arranged at least essentially parallel to each other, each culture plate (6) being mounted and sealed to the circumferential wall (7) of the housing (2) and being arranged at a distance from an adjacent culture plate (6), wherein each culture plate (6) is mounted and sealed to the circumferential wall (7) of the housing (2) by means of a sleeve (17) of the culture plate (6), the sleeve (17) defining the circumference of the culture plate (6) and defining an annular stacking protrusion (21), the annular stacking protrusion (21) projecting along the longitudinal axis of the housing (2);

wherein each culture plate (6) of the plurality of culture plates has an upper portion (19) and a lower portion (18) spaced from the upper portion (19), the upper portion (19), the lower portion (18) and sleeve (17) define an interior compartment of the cultural plate culture plate (6), wherein the interior compartment is adapted to allow an anchorage substrate (35) to be deposited onto at least one of the upper portion (19) or the lower portion (18) between the upper portion (19) and the lower portion (18), wherein the upper portion (19) and the lower portion (18) each comprises an aperture, wherein each culture plate (6) has a through hole (14), formed by aligning the apertures of the upper portion (19) and lower portion (18) to be opposite each other, such that the inlet (4) and the outlet (5) of the housing (2) are in fluid communication, wherein the through hole (14) of each culture plate (6) is positioned at an outer end of the culture plate (6), proximate the circumferential wall (7) of the housing (2), wherein the through holes (14) of adjacent culture plates (6) are distally positioned in the plane defined by the at least essentially parallel arrangement of the culture plates;

wherein the culture plate (6) is adapted to provide fluid flow into the interior compartment via an entrance only at one end of the culture plate (6) and fluid flow out of the interior compartment via an exit only at about the same end.

2. The apparatus of claim 1, wherein the through holes (14) of adjacent culture plates (6) are positioned at least essentially at opposite ends with respect to the longitudinal axis of the housing (2).

3. The apparatus of claim 1, wherein each culture plate (6) is at least essentially arranged in the plane of the inner cross section defined by the circumferential wall (7) of the housing (2).

4. The apparatus of claim 1, wherein a culture plate (6) of the plurality of culture plates (6) is mounted to an adjacent culture plate (6) via its annular stacking protrusion (21).

5. The apparatus of claim 4, wherein the annular stacking protrusions (21) of the plurality of culture plates (6) are of at least substantially uniform height along the longitudinal axis of the housing (2), thereby defining an at least essentially unitary distance between opposing portions of adjacent culture plates (6).

6. The apparatus of claim 1, wherein the distance between opposing portions of adjacent culture plates (6) is selected from about 0.5 mm to about 2 mm.

7. The apparatus of claim 1, wherein at least one of the upper and the lower portions (18, 19) of at least one culture plate (6) is porous.

8. The apparatus of claim 1, wherein the through holes (14) of the culture plates (6) are slits.

9. The apparatus of claim 8, wherein the slits are of arcuated shape.

10. The apparatus of claim 9, wherein the slits are arranged at least essentially parallel to the circumference of the culture plate (6).

11. The apparatus of claim 1, wherein the through hole (14) of each culture plate (6) is positioned at an outer end of the culture plate (6), proximate the sleeve (17) thereof.

12. The apparatus of claim 11, wherein the through hole (14) of each culture plate (6) is arranged at the edge thereof, such that the through hole (14) is laterally defined by the sleeve (17) of the culture plate (6).

13. The apparatus of claim 1, wherein the interior of each culture plate (6) comprises a suitable anchorage substrate (35) for anchorage-dependent cells.

14. The apparatus of claim 1, wherein at least one culture plate (6) further comprises a central layer (16) sandwiched between the upper portion (19) and the lower portion (18) of the culture plate (6).

15. The apparatus of claim 14, wherein the central layer (16) has an upper and a lower side, and wherein the anchorage substrate (35) is deposited at both sides of the central layer (16) of the culture plate (6).

16. The apparatus of claim 1, wherein the sleeve (17) has an upper annular stacking protrusion (21') and a lower annular stacking protrusion (21").

17. The apparatus of claim 16, wherein the sleeve (17) is comprised in a two-part holder (27),
the two-part holder separably consisting of an upper (29) and a lower (28) portion, wherein the upper portion comprises the upper annular stacking protrusion (21') and the lower part comprises the lower annular stacking protrusion (21").

18. The apparatus of claim 17, wherein the upper portion (29) of the two-part holder comprises an annular fringe (25'), the annular fringe (25') projecting inward from the circumferential sleeve of the holder in the plane defined by the parallel arrangement of the culture plates (6).

19. The apparatus of claim 18, wherein the annular fringe (25') comprises a lower portion configured to contact the upper portion (19) of the culture plate (6).

20. The apparatus of claim 18, wherein the through hole (14) of the at least one culture plate (6) is comprised in the annular fringe (25').

21. The apparatus of claim 1, wherein the lower portion (28) of the two-part holder comprises an annular fringe (25"), the annular fringe (25") projecting inward from the circumferential sleeve of the holder in the plane defined by the parallel arrangement of the culture plates (6).

22. The apparatus of claim 21, wherein the annular fringe (25") comprises an upper portion configured to contact the lower portion (18) of the at least one culture plate (6).

23. The apparatus of claim 1, wherein the base (8) and to the top wall (9) of the housing (2) are at least essentially parallel to the plane of the inner cross section of the circumferential wall (7) thereof.

24. The apparatus of claim 1, wherein the housing (2) defines an at least essentially cylindrical interior.

25. A cell culture system (3) for culturing anchorage-dependent cells, the culturing system (3) comprising a plurality of apparatuses (1) according to claim 1, wherein the plurality of apparatuses (1) is removably positioned by a scaffold or by a housing to allow a parallel connection of the inlets (4) of the apparatuses (1) to a feeding.

\* \* \* \* \*

UNITED STATES PATENT AND TRADEMARK OFFICE
CERTIFICATE OF CORRECTION

| | | |
|---|---|---|
| PATENT NO. | : 9,249,383 B2 | Page 1 of 1 |
| APPLICATION NO. | : 13/123200 | |
| DATED | : February 2, 2016 | |
| INVENTOR(S) | : Yu et al. | |

It is certified that error appears in the above-identified patent and that said Letters Patent is hereby corrected as shown below:

In the claims,

Column 37, Claim 1, line 22 should read -

--interior compartment of the culture plate--

Signed and Sealed this
Nineteenth Day of April, 2016

Michelle K. Lee
*Director of the United States Patent and Trademark Office*